US006521746B1

(12) United States Patent
Potter et al.

(10) Patent No.: US 6,521,746 B1
(45) Date of Patent: *Feb. 18, 2003

(54) POLYNUCLEOTIDES ENCODING LKT 111

(75) Inventors: Andrew A. Potter, Saskatoon (CA); John G. Manns, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/383,912

(22) Filed: Aug. 26, 1999

Related U.S. Application Data

(63) Continuation of application No. 09/124,491, filed on Jul. 29, 1998, now Pat. No. 6,022,960, which is a division of application No. 08/694,865, filed on Aug. 9, 1996, now Pat. No. 5,837,268, which is a continuation-in-part of application No. 08/387,156, filed on Feb. 10, 1995, now Pat. No. 5,723,129, which is a continuation-in-part of application No. 07/960,932, filed on Oct. 14, 1992, now Pat. No. 5,422,110, which is a continuation-in-part of application No. 07/779,171, filed on Oct. 16, 1991, now abandoned.

(51) Int. Cl.$^7$ .......................... C07H 21/02; C07H 21/04; C12P 21/06; C12P 21/04; C12N 15/00

(52) U.S. Cl. ..................... 536/23.1; 536/23.4; 536/23.7; 435/69.3; 435/69.7; 435/172.1; 435/172.3; 435/320.1; 435/252.3; 435/69.1

(58) Field of Search .............................. 536/23.1, 23.4, 536/23.7; 435/69.3, 69.7, 172.1, 172.3, 320.1, 252.3, 69.1

(56) References Cited

U.S. PATENT DOCUMENTS

| | | |
|---|---|---|
| 4,556,555 A | 12/1985 | Esbenshade |
| 4,608,251 A | 8/1986 | Mia |
| 4,692,412 A | 9/1987 | Livingston et al. |
| 4,975,420 A | 12/1990 | Silversides et al. |
| 5,028,423 A | 7/1991 | Prickett |
| 5,055,400 A | 10/1991 | Lo et al. |
| 5,071,651 A | 12/1991 | Sabara et al. |
| 5,238,823 A | 8/1993 | Potter et al. |
| 5,273,889 A | 12/1993 | Potter et al. |
| 5,403,586 A | 4/1995 | Russell-Jones et al. |
| 5,422,110 A | 6/1995 | Potter et al. |
| 5,476,657 A | 12/1995 | Potter |
| 5,534,256 A | 7/1996 | Potter et al. |
| 5,534,257 A | 7/1996 | Mastica et al. |
| 5,543,312 A | 8/1996 | Mellors et al. |
| 5,594,107 A | 1/1997 | Potter et al. |
| 5,708,155 A | 1/1998 | Potter et al. |
| 5,723,129 A | 3/1998 | Potter et al. |
| 5,837,268 A | 11/1998 | Potter et al. |
| 5,969,126 A | * 10/1999 | Potter et al. |
| 6,022,960 A | * 2/2000 | Potter et al. |

FOREIGN PATENT DOCUMENTS

| | | |
|---|---|---|
| CA | 2081950 | 2/1993 |
| CA | 2099707 | 3/1994 |
| WO | WO 86/07383 | 12/1986 |
| WO | WO 90/11298 | 10/1990 |
| WO | WO 91/02799 | 3/1991 |
| WO | WO 91/15237 | 10/1991 |
| WO | WO 92/03558 | 3/1992 |
| WO | WO 92/19746 | 11/1992 |
| WO | WO 93/08290 | 4/1993 |
| WO | WO 93/21323 | 10/1993 |
| WO | WO 96/24675 | 8/1996 |

OTHER PUBLICATIONS

Hsu et al, Cancer Research. 60:3701–3705, 2000.*
Strathdee et al, J. Bacteriol. 171/2: 916–928, 1989.*
Rusiecki et al Proc. Eur. Peptide Symp. 23$^{rd}$ Editor: Maia pp 765–766, 1994.*
Adams, T.E., et al., "Reproductive Function and Feedlot Performance of Beef Heifers Actively Immunized Against GnRH" *J. Anim. Sci.* 68:2793–2802 (1990).
Adams, T.E., et al., "Feedlot Performance of Steers and Bulls Actively Immunized Against Gonadotropin–Releasing Hormone" *J. Anim. Sci.* 70:1691–1698 (1992).
Arimura, A., et al., "Production of Antiserum to LH–Releasing Hormone (LH–RH) Associated with Gonadal Atrophy in Rabbits: Development of Radioimmunoassays for LH–RH" *Endocrinology* 93(5):1092–1103 (1973).
Bowie et al., "Deciphering the Message in Protein Sequences: Tolerance to Amino Acid Substitutions," *Science* 247:1306–1310.
Carelli, C. "Immunological Castration of Male Mice by a Totally Synthetic Vaccine Administered in Saline" *Proc. Natl. Acad. Sci. USA* 79:5392–5395 (1982).
Forestier et al., "Identification of RTX Toxin Target Cell Specificity Domains by Use of Hybrid Genes," *Infection & Immunity* 59(11):4212–4220 (1991).
Highlander et al., *J. Bacteriol.* 172(5):2343–2350 (1990).
Highlander et al., *DNA* 8(1):15–28 (1989).
Hoskinson, R.M., "Vaxstrate®: An Anti–reproductive Vaccine for Cattle" *Aust. J. Biotech.* 4(3):166–170 (1990).
Houghten et al., "Relative Importance of Position and Individual Amino Acid Residues in Peptide Antigen–Antibody Interactions: Implications in the Mechanism of Antigenic Drift and Antigenic Shift," *Vaccines* 86:21–25 (1986).
Hughes et al., *Inf. And Imm.* 60(2):565–570 (1992).

(List continued on next page.)

Primary Examiner—N M Minnifield
(74) Attorney, Agent, or Firm—Robins & Pasternak LLP

(57) ABSTRACT

New immunological carrier systems, DNA encoding the same, and the use of these systems, are disclosed. The carrier systems include chimeric proteins which include a leukotoxin polypeptide fused to one or more selected GnRH multimers which comprise at least one repeating GnRH decapeptide sequence, or at least one repeating unit of a sequence corresponding to at least one epitope of a selected GnRH molecule. Under the invention, the selected GnRH sequences may all be the same, or may correspond to different derivatives, analogues, variants or epitopes of GnRH so long as the GnRH sequences are capable of eliciting an immune response. The leukotoxin functions to increase the immunogenicity of the GnRH multimers fused thereto.

20 Claims, 37 Drawing Sheets

OTHER PUBLICATIONS

Lally et al., *JBC* 269(49):31289–31295 (1994).
Lerner et al., *The Biology of Immunologic Disease* (Ed:Dixon et al.) pp. 331–338.
Lo et al., *Infect. And Immun.* 55(9):1987–1996 (1987).
Meloen, R.H., et al., "Efficient Immunocastration of Male Piglets by Immunoneutralization of GnRH Using a New GnRH–like Peptide" *Vaccine* (1994) 12:741–774.
Que et al. "Effect of Carrier Selection in Immunogenicity of Protein Conjugate Vaccines Against *Plasmodium Falciparum* Circumsporozoites," *Inf. & Imm.* 56(10):2645–2649 (1988).

Sad et al., "Carrier–induced Suppression of the Antibody Response to a 'Self' Hapten," *Immunology* 74:223–227 (1991).
Siemeann, Eds. Kallman, In. *Rodent Tumor Model Exptal Cancer Therapy* pp. 12–15.
Stewart, A., "Immunization Using Recombinant TraT–L-HRH Fusion Proteins" *Vaccines* 51–55 (1992).
Welch, "Pore–Forming Cytolysins of Gram–Negative Bacteria," *Mol. Microbiol.* 5(3):521–528 (1991).
Westrop et al., *J. Bacteriol.* 179(3):871–879 (1997).

* cited by examiner

GnRH-1:

Gln His Trp Ser Tyr Gly Leu Arg Pro Gly
...CAG CAT TGG AGC TAC GGC CTG CGC CCT GGC...
...GTC GTA ACC TCG ATG CCG GAC GCG GGA CCG...

FIG. 1A

GnRH-2:

```
                                                                        (2)
     (1)
    [Gln His Trp Ser Tyr Gly Leu Arg Pro Gly Gly Ser Ser Gly Ser Gln Asp Trp Ser
...CAG CAT TGG AGC TAC GGC CTG CGC CCT GGC GGT TCT AGC GGT TCT CAA GAT TGG AGC
...GTC GTA ACC TCG ATG CCG GAC GCG GGA CCG CCA AGA TCG CCA AGA GTT CTA ACC TCG
    1                   5                  10                  15
                                    (3)
Tyr Gly Leu Arg Pro Gly Gly Ser Ser Gly Ser Gln His Trp Ser Tyr Gly Leu Arg
TAC GGC CTG CGC CCT GGC GGT TCT AGC GGT TCT AGC CAG CAT TGG AGC TAC GGC CTG CGC
ATG CCG GAC GCG GGA CCG CCA AGA TCG CCA AGA TCG GTC GTA ACC TCG ATG CCG GAC GCG
            20                  25                  30
                            (4)
Pro Gly Ser Gly Ser Gln Asp Trp Ser Tyr Gly Leu Arg Pro Gly]ₐ
CCT GGC AGC GGT AGC CAA GAT TGG AGC TAC GGC CTG CGT CCG GGT...
GGA CCG TCG CCA TCG GTT CTA ACC TCG ATG CCG GAC GCA GGC CCA...
        35                  40                  45              49
```

```
              10             20              30            40
               |              |               |             |
ATG GCT ACT GTT ATA GAT CTA AGC TTC CCA AAA ACT GGG GCA AAA
MET Ala Thr Val Ile Asp Leu Ser Phe Pro Lys Thr Gly Ala Lys 50             60              70            80            90
               |              |               |             |             |
AAA ATT ATC CTC TAT ATT CCC CAA AAT TAC CAA TAT GAT ACT GAA
Lys Ile Ile Leu Tyr Ile Pro Gln Asn Tyr Gln Tyr Asp Thr Glu 100            110             120           130
                      |              |               |             |
CAA GGT AAT GGT TTA CAG GAT TTA GTC AAA GCG GCC GAA GAG TTG
Gln Gly Asn Gly Leu Gln Asp Leu Val Lys Ala Ala Glu Glu Leu 140            150             160           170           180
              |              |               |             |             |
GGG ATT GAG GTA CAA AGA GAA GAA CGC AAT AAT ATT GCA ACA GCT
Gly Ile Glu Val Gln Arg Glu Glu Arg Asn Asn Ile Ala Thr Ala 190            200             210           220
                      |              |               |             |
CAA ACC AGT TTA GGC ACG ATT CAA ACC GCT ATT GGC TTA ACT GAG
Gln Thr Ser Leu Gly Thr Ile Gln Thr Ala Ile Gly Leu Thr Glu 230            240             250           260           270
      |              |               |             |             |
CGT GGC ATT GTG TTA TCC GCT CCA CAA ATT GAT AAA TTG CTA CAG
Arg Gly Ile Val Leu Ser Ala Pro Gln Ile Asp Lys Leu Leu Gln 280            290             300           310
                                                           |
AAA ACT AAA GCA GGC CAA GCA TTA GGT TCT GCC GAA AGC ATT GTA
Lys Thr Lys Ala Gly Gln Ala Leu Gly Ser Ala Glu Ser Ile Val 320            330             340           350           360
      |              |               |             |             |
CAA AAT GCA AAT AAA GCC AAA ACT GTA TTA TCT GGC ATT CAA TCT
Gln Asn Ala Asn Lys Ala Lys Thr Val Leu Ser Gly Ile Gln Ser 370            380             390           400
                             |               |             |
ATT TTA GGC TCA GTA TTG GCT GGA ATG GAT TTA GAT GAG GCC TTA
Ile Leu Gly Ser Val Leu Ala Gly MET Asp Leu Asp Glu Ala Leu
```

FIG. 5A

```
       410         420         430         440         450
        |           |           |           |           |
CAG AAT AAC AGC AAC CAA CAT GCT CTT GCT AAA GCT GGC TTG GAG
Gln Asn Asn Ser Asn Gln His Ala Leu Ala Lys Ala Gly Leu Glu 460         470         480         490
              |           |           |           |
CTA ACA AAT TCA TTA ATT GAA AAT ATT GCT AAT TCA GTA AAA ACA
Leu Thr Asn Ser Leu Ile Glu Asn Ile Ala Asn Ser Val Lys Thr 500         510         520         530         540
    |           |           |           |           |
CTT GAC GAA TTT GGT GAG CAA ATT AGT CAA TTT GGT TCA AAA CTA
Leu Asp Glu Phe Gly Glu Gln Ile Ser Gln Phe Gly Ser Lys Leu 550         560         570         580
              |           |           |           |
CAA AAT ATC AAA GGC TTA GGG ACT TTA GGA GAC AAA CTC AAA AAT
Gln Asn Ile Lys Gly Leu Gly Thr Leu Gly Asp Lys Leu Lys Asn 590         600         610         620         630
    |           |           |           |           |
ATC GGT GGA CTT GAT AAA GCT GGC CTT GGT TTA GAT GTT ATC TCA
Ile Gly Gly Leu Asp Lys Ala Gly Leu Gly Leu Asp Val Ile Ser 640         650         660         670
              |           |           |           |
GGG CTA TTA TCG GGC GCA ACA GCT GCA CTT GTA CTT GCA GAT AAA
Gly Leu Leu Ser Gly Ala Thr Ala Ala Leu Val Leu Ala Asp Lys 680         690         700         710         720
    |           |           |           |           |
AAT GCT TCA ACA GCT AAA AAA GTG GGT GCG GGT TTT GAA TTG GCA
Asn Ala Ser Thr Ala Lys Lys Val Gly Ala Gly Phe Glu Leu Ala 730         740         750         760
              |           |           |           |
AAC CAA GTT GTT GGT AAT ATT ACC AAA GCC GTT TCT TCT TAC ATT
Asn Gln Val Val Gly Asn Ile Thr Lys Ala Val Ser Ser Tyr Ile 770         780         790         800         810
    |           |           |           |           |
TTA GCC CAA CGT GTT GCA GCA GGT TTA TCT TCA ACT GGG CCT GTG
Leu Ala Gln Arg Val Ala Ala Gly Leu Ser Ser Thr Gly Pro Val
```

FIG. 5B

```
             820           830           840           850
              |             |             |             |
GCT GCT TTA ATT GCT TCT ACT GTT TCT CTT GCG ATT AGC CCA TTA
Ala Ala Leu Ile Ala Ser Thr Val Ser Leu Ala Ile Ser Pro Leu 860           870           880           890           900
       |             |             |             |             |
GCA TTT GCC GGT ATT GCC GAT AAA TTT AAT CAT GCA AAA AGT TTA
Ala Phe Ala Gly Ile Ala Asp Lys Phe Asn His Ala Lys Ser Leu 910           920           930           940
              |             |             |             |
GAG AGT TAT GCC GAA CGC TTT AAA AAA TTA GGC TAT GAC GGA GAT
Glu Ser Tyr Ala Glu Arg Phe Lys Lys Leu Gly Tyr Asp Gly Asp 950           960           970           980           990
       |             |             |             |             |
AAT TTA TTA GCA GAA TAT CAG CGG GGA ACA GGG ACT ATT GAT GCA
Asn Leu Leu Ala Glu Tyr Gln Arg Gly Thr Gly Thr Ile Asp Ala 1000          1010          1020          1030
              |             |             |             |
TCG GTT ACT GCA ATT AAT ACC GCA TTG GCC GCT ATT GCT GGT GGT
Ser Val Thr Ala Ile Asn Thr Ala Leu Ala Ala Ile Ala Gly Gly 1040          1050          1060          1070          1080
       |             |             |             |             |
GTG TCT GCT GCT GCA GCC GGC TCG GTT ATT GCT TCA CCG ATT GCC
Val Ser Ala Ala Ala Ala Gly Ser Val Ile Ala Ser Pro Ile Ala 1090          1100          1110          1120
              |             |             |             |
TTA TTA GTA TCT GGG ATT ACC GGT GTA ATT TCT ACG ATT CTG CAA
Leu Leu Val Ser Gly Ile Thr Gly Val Ile Ser Thr Ile Leu Gln 1130          1140          1150          1160          1170
       |             |             |             |             |
TAT TCT AAA CAA GCA ATG TTT GAG CAC GTT GCA AAT AAA ATT CAT
Tyr Ser Lys Gln Ala MET Phe Glu His Val Ala Asn Lys Ile His 1180          1190          1200          1210
              |             |             |             |
AAC AAA ATT GTA GAA TGG GAA AAA AAT AAT CAC GGT AAG AAC TAC
Asn Lys Ile Val Glu Trp Glu Lys Asn Asn His Gly Lys Asn Tyr
```

FIG. 5C

```
        1220            1230            1240            1250            1260
         |               |               |               |               |
TTT GAA AAT GGT TAC GAT GCC CGT TAT CTT GCG AAT TTA CAA GAT
Phe Glu Asn Gly Tyr Asp Ala Arg Tyr Leu Ala Asn Leu Gln Asp 1270            1280            1290            1300
                 |               |               |               |
AAT ATG AAA TTC TTA CTG AAC TTA AAC AAA GAG TTA CAG GCA GAA
Asn MET Lys Phe Leu Leu Asn Leu Asn Lys Glu Leu Gln Ala Glu 1310            1320            1330            1340            1350
         |               |               |               |               |
CGT GTC ATC GCT ATT ACT CAG CAG CAA TGG GAT AAC AAC ATT GGT
Arg Val Ile Ala Ile Thr Gln Gln Gln Trp Asp Asn Asn Ile Gly 1360            1370            1380            1390
                 |               |               |               |
GAT TTA GCT GGT ATT AGC CGT TTA GGT GAA AAA GTC CTT AGT GGT
Asp Leu Ala Gly Ile Ser Arg Leu Gly Glu Lys Val Leu Ser Gly 1400            1410            1420            1430            1440
         |               |               |               |               |
AAA GCC TAT GTG GAT GCG TTT GAA GAA GGC AAA CAC ATT AAA GCC
Lys Ala Tyr Val Asp Ala Phe Glu Glu Gly Lys His Ile Lys Ala 1450            1460            1470            1480
                 |               |               |               |
GAT AAA TTA GTA CAG TTG GAT TCG GCA AAC GGT ATT ATT GAT GTG
Asp Lys Leu Val Gln Leu Asp Ser Ala Asn Gly Ile Ile Asp Val 1490            1500            1510            1520            1530
         |               |               |               |               |
AGT AAT TCG GGT AAA GCG AAA ACT CAG CAT ATC TTA TTC AGA ACG
Ser Asn Ser Gly Lys Ala Lys Thr Gln His Ile Leu Phe Arg Thr 1540            1550            1560            1570
                 |               |               |               |
CCA TTA TTG ACG CCG GGA ACA GAG CAT CGT GAA CGC GTA CAA ACA
Pro Leu Leu Thr Pro Gly Thr Glu His Arg Glu Arg Val Gln Thr 1580            1590            1600            1610            1620
         |               |               |               |               |
GGT AAA TAT GAA TAT ATT ACC AAG CTC AAT ATT AAC CGT GTA GAT
Gly Lys Tyr Glu Tyr Ile Thr Lys Leu Asn Ile Asn Arg Val Asp
```

FIG. 5D

```
             1630            1640            1650            1660
              |               |               |               |
AGC TGG AAA ATT ACA GAT GGT GCA GCA AGT TCT ACC TTT GAT TTA
Ser Trp Lys Ile Thr Asp Gly Ala Ala Ser Ser Thr Phe Asp Leu 1670            1680            1690            1700            1710
        |               |               |               |               |
ACT AAC GTT GTT CAG CGT ATT GGT ATT GAA TTA GAC AAT GCT GGA
Thr Asn Val Val Gln Arg Ile Gly Ile Glu Leu Asp Asn Ala Gly 1720            1730            1740            1750
              |               |               |               |
AAT GTA ACT AAA ACC AAA GAA ACA AAA ATT ATT GCC AAA CTT GGT
Asn Val Thr Lys Thr Lys Glu Thr Lys Ile Ile Ala Lys Leu Gly 1760            1770            1780            1790            1800
        |               |               |               |               |
GAA GGT GAT GAC AAC GTA TTT GTT GGT TCT GGT ACG ACG GAA ATT
Glu Gly Asp Asp Asn Val Phe Val Gly Ser Gly Thr Thr Glu Ile 1810            1820            1830            1840
              |               |               |               |
GAT GGC GGT GAA GGT TAC GAC CGA GTT CAC TAT AGC CGT GGA AAC
Asp Gly Gly Glu Gly Tyr Asp Arg Val His Tyr Ser Arg Gly Asn 1850            1860            1870            1880            1890
              |               |               |               |               |
TAT GGT GCT TTA ACT ATT GAT GCA ACC AAA GAG ACC GAG CAA GGT
Tyr Gly Ala Leu Thr Ile Asp Ala Thr Lys Glu Thr Glu Gln Gly 1900            1910            1920            1930
              |               |               |               |
AGT TAT ACC GTA AAT CGT TTC GTA GAA ACC GGT AAA GCA CTA CAC
Ser Tyr Thr Val Asn Arg Phe Val Glu Thr Gly Lys Ala Leu His 1940            1950            1960            1970            1980
        |               |               |               |               |
GAA GTG ACT TCA ACC CAT ACC GCA TTA GTG GGC AAC CGT GAA GAA
Glu Val Thr Ser Thr His Thr Ala Leu Val Gly Asn Arg Glu Glu 1990            2000            2010            2020
              |               |               |               |
AAA ATA GAA TAT CGT CAT AGC AAT AAC CAG CAC CAT GCC GGT TAT
Lys Ile Glu Tyr Arg His Ser Asn Asn Gln His His Ala Gly Tyr
```

FIG. 5E

```
            2030         2040         2050         2060         2070
TAC ACC AAA GAT ACC TTG AAA GCT GTT GAA GAA ATT ATC GGT ACA
Tyr Thr Lys Asp Thr Leu Lys Ala Val Glu Glu Ile Ile Gly Thr 2080         2090         2100         2110
TCA CAT AAC GAT ATC TTT AAA GGT AGT AAG TTC AAT GAT GCC TTT
Ser His Asn Asp Ile Phe Lys Gly Ser Lys Phe Asn Asp Ala Phe 2120         2130         2140         2150         2160
AAC GGT GGT GAT GGT GTC GAT ACT ATT GAC GGT AAC GAC GGC AAT
Asn Gly Gly Asp Gly Val Asp Thr Ile Asp Gly Asn Asp Gly Asn 2170         2180         2190         2200
GAC CGC TTA TTT GGT GGT AAA GGC GAT GAT ATT CTC GAT GGT GGA
Asp Arg Leu Phe Gly Gly Lys Gly Asp Asp Ile Leu Asp Gly Gly 2210         2220         2230         2240         2250
AAT GGT GAT GAT TTT ATC GAT GGC GGT AAA GGC AAC GAC CTA TTA
Asn Gly Asp Asp Phe Ile Asp Gly Gly Lys Gly Asn Asp Leu Leu 2260         2270         2280         2290
CAC GGT GGC AAG GGC GAT GAT ATT TTC GTT CAC CGT AAA GGC GAT
His Gly Gly Lys Gly Asp Asp Ile Phe Val His Arg Lys Gly Asp 2300         2310         2320         2330         2340
GGT AAT GAT ATT ATT ACC GAT TCT GAC GGC AAT GAT AAA TTA TCA
Gly Asn Asp Ile Ile Thr Asp Ser Asp Gly Asn Asp Lys Leu Ser 2350         2360         2370         2380
TTC TCT GAT TCG AAC TTA AAA GAT TTA ACA TTT GAA AAA GTT AAA
Phe Ser Asp Ser Asn Leu Lys Asp Leu Thr Phe Glu Lys Val Lys 2390         2400         2410         2420         2430
CAT AAT CTT GTC ATC ACG AAT AGC AAA AAA GAG AAA GTG ACC ATT
His Asn Leu Val Ile Thr Asn Ser Lys Lys Glu Lys Val Thr Ile
```

FIG. 5F

```
            2440            2450            2460            2470
CAA AAC TGG TTC CGA GAG GCT GAT TTT GCT AAA GAA GTG CCT AAT
Gln Asn Trp Phe Arg Glu Ala Asp Phe Ala Lys Glu Val Pro Asn 2480            2490            2500            2510            2520
TAT AAA GCA ACT AAA GAT GAG AAA ATC GAA GAA ATC ATC GGT CAA
Tyr Lys Ala Thr Lys Asp Glu Lys Ile Glu Glu Ile Ile Gly Gln 2530            2540            2550            2560
AAT GGC GAG CGG ATC ACC TCA AAG CAA GTT GAT GAT CTT ATC GCA
Asn Gly Glu Arg Ile Thr Ser Lys Gln Val Asp Asp Leu Ile Ala 2570            2580            2590            2600            2610
AAA GGT AAC GGC AAA ATT ACC CAA GAT GAG CTA TCA AAA GTT GTT
Lys Gly Asn Gly Lys Ile Thr Gln Asp Glu Leu Ser Lys Val Val 2620            2630            2640            2650
GAT AAC TAT GAA TTG CTC AAA CAT AGC AAA AAT GTG ACA AAC AGC
Asp Asn Tyr Glu Leu Leu Lys His Ser Lys Asn Val Thr Asn Ser 2660            2670            2680            2690            2700
TTA GAT AAG TTA ATC TCA TCT GTA AGT GCA TTT ACC TCG TCT AAT
Leu Asp Lys Leu Ile Ser Ser Val Ser Ala Phe Thr Ser Ser Asn 2710            2720            2730            2740
GAT TCG AGA AAT GTA TTA GTG GCT CCA ACT TCA ATG TTG GAT CAA
Asp Ser Arg Asn Val Leu Val Ala Pro Thr Ser MET Leu Asp Gln 2750            2760            2770            2780            2790
AGT TTA TCT TCT CTT CAA TTT GCT AGG GGA TCT CAG CAT TGG AGC
Ser Leu Ser Ser Leu Gln Phe Ala Arg Gly Ser Gln His Trp Ser 2800            2810            2820            2830
TAC GGC CTG CGC CCT GGC AGC GGT TCT CAA GAT TGG AGC TAC GGC
Tyr Gly Leu Arg Pro Gly Ser Gly Ser Gln Asp Trp Ser Tyr Gly
```

FIG. 5G

```
     2840                2850              2860              2870              2880
      |                   |                 |                 |                 |
CTG  CGT  CCG  GGT  GGC  TCT  AGC  CAG  CAT  TGG  AGC  TAC  GGC  CTG  CGC
Leu  Arg  Pro  Gly  Gly  Ser  Ser  Gln  His  Trp  Ser  Tyr  Gly  Leu  Arg 2890              2900              2910              2920
      |                 |                 |                 |
CCT  GGC  AGC  GGT  AGC  CAA  GAT  TGG  AGC  TAC  GGC  CTG  CGT  CCG  GGT
Pro  Gly  Ser  Gly  Ser  Gln  Asp  Trp  Ser  Tyr  Gly  Leu  Arg  Pro  Gly

2930
  |
GGA  TCC  TAG
Gly  Ser  ---
```

```
                10              20              30              40
                 |               |               |               |
ATG GCT ACT GTT ATA GAT CTA AGC TTC CCA AAA ACT GGG GCA AAA
MET Ala Thr Val Ile Asp Leu Ser Phe Pro Lys Thr Gly Ala Lys 50              60              70              80              90
         |               |               |               |               |
AAA ATT ATC CTC TAT ATT CCC CAA AAT TAC CAA TAT GAT ACT GAA
Lys Ile Ile Leu Tyr Ile Pro Gln Asn Tyr Gln Tyr Asp Thr Glu 100             110             120             130
                 |               |               |               |
CAA GGT AAT GGT TTA CAG GAT TTA GTC AAA GCG GCC GAA GAG TTG
Gln Gly Asn Gly Leu Gln Asp Leu Val Lys Ala Ala Glu Glu Leu 140             150             160             170             180
         |               |               |               |               |
GGG ATT GAG GTA CAA AGA GAA GAA CGC AAT AAT ATT GCA ACA GCT
Gly Ile Glu Val Gln Arg Glu Glu Arg Asn Asn Ile Ala Thr Ala 190             200             210             220
                 |               |               |               |
CAA ACC AGT TTA GGC ACG ATT CAA ACC GCT ATT GGC TTA ACT GAG
Gln Thr Ser Leu Gly Thr Ile Gln Thr Ala Ile Gly Leu Thr Glu 230             240             250             260             270
         |               |               |               |               |
CGT GGC ATT GTG TTA TCC GCT CCA CAA ATT GAT AAA TTG CTA CAG
Arg Gly Ile Val Leu Ser Ala Pro Gln Ile Asp Lys Leu Leu Gln 280             290             300             310
                 |               |               |               |
AAA ACT AAA GCA GGC CAA GCA TTA GGT TCT GCC GAA AGC ATT GTA
Lys Thr Lys Ala Gly Gln Ala Leu Gly Ser Ala Glu Ser Ile Val 320             330             340             350             360
         |               |               |               |               |
CAA AAT GCA AAT AAA GCC AAA ACT GTA TTA TCT GGC ATT CAA TCT
Gln Asn Ala Asn Lys Ala Lys Thr Val Leu Ser Gly Ile Gln Ser 370             380             390             400
                 |               |               |               |
ATT TTA GGC TCA GTA TTG GCT GGA ATG GAT TTA GAT GAG GCC TTA
Ile Leu Gly Ser Val Leu Ala Gly MET Asp Leu Asp Glu Ala Leu
```

FIG. 7A

```
       410           420           430           440           450
        |             |             |             |             |
CAG AAT AAC AGC AAC CAA CAT GCT CTT GCT AAA GCT GGC TTG GAG
Gln Asn Asn Ser Asn Gln His Ala Leu Ala Lys Ala Gly Leu Glu 460           470           480           490
               |             |             |             |
CTA ACA AAT TCA TTA ATT GAA AAT ATT GCT AAT TCA GTA AAA ACA
Leu Thr Asn Ser Leu Ile Glu Asn Ile Ala Asn Ser Val Lys Thr 500           510           520           530           540
        |             |             |             |             |
CTT GAC GAA TTT GGT GAG CAA ATT AGT CAA TTT GGT TCA AAA CTA
Leu Asp Glu Phe Gly Glu Gln Ile Ser Gln Phe Gly Ser Lys Leu 550           560           570           580
               |             |             |             |
CAA AAT ATC AAA GGC TTA GGG ACT TTA GGA GAC AAA CTC AAA AAT
Gln Asn Ile Lys Gly Leu Gly Thr Leu Gly Asp Lys Leu Lys Asn 590           600           610           620           630
        |             |             |             |             |
ATC GGT GGA CTT GAT AAA GCT GGC CTT GGT TTA GAT GTT ATC TCA
Ile Gly Gly Leu Asp Lys Ala Gly Leu Gly Leu Asp Val Ile Ser 640           650           660           670
               |             |             |             |
GGG CTA TTA TCG GGC GCA ACA GCT GCA CTT GTA CTT GCA GAT AAA
Gly Leu Leu Ser Gly Ala Thr Ala Ala Leu Val Leu Ala Asp Lys 680           690           700           710           720
        |             |             |             |             |
AAT GCT TCA ACA GCT AAA AAA GTG GGT GCG GGT TTT GAA TTG GCA
Asn Ala Ser Thr Ala Lys Lys Val Gly Ala Gly Phe Glu Leu Ala 730           740           750           760
               |             |             |             |
AAC CAA GTT GTT GGT AAT ATT ACC AAA GCC GTT TCT TCT TAC ATT
Asn Gln Val Val Gly Asn Ile Thr Lys Ala Val Ser Ser Tyr Ile
```

FIG. 7B

```
      770           780           790           800           810
       |             |             |             |             |
TTA GCC CAA CGT GTT GCA GCA GGT TTA TCT TCA ACT GGG CCT GTG
Leu Ala Gln Arg Val Ala Ala Gly Leu Ser Ser Thr Gly Pro Val 820           830           840           850
               |             |             |             |
GCT GCT TTA ATT GCT TCT ACT GTT TCT CTT GCG ATT AGC CCA TTA
Ala Ala Leu Ile Ala Ser Thr Val Ser Leu Ala Ile Ser Pro Leu 860           870           880           890           900
              |             |             |             |             |
GCA TTT GCC GGT ATT GCC GAT AAA TTT AAT CAT GCA AAA AGT TTA
Ala Phe Ala Gly Ile Ala Asp Lys Phe Asn His Ala Lys Ser Leu 910           920           930           940
               |             |             |             |
GAG AGT TAT GCC GAA CGC TTT AAA AAA TTA GGC TAT GAC GGA GAT
Glu Ser Tyr Ala Glu Arg Phe Lys Lys Leu Gly Tyr Asp Gly Asp 950           960           970           980           990
       |             |             |             |             |
AAT TTA TTA GCA GAA TAT CAG CGG GGA ACA GGG ACT ATT GAT GCA
Asn Leu Leu Ala Glu Tyr Gln Arg Gly Thr Gly Thr Ile Asp Ala 1000          1010          1020          1030
              |             |             |             |
TCG GTT ACT GCA ATT AAT ACC GCA TTG GCC GCT ATT GCT GGT GGT
Ser Val Thr Ala Ile Asn Thr Ala Leu Ala Ala Ile Ala Gly Gly 1040          1050          1060          1070          1080
       |             |             |             |             |
GTG TCT GCT GCT GCA GCC AAC TTA AAA GAT TTA ACA TTT GAA AAA
Val Ser Ala Ala Ala Ala Asn Leu Lys Asp Leu Thr Phe Glu Lys 1090          1100          1110          1120
              |             |             |             |
GTT AAA CAT AAT CTT GTC ATC ACG AAT AGC AAA AAA GAG AAA GTG
Val Lys His Asn Leu Val Ile Thr Asn Ser Lys Lys Glu Lys Val 1130          1140          1150          1160          1170
       |             |             |             |             |
ACC ATT CAA AAC TGG TTC CGA GAG GCT GAT TTT GCT AAA GAA GTG
Thr Ile Gln Asn Trp Phe Arg Glu Ala Asp Phe Ala Lys Glu Val
```

FIG. 7C

|  | 1180 | 1190 | 1200 | 1210 |  |
|---|---|---|---|---|---|
| CCT | AAT TAT | AAA GCA ACT | AAA GAT GAG | AAA ATC GAA | GAA ATC ATC |
| Pro | Asn Tyr | Lys Ala Thr | Lys Asp Glu | Lys Ile Glu | Glu Ile Ile |

|  | 1220 | 1230 | 1240 | 1250 | 1260 |
|---|---|---|---|---|---|
| GGT | CAA AAT | GGC GAG | CGG ATC ACC | TCA AAG CAA | GTT GAT GAT CTT |
| Gly | Gln Asn | Gly Glu | Arg Ile Thr | Ser Lys Gln | Val Asp Asp Leu |

|  | 1270 | 1280 | 1290 | 1300 |  |
|---|---|---|---|---|---|
| ATC | GCA AAA | GGT AAC | GGC AAA ATT | ACC CAA GAT | GAG CTA TCA AAA |
| Ile | Ala Lys | Gly Asn | Gly Lys Ile | Thr Gln Asp | Glu Leu Ser Lys |

|  | 1310 | 1320 | 1330 | 1340 | 1350 |
|---|---|---|---|---|---|
| GTT | GTT GAT | AAC TAT | GAA TTG CTC | AAA CAT AGC | AAA AAT GTG ACA |
| Val | Val Asp | Asn Tyr | Glu Leu Leu | Lys His Ser | Lys Asn Val Thr |

|  | 1360 | 1370 | 1380 | 1390 |  |
|---|---|---|---|---|---|
| AAC | AGC TTA | GAT AAG | TTA ATC TCA | TCT GTA AGT | GCA TTT ACC TCG |
| Asn | Ser Leu | Asp Lys | Leu Ile Ser | Ser Val Ser | Ala Phe Thr Ser |

|  | 1400 | 1410 | 1420 | 1430 | 1440 |
|---|---|---|---|---|---|
| TCT | AAT GAT | TCG AGA | AAT GTA TTA | GTG GCT CCA | ACT TCA ATG TTG |
| Ser | Asn Asp | Ser Arg | Asn Val Leu | Val Ala Pro | Thr Ser MET Leu |

|  | 1450 | 1460 | 1470 | 1480 |  |
|---|---|---|---|---|---|
| GAT | CAA AGT | TTA TCT | TCT CTT CAA | TTT GCT AGG | GGA TCT CAG CAT |
| Asp | Gln Ser | Leu Ser | Ser Leu Gln | Phe Ala Arg | Gly Ser Gln His |

|  | 1490 | 1500 | 1510 | 1520 | 1530 |
|---|---|---|---|---|---|
| TGG | AGC TAC | GGC CTG | CGC CCT GGC | AGC GGT TCT | CAA GAT TGG AGC |
| Trp | Ser Tyr | Gly Leu | Arg Pro Gly | Ser Gly Ser | Gln Asp Trp Ser |

FIG. 7D

```
          1540           1550           1560           1570
           |              |              |              |
TAC GGC CTG CGT CCG GGT GGC TCT AGC CAG CAT TGG AGC TAC GGC
Tyr Gly Leu Arg Pro Gly Gly Ser Ser Gln His Trp Ser Tyr Gly 1580           1590           1600           1610           1620
      |              |              |              |              |
CTG CGC CCT GGC AGC GGT AGC CAA GAT TGG AGC TAC GGC CTG CGT
Leu Arg Pro Gly Ser Gly Ser Gln Asp Trp Ser Tyr Gly Leu Arg

1630
      |
CCG GGT GGA TCC TAG
Pro Gly Gly Ser ---
```

FIG. 7E

```
            [NaeI]                                    [BstB1]
..GCT GCA GCC|GGC TCG GTT ATT....TTC TCT GAT TCG|AAC TTA AAA..
..CGA CGT CGG|CCG AGC CAA TAA....AAG AGA CTA AGC|TTG AAT TTT...
..Ala Ala Ala|Gly Ser Val Ile....Phe Ser Asp Ser|Asn Leu Lys..
            351                                    785
```

FIG. 8A

```
..GCT GCA GCC   AAC TTA AAA..
..CGA CGT CGG   TTG AAT TTT...
..Ala Ala Ala   Asn Leu Lys...
        351   785
```

FIG. 8B

```
          10              20              30              40
           |               |               |               |
ATG GCT ACT GTT ATA GAT CGA TCT CAG CAT TGG AGC TAC GGC CTG
MET Ala Thr Val Ile Asp Arg Ser Gln His Trp Ser Tyr Gly Leu 50              60              70              80              90
       |               |               |               |               |
CGC CCT GGC AGC GGT TCT CAA GAT TGG AGC TAC GGC CTG CGT CCG
Arg Pro Gly Ser Gly Ser Gln Asp Trp Ser Tyr Gly Leu Arg Pro 100             110             120             130
           |               |               |               |
GGT GGC TCT AGC CAG CAT TGG AGC TAC GGC CTG CGC CCT GGC AGC
Gly Gly Ser Ser Gln His Trp Ser Tyr Gly Leu Arg Pro Gly Ser 140             150             160             170             180
       |               |               |               |               |
GGT AGC CAA GAT TGG AGC TAC GGC CTG CGT CCG GGT GGA TCT CAG
Gly Ser Gln Asp Trp Ser Tyr Gly Leu Arg Pro Gly Gly Ser Gln 190             200             210             220
           |               |               |               |
CAT TGG AGC TAC GGC CTG CGC CCT GGC AGC GGT TCT CAA GAT TGG
His Trp Ser Tyr Gly Leu Arg Pro Gly Ser Gly Ser Gln Asp Trp 230             240             250             260             270
       |               |               |               |               |
AGC TAC GGC CTG CGT CCG GGT GGC TCT AGC CAG CAT TGG AGC TAC
Ser Tyr Gly Leu Arg Pro Gly Gly Ser Ser Gln His Trp Ser Tyr 280             290             300             310
           |               |               |               |
GGC CTG CGC CCT GGC ACC GGT AGC CAA GAT TGG AGC TAC GGC CTG
Gly Leu Arg Pro Gly Ser Gly Ser Gln Asp Trp Ser Tyr Gly Leu
```

FIG. 9A

```
        320             330             340             350             360
         |               |               |               |               |
CGT CCG GGT GGA TCT AGC TTC CCA AAA ACT GGG GCA AAA AAA ATT
Arg Pro Gly Gly Ser Ser Phe Pro Lys Thr Gly Ala Lys Lys Ile 370             380             390             400
                  |               |               |               |
ATC CTC TAT ATT CCC CAA AAT TAC CAA TAT GAT ACT GAA CAA GGT
Ile Leu Tyr Ile Pro Gln Asn Tyr Gln Tyr Asp Thr Glu Gln Gly 410             420             430             440             450
     |               |               |               |               |
AAT GGT TTA CAG GAT TTA GTC AAA GCG GCC GAA GAG TTG GGG ATT
Asn Gly Leu Gln Asp Leu Val Lys Ala Ala Glu Glu Leu Gly Ile 460             470             480             490
                  |               |               |               |
GAG GTA CAA AGA GAA GAA CGC AAT AAT ATT GCA ACA GCT CAA ACC
Glu Val Gln Arg Glu Glu Arg Asn Asn Ile Ala Thr Ala Gln Thr 500             510             520             530             540
     |               |               |               |               |
AGT TTA GGC ACG ATT CAA ACC GCT ATT GGC TTA ACT GAG CGT GGC
Ser Leu Gly Thr Ile Gln Thr Ala Ile Gly Leu Thr Glu Arg Gly 550             560             570             580
                  |               |               |               |
ATT GTG TTA TCC GCT CCA CAA ATT GAT AAA TTG CTA CAG AAA ACT
Ile Val Leu Ser Ala Pro Gln Ile Asp Lys Leu Leu Gln Lys Thr 590             600             610             620             630
     |               |               |               |               |
AAA GCA GGC CAA GCA TTA GGT TCT GCC GAA AGC ATT GTA CAA AAT
Lys Ala Gly Gln Ala Leu Gly Ser Ala Glu Ser Ile Val Gln Asn 640             650             660             670
                  |               |               |               |
GCA AAT AAA GCC AAA ACT GTA TTA TCT GGC ATT CAA TCT ATT TTA
Ala Asn Lys Ala Lys Thr Val Leu Ser Gly Ile Gln Ser Ile Leu
```

FIG. 9B

```
     680              690             700             710            720
      |                |               |               |              |
GGC  TCA  GTA  TTG  GCT  GGA  ATG  GAT  TTA  GAT  GAG  GCC  TTA  CAG  AAT
Gly  Ser  Val  Leu  Ala  Gly  MET  Asp  Leu  Asp  Glu  Ala  Leu  Gln  Asn 730             740             750            760
                |               |               |              |
AAC  AGC  AAC  CAA  CAT  GCT  CTT  GCT  AAA  GCT  GGC  TTG  GAG  CTA  ACA
Asn  Ser  Asn  Gln  His  Ala  Leu  Ala  Lys  Ala  Gly  Leu  Glu  Leu  Thr 770             780             790            800             810
      |               |               |              |               |
AAT  TCA  TTA  ATT  GAA  AAT  ATT  GCT  AAT  TCA  GTA  AAA  ACA  CTT  GAC
Asn  Ser  Leu  Ile  Glu  Asn  Ile  Ala  Asn  Ser  Val  Lys  Thr  Leu  Asp 820             830             840            850
           |               |               |              |
GAA  TTT  GGT  GAG  CAA  ATT  AGT  CAA  TTT  GGT  TCA  AAA  CTA  CAA  AAT
Glu  Phe  Gly  Glu  Gln  Ile  Ser  Gln  Phe  Gly  Ser  Lys  Leu  Gln  Asn 860             870             880            890             900
      |               |               |              |               |
ATC  AAA  GGC  TTA  GGG  ACT  TTA  GGA  GAC  AAA  CTC  AAA  AAT  ATC  GGT
Ile  Lys  Gly  Leu  Gly  Thr  Leu  Gly  Asp  Lys  Leu  Lys  Asn  Ile  Gly 910             920             930            940
           |               |               |              |
GGA  CTT  GAT  AAA  GCT  GGC  CTT  GGT  TTA  GAT  GTT  ATC  TCA  GGG  CTA
Gly  Leu  Asp  Lys  Ala  Gly  Leu  Gly  Leu  Asp  Val  Ile  Ser  Gly  Leu 950             960             970            980             990
      |               |               |              |               |
TTA  TCG  GGC  GCA  ACA  GCT  GCA  CTT  GTA  CTT  GCA  GAT  AAA  AAT  GCT
Leu  Ser  Gly  Ala  Thr  Ala  Ala  Leu  Val  Leu  Ala  Asp  Lys  Asn  Ala 1000            1010            1020           1030
           |               |               |              |
TCA  ACA  GCT  AAA  AAA  GTC  GGT  GCG  GGT  TTT  GAA  TTG  GCA  AAC  CAA
Ser  Thr  Ala  lys  Lys  Val  Gly  Ala  Gly  Phe  Glu  Leu  Ala  Asn  Gln 1040            1050            1060           1070            1080
      |               |               |              |               |
GTT  GTT  GGT  AAT  ATT  ACC  AAA  GCC  GTT  TCT  TCT  TAC  ATT  TTA  GCC
Val  Val  Gly  Asn  Ile  Thr  Lys  Ala  Val  Ser  Ser  Tyr  Ile  Leu  Ala
```

FIG. 9C

```
        1090            1100           1110           1120
         |               |              |              |
CAA CGT GTT GCA GCA GGT TTA TCT TCA ACT GGG CCT GTG GCT GCT
Gln Arg Val Ala Ala Gly Leu Ser Ser Thr Gly Pro Val Ala Ala 1130           1140           1150           1160           1170
     |              |              |              |              |
TTA ATT GCT TCT ACT GTT TCT CTT GCG ATT AGC CCA TTA GCA TTT
Leu Ile Ala Ser Thr Val Ser Leu Ala Ile Ser Pro Leu Ala Phe 1180           1190           1200           1210
         |              |              |              |
GCC GGT ATT GCC GAT AAA TTT AAT CAT GCA AAA AGT TTA GAG AGT
Ala Gly Ile Ala Asp Lys Phe Asn His Ala Lys Ser Leu Glu Ser 1220           1230           1240           1250           1260
     |              |              |              |              |
TAT GCC GAA CGC TTT AAA AAA TTA GGC TAT GAC GGA GAT AAT TTA
Tyr Ala Glu Arg Phe Lys Lys Leu Gly Tyr Asp Gly Asp Asn Leu 1270           1280           1290           1300
         |              |              |              |
TTA GCA GAA TAT CAG CGG GGA ACA GGG ACT ATT GAT GCA TCG GTT
Leu Ala Glu Tyr Gln Arg Gly Thr Gly Thr Ile Asp Ala Ser Val 1310           1320           1330           1340           1350
     |              |              |              |              |
ACT GCA ATT AAT ACC GCA TTG GCC GCT ATT GCT GGT GGT GTG TCT
Thr Ala Ile Asn Thr Ala Leu Ala Ala Ile Ala Gly Cly Val Ser 1360           1370           1380           1390
         |              |              |              |
GCT GCT GCA GCC GAT TTA ACA TTT GAA AAA GTT AAA CAT AAT CTT
Ala Ala Ala Ala Asp Leu Thr Phe Glu Lys Val Lys His Asn Leu 1400           1410           1420           1430           1440
     |              |              |              |              |
GTC ATC ACG AAT AGC AAA AAA GAG AAA GTG ACC ATT CAA AAC TGG
Val Ile Thr Asn Ser Lys Lys Glu Lys Val Thr Ile Gln Asn Trp
```

FIG. 9D

```
        1450              1460              1470              1480
          |                 |                 |                 |
TTC CGA GAG GCT GAT TTT GCT AAA GAA GTG CCT AAT TAT AAA GCA
Phe Arg Glu Ala Asp Phe Ala Lys Glu Val Pro Asn Tyr Lys Ala
        1490              1500              1510              1520              1530
          |                 |                 |                 |                 |
ACT AAA GAT GAG AAA ATC GAA GAA ATC ATC GGT CAA AAT GGC GAG
Thr Lys Asp Glu Lys Ile Glu Glu Ile Ile Gly Gln Asn Gly Glu
              1540              1550              1560              1570
                |                 |                 |                 |
CGG ATC ACC TCA AAG CAA GTT GAT GAT CTT ATC GCA AAA GGT AAC
Arg Ile Thr Ser Lys Gln Val Asp Asp Leu Ile Ala Lys Gly Asn
        1580              1590              1600              1610              1620
          |                 |                 |                 |                 |
GGC AAA ATT ACC CAA GAT GAG CTA TCA AAA GTT GTT GAT AAC TAT
Gly Lys Ile Thr Gln Asp Glu Leu Ser Lys Val Val Asp Asn Tyr
              1630              1640              1650              1660
                |                 |                 |                 |
GAA TTG CTC AAA CAT AGC AAA AAT GTG ACA AAC AGC TTA GAT AAG
Glu Leu Leu Lys His Ser Lys Asn Val Thr Asn Ser Leu Asp Lys
        1670              1680              1690              1700              1710
          |                 |                 |                 |                 |
TTA ATC TCA TCT GTA AGT GCA TTT ACC TCG TCT AAT GAT TCG AGA
Leu Ile Ser Ser Val Ser Ala Phe Thr Ser Ser Asn Asp Ser Arg
              1720              1730              1740              1750
                |                 |                 |                 |
AAT GTA TTA GTG GCT CCA ACT TCA ATG TTG GAT CAA AGT TTA TCT
Asn Val Leu Val Ala Pro Thr Ser MET Leu Asp Gln Ser Leu Ser
        1760              1770              1780              1790              1800
          |                 |                 |                 |                 |
TCT CTT CAA TTT GCT AGG GGA TCT CAG CAT TGG AGC TAC GGC CTG
Ser Leu Gln Phe Ala Arg Gly Ser Gln His Trp Ser Tyr Gly Leu
```

FIG. 9E

```
                1810              1820              1830              1840
                 |                 |                 |                 |
CGC CCT GGC AGC GGT TCT CAA GAT TGG AGC TAC GGC CTG CGT CCG
Arg Pro Gly Ser Gly Ser Gln Asp Trp Ser Tyr Gly Leu Arg Pro 1850              1860              1870              1880              1890
         |                 |                 |                 |                 |
GGT GGC TCT AGC CAG CAT TGG AGC TAC GGC CTG CGC CCT GGC AGC
Gly Gly Ser Ser Gln His Trp Ser Tyr Gly Leu Arg Pro Gly Ser 1900              1910              1920              1930
             |                 |                 |                 |
GGT AGC CAA GAT TGG AGC TAC GGC CTG CGT CCG GGT GGA TCT CAG
Gly Ser Gln Asp Trp Ser Tyr Gly Leu Arg Pro Gly Gly Ser Gln 1940              1950              1960              1970              1980
         |                 |                 |                 |                 |
CAT TGG AGC TAC GGC CTG CGC CCT GGC AGC GGT TCT CAA GAT TGG
His Trp Ser Tyr Gly Leu Arg Pro Gly Ser Gly Ser Gln Asp Trp 1990              2000              2010              2020
             |                 |                 |                 |
AGC TAC GGC CTG CGT CCG GGT GGC TCT AGC CAG CAT TGG AGC TAC
Ser Tyr Gly Leu Arg Pro Gly Gly Ser Ser Gln His Trp Ser Tyr 2030              2040              2050              2060              2070
         |                 |                 |                 |                 |
GGC CTG CGC CCT GGC AGC GGT AGC CAA GAT TGG AGC TAC GGC CTG
Gly Leu Arg Pro Gly Ser Gly Ser Gln Asp Trp Ser Tyr Gly Leu 2080              2090              2100
             |                 |                 |
CGT CCG GGT GGA TCC TAG CTA GCT AGC CAT GG
Arg Pro Gly Gly Ser --- Leu Ala Ser His
```

FIG. 9F

1    MGTRLTTLSNGLKNTLTATKSGLHKAGQSLTQAGSSLKTGAKKIILYIPQNYQYDTEQGN
61   GLQDLVKAAEELGIEVQREERNNIATAQTSLGTIQTAIGLTERGIVLSAPQIDKLLQKTK
121  AGQALGSAESIVQNANKAKTVLSGIQSILGSVLAGMDLDEALQNNSNQHALAKAGLELTN
181  SLIENIANSVKTLDEFGEQISQFGSKLQNIKGLGTLGDKLKNIGGLDKAGLGLDVISGLL
241  SGATAALVLADKNASTAKKVGAGFELANQVVGNITKAVSSYILAQRVAAGLSSTGPVAAL
301  IASTVSLAISPLAFAGIADKFNHAKSLESYAERFKKLGYDGDNLLAEYQRGTGTIDASVT
361  AINTALAAIAGGVSAAAGRRIRGIPGDPVVLQRRDWENPGVTQLNRLAAHPPFASWRNSE
421  EARTDRPSQQLRSLNGEWRFAWFPAPEAVPESWLECDLPEADTVVVPSNWQMHGYDAPIY
481  TNVTYPITVNPPFVPTENPTGCYSLTFNVDESWLQEGQTRIIFDGVNSAFHLWCNGRWVG
541  YGQDSRLPSEFDLSAFLRAGENRLAVMVLRWSDGSYLEDQDMWRMSGIFRDVSLLHKPTT
601  QISDFHVATRFNDDFSRAVLEAEVQMCGELRDYLRVTVSLWQGETQVASGTAPFGGEIID
661  ERGGYADRVTLRLNVENPKLWSAEIPNLYRAVVELHTADGTLIEAEACDVGFREVRIENG

FIG. 11A

```
 721   LLLLNGKPLLIRGVNRHEHHPLHGQVMDEQTMVQDILLMKQNNFNAVRCSHYPNHPLWYT
 781   LCDRYGLYVVDEANIETHGMVPMNRLTDDPRWLPAMSERVTRMVQRDRNHPSVIIWSLGN
 841   ESGHGANHDALYRWIKSVDPSRPVQYEGGADTTATDIICPMYARVDEDQPFPAVPKWSI
 901   KKWLSLPGETRPLILCEYAHAMGNSLGGFAKYWQAFRQYPRLQGGFVWDWVDQSLIKYDE
 961   NGNPWSAYGGDFGDTPNDRQFCMNGLVFADRTPHPALTEAKHQQQFFQFRLSGQTIEVTS
1021   EYLFRHSDNELLHWMVALDGKPLASGEVPLDVAPQGKQLIELPELPQPESAGQLWLTVRV
1081   VQPNATAWSEAGHISAWQQWRLAENLSVTLPAASHAIPHLTTSEMDFCIELGNKRWQFNR
1141   QSGFLSQMWIGDKKQLLTPLRDQFTRAPLDNDIGVSEATRIDPNAWVERWKAAGHYQAEA
1201   ALLQCTADTLADAVLITTAHAWQHQGKTLFISRKTYRIDGSGQMAITVDVEVASDTPHPA
1261   RIGLNCQLAQVAERVNWLGLGPQENYPDRLTAACFDRWDLPLSDMYTPYVFPSENGLRCG
1321   TRELNYGPHQWRGDFQFNISRYSQQQLMETSHRHLLHAEEGTWLNIDGFHMGIGGDDSWS
1381   PSVSAEFQLSAGRYHYQLVWCQK
```

FIG. 11B

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..30

(xi) SEQUENCE DESCRIPTION: SEQ ID NO:1:

CAG CAT TGG AGC TAC GGC CTG CGC CCT GGC                                    30
Gln His Trp Ser Tyr Gly Leu Arg Pro Gly
  1               5                  10

(2) INFORMATION FOR SEQ ID NO:2:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:2:

Gln His Trp Ser Tyr Gly Leu Arg Pro Gly
  1               5                  10

(2) INFORMATION FOR SEQ ID NO:3:

(i) SEQUENCE CHARACTERISTICS:
        (A) LENGTH: 147 base pairs
        (B) TYPE: nucleic acid
        (C) STRANDEDNESS: double
        (D) TOPOLOGY: linear -continued

```
    (ii) MOLECULE TYPE: DNA (genomic)

(ix) FEATURE:
         (A) NAME/KEY: CDS
         (B) LOCATION: 1..147

(xi) SEQUENCE DESCRIPTION: SEQ ID NO:3:

CAG CAT TGG AGC TAC GGC CTG CGC CCT GGC AGC GGT TCT CAA GAT TGG        48
Gln His Trp Ser Tyr Gly Leu Arg Pro Gly Ser Gly Ser Gln Asp Trp
            15                  20                  25

AGC TAC GGC CTG CGT CCG GGT GGC TCT AGC CAG CAT TGG AGC TAC GGC        96
Ser Tyr Gly Leu Arg Pro Gly Gly Ser Ser Gln His Trp Ser Tyr Gly
                30                  35                  40

CTG CGC CCT GGC AGC GGT AGC CAA GAT TGG AGC TAC GGC CTG CGT CCG       144
Leu Arg Pro Gly Ser Gly Ser Gln Asp Trp Ser Tyr Gly Leu Arg Pro
        45                  50                  55

GGT                                                                   147
Gly (2) INFORMATION FOR SEQ ID NO:4:

(i) SEQUENCE CHARACTERISTICS:
         (A) LENGTH: 49 amino acids
         (B) TYPE: amino acid
         (D) TOPOLOGY: linear (ii) MOLECULE TYPE: protein (xi) SEQUENCE DESCRIPTION: SEQ ID NO:4:

Gln His Trp Ser Tyr Gly Leu Arg Pro Gly Ser Gly Ser Gln Asp Trp
 1               5                  10                  15

Ser Tyr Gly Leu Arg Pro Gly Gly Ser Ser Gln His Trp Ser Tyr Gly
                20                  25                  30

Leu Arg Pro Gly Ser Gly Ser Gln Asp Trp Ser Tyr Gly Leu Arg Pro
            35                  40                  45

Gly (2) INFORMATION FOR SEQ ID NO:5:

(i) SEQUENCE CHARACTERISTICS:
         (A) LENGTH: 2794 base pairs
         (B) TYPE: nucleic acid
         (C) STRANDEDNESS: double
         (D) TOPOLOGY: linear (ii) MOLECULE TYPE: DNA (genomic)

(ix) FEATURE:
         (A) NAME/KEY: CDS
         (B) LOCATION: 1..2778

(xi) SEQUENCE DESCRIPTION: SEQ ID NO:5:

ATG GCT ACT GTT ATA GAT CTA AGC TTC CCA AAA ACT GGG GCA AAA AAA        48
Met Ala Thr Val Ile Asp Leu Ser Phe Pro Lys Thr Gly Ala Lys Lys
 50                  55                  60                  65

ATT ATC CTC TAT ATT CCC CAA AAT TAC CAA TAT GAT ACT GAA CAA GGT        96
Ile Ile Leu Tyr Ile Pro Gln Asn Tyr Gln Tyr Asp Thr Glu Gln Gly
                70                  75                  80

AAT GGT TTA CAG GAT TTA GTC AAA GCG GCC GAA GAG TTG GGG ATT GAG       144
Asn Gly Leu Gln Asp Leu Val Lys Ala Ala Glu Glu Leu Gly Ile Glu
            85                  90                  95

GTA CAA AGA GAA GAA CGC AAT AAT ATT GCA ACA GCT CAA ACC AGT TTA       192
Val Gln Arg Glu Glu Arg Asn Asn Ile Ala Thr Ala Gln Thr Ser Leu
        100                 105                 110
```

-continued

| | | |
|---|---|---|
| GGC ACG ATT CAA ACC GCT ATT GGC TTA ACT GAG CGT GGC ATT GTG TTA<br>Gly Thr Ile Gln Thr Ala Ile Gly Leu Thr Glu Arg Gly Ile Val Leu<br>115                           120                   125 | 240 |
| TCC GCT CCA CAA ATT GAT AAA TTG CTA CAG AAA ACT AAA GCA GGC CAA<br>Ser Ala Pro Gln Ile Asp Lys Leu Leu Gln Lys Thr Lys Ala Gly Gln<br>130                       135                   140                  145 | 288 |
| GCA TTA GGT TCT GCC GAA AGC ATT GTA CAA AAT GCA AAT AAA GCC AAA<br>Ala Leu Gly Ser Ala Glu Ser Ile Val Gln Asn Ala Asn Lys Ala Lys<br>                150                   155                  160 | 336 |
| ACT GTA TTA TCT GGC ATT CAA TCT ATT TTA GGC TCA GTA TTG GCT GGA<br>Thr Val Leu Ser Gly Ile Gln Ser Ile Leu Gly Ser Val Leu Ala Gly<br>               165                  170                 175 | 384 |
| ATG GAT TTA GAT GAG GCC TTA CAG AAT AAC AGC AAC CAA CAT GCT CTT<br>Met Asp Leu Asp Glu Ala Leu Gln Asn Asn Ser Asn Gln His Ala Leu<br>180                           185                   190 | 432 |
| GCT AAA GCT GGC TTG GAG CTA ACA AAT TCA TTA ATT GAA AAT ATT GCT<br>Ala Lys Ala Gly Leu Glu Leu Thr Asn Ser Leu Ile Glu Asn Ile Ala<br>195                           200                   205 | 480 |
| AAT TCA GTA AAA ACA CTT GAC GAA TTT GGT GAG CAA ATT AGT CAA TTT<br>Asn Ser Val Lys Thr Leu Asp Glu Phe Gly Glu Gln Ile Ser Gln Phe<br>210                           215                   220                  225 | 528 |
| GGT TCA AAA CTA CAA AAT ATC AAA GGC TTA GGG ACT TTA GGA GAC AAA<br>Gly Ser Lys Leu Gln Asn Ile Lys Gly Leu Gly Thr Leu Gly Asp Lys<br>                230                  235                  240 | 576 |
| CTC AAA AAT ATC GGT GGA CTT GAT AAA GCT GGC CTT GGT TTA GAT GTT<br>Leu Lys Asn Ile Gly Gly Leu Asp Lys Ala Gly Leu Gly Leu Asp Val<br>               245                  250                 255 | 624 |
| ATC TCA GGG CTA TTA TCG GGC GCA ACA GCT GCA CTT GTA CTT GCA GAT<br>Ile Ser Gly Leu Leu Ser Gly Ala Thr Ala Ala Leu Val Leu Ala Asp<br>260                           265                   270 | 672 |
| AAA AAT GCT TCA ACA GCT AAA AAA GTG GGT GCG GGT TTT GAA TTG GCA<br>Lys Asn Ala Ser Thr Ala Lys Lys Val Gly Ala Gly Phe Glu Leu Ala<br>275                           280                   285 | 720 |
| AAC CAA GTT GTT GGT AAT ATT ACC AAA GCC GTT TCT TCT TAC ATT TTA<br>Asn Gln Val Val Gly Asn Ile Thr Lys Ala Val Ser Ser Tyr Ile Leu<br>290                           295                   300                  305 | 768 |
| GCC CAA CGT GTT GCA GCA GGT TTA TCT TCA ACT GGG CCT GTG GCT GCT<br>Ala Gln Arg Val Ala Ala Gly Leu Ser Ser Thr Gly Pro Val Ala Ala<br>                310                  315                  320 | 816 |
| TTA ATT GCT TCT ACT GTT TCT CTT GCG ATT AGC CCA TTA GCA TTT GCC<br>Leu Ile Ala Ser Thr Val Ser Leu Ala Ile Ser Pro Leu Ala Phe Ala<br>               325                  330                 335 | 864 |
| GGT ATT GCC GAT AAA TTT AAT CAT GCA AAA AGT TTA GAG AGT TAT GCC<br>Gly Ile Ala Asp Lys Phe Asn His Ala Lys Ser Leu Glu Ser Tyr Ala<br>340                           345                   350 | 912 |
| GAA CGC TTT AAA AAA TTA GGC TAT GAC GGA GAT AAT TTA TTA GCA GAA<br>Glu Arg Phe Lys Lys Leu Gly Tyr Asp Gly Asp Asn Leu Leu Ala Glu<br>355                           360                   365 | 960 |
| TAT CAG CGG GGA ACA GGG ACT ATT GAT GCA TCG GTT ACT GCA ATT AAT<br>Tyr Gln Arg Gly Thr Gly Thr Ile Asp Ala Ser Val Thr Ala Ile Asn<br>370                           375                   380                  385 | 1008 |
| ACC GCA TTG GCC GCT ATT GCT GGT GGT GTG TCT GCT GCT GCA GCC GGC<br>Thr Ala Leu Ala Ala Ile Ala Gly Gly Val Ser Ala Ala Ala Ala Gly<br>                390                  395                  400 | 1056 |
| TCG GTT ATT GCT TCA CCG ATT GCC TTA TTA GTA TCT GGG ATT ACC GGT<br>Ser Val Ile Ala Ser Pro Ile Ala Leu Leu Val Ser Gly Ile Thr Gly<br>               405                  410                 415 | 1104 |
| GTA ATT TCT ACG ATT CTG CAA TAT TCT AAA CAA GCA ATG TTT GAG CAC<br>Val Ile Ser Thr Ile Leu Gln Tyr Ser Lys Gln Ala Met Phe Glu His<br>420                           425                   430 | 1152 |

```
GTT GCA AAT AAA ATT CAT AAC AAA ATT GTA GAA TGG GAA AAA AAT AAT        1200
Val Ala Asn Lys Ile His Asn Lys Ile Val Glu Trp Glu Lys Asn Asn
    435                 440                 445

CAC GGT AAG AAC TAC TTT GAA AAT GGT TAC GAT GCC CGT TAT CTT GCG        1248
His Gly Lys Asn Tyr Phe Glu Asn Gly Tyr Asp Ala Arg Tyr Leu Ala
450                 455                 460                 465

AAT TTA CAA GAT AAT ATG AAA TTC TTA CTG AAC TTA AAC AAA GAG TTA        1296
Asn Leu Gln Asp Asn Met Lys Phe Leu Leu Asn Leu Asn Lys Glu Leu
                470                 475                 480

CAG GCA GAA CGT GTC ATC GCT ATT ACT CAG CAG CAA TGG GAT AAC AAC        1344
Gln Ala Glu Arg Val Ile Ala Ile Thr Gln Gln Gln Trp Asp Asn Asn
            485                 490                 495

ATT GGT GAT TTA GCT GGT ATT AGC CGT TTA GGT GAA AAA GTC CTT AGT        1392
Ile Gly Asp Leu Ala Gly Ile Ser Arg Leu Gly Glu Lys Val Leu Ser
        500                 505                 510

GGT AAA GCC TAT GTG GAT GCG TTT GAA GAA GGC AAA CAC ATT AAA GCC        1440
Gly Lys Ala Tyr Val Asp Ala Phe Glu Glu Gly Lys His Ile Lys Ala
    515                 520                 525

GAT AAA TTA GTA CAG TTG GAT TCG GCA AAC GGT ATT ATT GAT GTG AGT        1488
Asp Lys Leu Val Gln Leu Asp Ser Ala Asn Gly Ile Ile Asp Val Ser
530                 535                 540                 545

AAT TCG GGT AAA GCG AAA ACT CAG CAT ATC TTA TTC AGA ACG CCA TTA        1536
Asn Ser Gly Lys Ala Lys Thr Gln His Ile Leu Phe Arg Thr Pro Leu
                550                 555                 560

TTG ACG CCG GGA ACA GAG CAT CGT GAA CGC GTA CAA ACA GGT AAA TAT        1584
Leu Thr Pro Gly Thr Glu His Arg Glu Arg Val Gln Thr Gly Lys Tyr
            565                 570                 575

GAA TAT ATT ACC AAG CTC AAT ATT AAC CGT GTA GAT AGC TGG AAA ATT        1632
Glu Tyr Ile Thr Lys Leu Asn Ile Asn Arg Val Asp Ser Trp Lys Ile
        580                 585                 590

ACA GAT GGT GCA GCA AGT TCT ACC TTT GAT TTA ACT AAC GTT GTT CAG        1680
Thr Asp Gly Ala Ala Ser Ser Thr Phe Asp Leu Thr Asn Val Val Gln
    595                 600                 605

CGT ATT GGT ATT GAA TTA GAC AAT GCT GGA AAT GTA ACT AAA ACC AAA        1728
Arg Ile Gly Ile Glu Leu Asp Asn Ala Gly Asn Val Thr Lys Thr Lys
610                 615                 620                 625

GAA ACA AAA ATT ATT GCC AAA CTT GGT GAA GGT GAT GAC AAC GTA TTT        1776
Glu Thr Lys Ile Ile Ala Lys Leu Gly Glu Gly Asp Asp Asn Val Phe
                630                 635                 640

GTT GGT TCT GGT ACG ACG GAA ATT GAT GGC GGT GAA GGT TAC GAC CGA        1824
Val Gly Ser Gly Thr Thr Glu Ile Asp Gly Gly Glu Gly Tyr Asp Arg
            645                 650                 655

GTT CAC TAT AGC CGT GGA AAC TAT GGT GCT TTA ACT ATT GAT GCA ACC        1872
Val His Tyr Ser Arg Gly Asn Tyr Gly Ala Leu Thr Ile Asp Ala Thr
        660                 665                 670

AAA GAG ACC GAG CAA GGT AGT TAT ACC GTA AAT CGT TTC GTA GAA ACC        1920
Lys Glu Thr Glu Gln Gly Ser Tyr Thr Val Asn Arg Phe Val Glu Thr
    675                 680                 685

GGT AAA GCA CTA CAC GAA GTG ACT TCA ACC CAT ACC GCA TTA GTG GGC        1968
Gly Lys Ala Leu His Glu Val Thr Ser Thr His Thr Ala Leu Val Gly
690                 695                 700                 705

AAC CGT GAA GAA AAA ATA GAA TAT CGT CAT AGC AAT AAC CAG CAC CAT        2016
Asn Arg Glu Glu Lys Ile Glu Tyr Arg His Ser Asn Asn Gln His His
                710                 715                 720

GCC GGT TAT TAC ACC AAA GAT ACC TTG AAA GCT GTT GAA GAA ATT ATC        2064
Ala Gly Tyr Tyr Thr Lys Asp Thr Leu Lys Ala Val Glu Glu Ile Ile
            725                 730                 735

GGT ACA TCA CAT AAC GAT ATC TTT AAA GGT AGT AAG TTC AAT GAT GCC        2112
Gly Thr Ser His Asn Asp Ile Phe Lys Gly Ser Lys Phe Asn Asp Ala
```

```
           740                745                750
TTT AAC GGT GGT GAT GGT GTC GAT ACT ATT GAC GGT AAC GAC GGC AAT    2160
Phe Asn Gly Gly Asp Gly Val Asp Thr Ile Asp Gly Asn Asp Gly Asn
        755                760                765

GAC CGC TTA TTT GGT GGT AAA GGC GAT GAT ATT CTC GAT GGT GGA AAT    2208
Asp Arg Leu Phe Gly Gly Lys Gly Asp Asp Ile Leu Asp Gly Gly Asn
770                775                780                785

GGT GAT GAT TTT ATC GAT GGC GGT AAA GGC AAC GAC CTA TTA CAC GGT    2256
Gly Asp Asp Phe Ile Asp Gly Gly Lys Gly Asn Asp Leu Leu His Gly
                790                795                800

GGC AAG GGC GAT GAT ATT TTC GTT CAC CGT AAA GGC GAT GGT AAT GAT    2304
Gly Lys Gly Asp Asp Ile Phe Val His Arg Lys Gly Asp Gly Asn Asp
            805                810                815

ATT ATT ACC GAT TCT GAC GGC AAT GAT AAA TTA TCA TTC TCT GAT TCG    2352
Ile Ile Thr Asp Ser Asp Gly Asn Asp Lys Leu Ser Phe Ser Asp Ser
        820                825                830

AAC TTA AAA GAT TTA ACA TTT GAA AAA GTT AAA CAT AAT CTT GTC ATC    2400
Asn Leu Lys Asp Leu Thr Phe Glu Lys Val Lys His Asn Leu Val Ile
    835                840                845

ACG AAT AGC AAA AAA GAG AAA GTG ACC ATT CAA AAC TGG TTC CGA GAG    2448
Thr Asn Ser Lys Lys Glu Lys Val Thr Ile Gln Asn Trp Phe Arg Glu
850                855                860                865

GCT GAT TTT GCT AAA GAA GTG CCT AAT TAT AAA GCA ACT AAA GAT GAG    2496
Ala Asp Phe Ala Lys Glu Val Pro Asn Tyr Lys Ala Thr Lys Asp Glu
                870                875                880

AAA ATC GAA GAA ATC ATC GGT CAA AAT GGC GAG CGG ATC ACC TCA AAG    2544
Lys Ile Glu Glu Ile Ile Gly Gln Asn Gly Glu Arg Ile Thr Ser Lys
            885                890                895

CAA GTT GAT GAT CTT ATC GCA AAA GGT AAC GGC AAA ATT ACC CAA GAT    2592
Gln Val Asp Asp Leu Ile Ala Lys Gly Asn Gly Lys Ile Thr Gln Asp
        900                905                910

GAG CTA TCA AAA GTT GTT GAT AAC TAT GAA TTG CTC AAA CAT AGC AAA    2640
Glu Leu Ser Lys Val Val Asp Asn Tyr Glu Leu Leu Lys His Ser Lys
    915                920                925

AAT GTG ACA AAC AGC TTA GAT AAG TTA ATC TCA TCT GTA AGT GCA TTT    2688
Asn Val Thr Asn Ser Leu Asp Lys Leu Ile Ser Ser Val Ser Ala Phe
930                935                940                945

ACC TCG TCT AAT GAT TCG AGA AAT GTA TTA GTG GCT CCA ACT TCA ATG    2736
Thr Ser Ser Asn Asp Ser Arg Asn Val Leu Val Ala Pro Thr Ser Met
                950                955                960

TTG GAT CAA AGT TTA TCT TCT CTT CAA TTT GCT AGG GGA TCC            2778
Leu Asp Gln Ser Leu Ser Ser Leu Gln Phe Ala Arg Gly Ser
            965                970                975

TAGCTAGCTA GCCATG                                                  2794

(2) INFORMATION FOR SEQ ID NO:6:

(i) SEQUENCE CHARACTERISTICS:
        (A) LENGTH: 926 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Thr Val Ile Asp Leu Ser Phe Pro Lys Thr Gly Ala Lys Lys
 1               5                  10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
```

```
                 35                   40                  45
Val Gln Arg Glu Glu Arg Asn Asn Ile Ala Thr Ala Gln Thr Ser Leu
             50                   55                  60
Gly Thr Ile Gln Thr Ala Ile Gly Leu Thr Glu Arg Gly Ile Val Leu
 65                   70                  75                  80
Ser Ala Pro Gln Ile Asp Lys Leu Leu Gln Lys Thr Lys Ala Gly Gln
                 85                   90                  95
Ala Leu Gly Ser Ala Glu Ser Ile Val Gln Asn Ala Asn Lys Ala Lys
                100                  105                 110
Thr Val Leu Ser Gly Ile Gln Ser Ile Leu Gly Ser Val Leu Ala Gly
                115                  120                 125
Met Asp Leu Asp Glu Ala Leu Gln Asn Asn Ser Asn Gln His Ala Leu
                130                  135                 140
Ala Lys Ala Gly Leu Glu Leu Thr Asn Ser Leu Ile Glu Asn Ile Ala
145                  150                  155                 160
Asn Ser Val Lys Thr Leu Asp Glu Phe Gly Glu Gln Ile Ser Gln Phe
                165                  170                 175
Gly Ser Lys Leu Gln Asn Ile Lys Gly Leu Gly Thr Leu Gly Asp Lys
                180                  185                 190
Leu Lys Asn Ile Gly Gly Leu Asp Lys Ala Gly Leu Gly Leu Asp Val
                195                  200                 205
Ile Ser Gly Leu Leu Ser Gly Ala Thr Ala Ala Leu Val Leu Ala Asp
210                  215                  220
Lys Asn Ala Ser Thr Ala Lys Lys Val Gly Ala Gly Phe Glu Leu Ala
225                  230                  235                 240
Asn Gln Val Val Gly Asn Ile Thr Lys Ala Val Ser Ser Tyr Ile Leu
                245                  250                 255
Ala Gln Arg Val Ala Ala Gly Leu Ser Ser Thr Gly Pro Val Ala Ala
                260                  265                 270
Leu Ile Ala Ser Thr Val Ser Leu Ala Ile Ser Pro Leu Ala Phe Ala
                275                  280                 285
Gly Ile Ala Asp Lys Phe Asn His Ala Lys Ser Leu Glu Ser Tyr Ala
                290                  295                 300
Glu Arg Phe Lys Lys Leu Gly Tyr Asp Gly Asp Asn Leu Leu Ala Glu
305                  310                  315                 320
Tyr Gln Arg Gly Thr Gly Thr Ile Asp Ala Ser Val Thr Ala Ile Asn
                325                  330                 335
Thr Ala Leu Ala Ala Ile Ala Gly Gly Val Ser Ala Ala Ala Gly
                340                  345                 350
Ser Val Ile Ala Ser Pro Ile Ala Leu Leu Val Ser Gly Ile Thr Gly
                355                  360                 365
Val Ile Ser Thr Ile Leu Gln Tyr Ser Lys Gln Ala Met Phe Glu His
                370                  375                 380
Val Ala Asn Lys Ile His Asn Lys Ile Val Glu Trp Glu Lys Asn Asn
385                  390                  395                 400
His Gly Lys Asn Tyr Phe Glu Asn Gly Tyr Asp Ala Arg Tyr Leu Ala
                405                  410                 415
Asn Leu Gln Asp Asn Met Lys Phe Leu Leu Asn Leu Asn Lys Glu Leu
                420                  425                 430
Gln Ala Glu Arg Val Ile Ala Ile Thr Gln Gln Trp Asp Asn Asn
                435                  440                 445
Ile Gly Asp Leu Ala Gly Ile Ser Arg Leu Gly Glu Lys Val Leu Ser
450                  455                  460
```

-continued

```
Gly Lys Ala Tyr Val Asp Ala Phe Glu Glu Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880
```

```
Asn Val Thr Asn Ser Leu Asp Lys Leu Ile Ser Ser Val Ser Ala Phe
            885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser
            915                 920                 925
```

(2) INFORMATION FOR SEQ ID NO:7:

(i) SEQUENCE CHARACTERISTICS:
        (A) LENGTH: 2934 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2931

(xi) SEQUENCE DESCRIPTION: SEQ ID NO:7:

```
ATG GCT ACT GTT ATA GAT CTA AGC TTC CCA AAA ACT GGG GCA AAA AAA    48
Met Ala Thr Val Ile Asp Leu Ser Phe Pro Lys Thr Gly Ala Lys Lys
            930                 935                 940

ATT ATC CTC TAT ATT CCC CAA AAT TAC CAA TAT GAT ACT GAA CAA GGT    96
Ile Ile Leu Tyr Ile Pro Gln Asn Tyr Gln Tyr Asp Thr Glu Gln Gly
            945                 950                 955

AAT GGT TTA CAG GAT TTA GTC AAA GCG GCC GAA GAG TTG GGG ATT GAG   144
Asn Gly Leu Gln Asp Leu Val Lys Ala Ala Glu Glu Leu Gly Ile Glu
            960                 965                 970

GTA CAA AGA GAA GAA CGC AAT AAT ATT GCA ACA GCT CAA ACC AGT TTA   192
Val Gln Arg Glu Glu Arg Asn Asn Ile Ala Thr Ala Gln Thr Ser Leu
975                 980                 985                 990

GGC ACG ATT CAA ACC GCT ATT GGC TTA ACT GAG CGT GGC ATT GTG TTA   240
Gly Thr Ile Gln Thr Ala Ile Gly Leu Thr Glu Arg Gly Ile Val Leu
                995                 1000                1005

TCC GCT CCA CAA ATT GAT AAA TTG CTA CAG AAA ACT AAA GCA GGC CAA   288
Ser Ala Pro Gln Ile Asp Lys Leu Leu Gln Lys Thr Lys Ala Gly Gln
                1010                1015                1020

GCA TTA GGT TCT GCC GAA AGC ATT GTA CAA AAT GCA AAT AAA GCC AAA   336
Ala Leu Gly Ser Ala Glu Ser Ile Val Gln Asn Ala Asn Lys Ala Lys
                1025                1030                1035

ACT GTA TTA TCT GGC ATT CAA TCT ATT TTA GGC TCA GTA TTG GCT GGA   384
Thr Val Leu Ser Gly Ile Gln Ser Ile Leu Gly Ser Val Leu Ala Gly
                1040                1045                1050

ATG GAT TTA GAT GAG GCC TTA CAG AAT AAC AGC AAC CAA CAT GCT CTT   432
Met Asp Leu Asp Glu Ala Leu Gln Asn Asn Ser Asn Gln His Ala Leu
1055                1060                1065                1070

GCT AAA GCT GGC TTG GAG CTA ACA AAT TCA TTA ATT GAA AAT ATT GCT   480
Ala Lys Ala Gly Leu Glu Leu Thr Asn Ser Leu Ile Glu Asn Ile Ala
                1075                1080                1085

AAT TCA GTA AAA ACA CTT GAC GAA TTT GGT GAG CAA ATT AGT CAA TTT   528
Asn Ser Val Lys Thr Leu Asp Glu Phe Gly Glu Gln Ile Ser Gln Phe
                1090                1095                1100

GGT TCA AAA CTA CAA AAT ATC AAA GGC TTA GGG ACT TTA GGA GAC AAA   576
Gly Ser Lys Leu Gln Asn Ile Lys Gly Leu Gly Thr Leu Gly Asp Lys
                1105                1110                1115

CTC AAA AAT ATC GGT GGA CTT GAT AAA GCT GGC CTT GGT TTA GAT GTT   624
Leu Lys Asn Ile Gly Gly Leu Asp Lys Ala Gly Leu Gly Leu Asp Val
                1120                1125                1130

ATC TCA GGG CTA TTA TCG GGC GCA ACA GCT GCA CTT GTA CTT GCA GAT   672
```

```
Ile Ser Gly Leu Leu Ser Gly Ala Thr Ala Ala Leu Val Leu Ala Asp
1135                1140                1145                1150

AAA AAT GCT TCA ACA GCT AAA AAA GTG GGT GCG GGT TTT GAA TTG GCA      720
Lys Asn Ala Ser Thr Ala Lys Lys Val Gly Ala Gly Phe Glu Leu Ala
                    1155                1160                1165

AAC CAA GTT GTT GGT AAT ATT ACC AAA GCC GTT TCT TCT TAC ATT TTA      768
Asn Gln Val Val Gly Asn Ile Thr Lys Ala Val Ser Ser Tyr Ile Leu
                1170                1175                1180

GCC CAA CGT GTT GCA GCA GGT TTA TCT TCA ACT GGG CCT GTG GCT GCT      816
Ala Gln Arg Val Ala Ala Gly Leu Ser Ser Thr Gly Pro Val Ala Ala
            1185                1190                1195

TTA ATT GCT TCT ACT GTT TCT CTT GCG ATT AGC CCA TTA GCA TTT GCC      864
Leu Ile Ala Ser Thr Val Ser Leu Ala Ile Ser Pro Leu Ala Phe Ala
        1200                1205                1210

GGT ATT GCC GAT AAA TTT AAT CAT GCA AAA AGT TTA GAG AGT TAT GCC      912
Gly Ile Ala Asp Lys Phe Asn His Ala Lys Ser Leu Glu Ser Tyr Ala
1215                1220                1225                1230

GAA CGC TTT AAA AAA TTA GGC TAT GAC GGA GAT AAT TTA TTA GCA GAA      960
Glu Arg Phe Lys Lys Leu Gly Tyr Asp Gly Asp Asn Leu Leu Ala Glu
                1235                1240                1245

TAT CAG CGG GGA ACA GGG ACT ATT GAT GCA TCG GTT ACT GCA ATT AAT     1008
Tyr Gln Arg Gly Thr Gly Thr Ile Asp Ala Ser Val Thr Ala Ile Asn
            1250                1255                1260

ACC GCA TTG GCC GCT ATT GCT GGT GGT GTG TCT GCT GCT GCA GCC GGC     1056
Thr Ala Leu Ala Ala Ile Ala Gly Gly Val Ser Ala Ala Ala Ala Gly
        1265                1270                1275

TCG GTT ATT GCT TCA CCG ATT GCC TTA TTA GTA TCT GGG ATT ACC GGT     1104
Ser Val Ile Ala Ser Pro Ile Ala Leu Leu Val Ser Gly Ile Thr Gly
    1280                1285                1290

GTA ATT TCT ACG ATT CTG CAA TAT TCT AAA CAA GCA ATG TTT GAG CAC     1152
Val Ile Ser Thr Ile Leu Gln Tyr Ser Lys Gln Ala Met Phe Glu His
1295                1300                1305                1310

GTT GCA AAT AAA ATT CAT AAC AAA ATT GTA GAA TGG GAA AAA AAT AAT     1200
Val Ala Asn Lys Ile His Asn Lys Ile Val Glu Trp Glu Lys Asn Asn
                1315                1320                1325

CAC GGT AAG AAC TAC TTT GAA AAT GGT TAC GAT GCC CGT TAT CTT GCG     1248
His Gly Lys Asn Tyr Phe Glu Asn Gly Tyr Asp Ala Arg Tyr Leu Ala
            1330                1335                1340

AAT TTA CAA GAT AAT ATG AAA TTC TTA CTG AAC TTA AAC AAA GAG TTA     1296
Asn Leu Gln Asp Asn Met Lys Phe Leu Leu Asn Leu Asn Lys Glu Leu
        1345                1350                1355

CAG GCA GAA CGT GTC ATC GCT ATT ACT CAG CAG CAA TGG GAT AAC AAC     1344
Gln Ala Glu Arg Val Ile Ala Ile Thr Gln Gln Gln Trp Asp Asn Asn
    1360                1365                1370

ATT GGT GAT TTA GCT GGT ATT AGC CGT TTA GGT GAA AAA GTC CTT AGT     1392
Ile Gly Asp Leu Ala Gly Ile Ser Arg Leu Gly Glu Lys Val Leu Ser
1375                1380                1385                1390

GGT AAA GCC TAT GTG GAT GCG TTT GAA GAA GGC AAA CAC ATT AAA GCC     1440
Gly Lys Ala Tyr Val Asp Ala Phe Glu Glu Gly Lys His Ile Lys Ala
                1395                1400                1405

GAT AAA TTA GTA CAG TTG GAT TCG GCA AAC GGT ATT ATT GAT GTG AGT     1488
Asp Lys Leu Val Gln Leu Asp Ser Ala Asn Gly Ile Ile Asp Val Ser
            1410                1415                1420

AAT TCG GGT AAA GCG AAA ACT CAG CAT ATC TTA TTC AGA ACG CCA TTA     1536
Asn Ser Gly Lys Ala Lys Thr Gln His Ile Leu Phe Arg Thr Pro Leu
        1425                1430                1435

TTG ACG CCG GGA ACA GAG CAT CGT GAA CGC GTA CAA ACA GGT AAA TAT     1584
Leu Thr Pro Gly Thr Glu His Arg Glu Arg Val Gln Thr Gly Lys Tyr
    1440                1445                1450
```

-continued

```
GAA TAT ATT ACC AAG CTC AAT ATT AAC CGT GTA GAT AGC TGG AAA ATT      1632
Glu Tyr Ile Thr Lys Leu Asn Ile Asn Arg Val Asp Ser Trp Lys Ile
1455                1460                1465                1470

ACA GAT GGT GCA GCA AGT TCT ACC TTT GAT TTA ACT AAC GTT GTT CAG      1680
Thr Asp Gly Ala Ala Ser Ser Thr Phe Asp Leu Thr Asn Val Val Gln
                1475                1480                1485

CGT ATT GGT ATT GAA TTA GAC AAT GCT GGA AAT GTA ACT AAA ACC AAA      1728
Arg Ile Gly Ile Glu Leu Asp Asn Ala Gly Asn Val Thr Lys Thr Lys
            1490                1495                1500

GAA ACA AAA ATT ATT GCC AAA CTT GGT GAA GGT GAT GAC AAC GTA TTT      1776
Glu Thr Lys Ile Ile Ala Lys Leu Gly Glu Gly Asp Asp Asn Val Phe
        1505                1510                1515

GTT GGT TCT GGT ACG ACG GAA ATT GAT GGC GGT GAA GGT TAC GAC CGA      1824
Val Gly Ser Gly Thr Thr Glu Ile Asp Gly Gly Glu Gly Tyr Asp Arg
    1520                1525                1530

GTT CAC TAT AGC CGT GGA AAC TAT GGT GCT TTA ACT ATT GAT GCA ACC      1872
Val His Tyr Ser Arg Gly Asn Tyr Gly Ala Leu Thr Ile Asp Ala Thr
1535                1540                1545                1550

AAA GAG ACC GAG CAA GGT AGT TAT ACC GTA AAT CGT TTC GTA GAA ACC      1920
Lys Glu Thr Glu Gln Gly Ser Tyr Thr Val Asn Arg Phe Val Glu Thr
                1555                1560                1565

GGT AAA GCA CTA CAC GAA GTG ACT TCA ACC CAT ACC GCA TTA GTG GGC      1968
Gly Lys Ala Leu His Glu Val Thr Ser Thr His Thr Ala Leu Val Gly
            1570                1575                1580

AAC CGT GAA GAA AAA ATA GAA TAT CGT CAT AGC AAT AAC CAG CAC CAT      2016
Asn Arg Glu Glu Lys Ile Glu Tyr Arg His Ser Asn Asn Gln His His
        1585                1590                1595

GCC GGT TAT TAC ACC AAA GAT ACC TTG AAA GCT GTT GAA GAA ATT ATC      2064
Ala Gly Tyr Tyr Thr Lys Asp Thr Leu Lys Ala Val Glu Glu Ile Ile
    1600                1605                1610

GGT ACA TCA CAT AAC GAT ATC TTT AAA GGT AGT AAG TTC AAT GAT GCC      2112
Gly Thr Ser His Asn Asp Ile Phe Lys Gly Ser Lys Phe Asn Asp Ala
1615                1620                1625                1630

TTT AAC GGT GGT GAT GGT GTC GAT ACT ATT GAC GGT AAC GAC GGC AAT      2160
Phe Asn Gly Gly Asp Gly Val Asp Thr Ile Asp Gly Asn Asp Gly Asn
                1635                1640                1645

GAC CGC TTA TTT GGT GGT AAA GGC GAT GAT ATT CTC GAT GGT GGA AAT      2208
Asp Arg Leu Phe Gly Gly Lys Gly Asp Asp Ile Leu Asp Gly Gly Asn
            1650                1655                1660

GGT GAT GAT TTT ATC GAT GGC GGT AAA GGC AAC GAC CTA TTA CAC GGT      2256
Gly Asp Asp Phe Ile Asp Gly Gly Lys Gly Asn Asp Leu Leu His Gly
        1665                1670                1675

GGC AAG GGC GAT GAT ATT TTC GTT CAC CGT AAA GGC GAT GGT AAT GAT      2304
Gly Lys Gly Asp Asp Ile Phe Val His Arg Lys Gly Asp Gly Asn Asp
    1680                1685                1690

ATT ATT ACC GAT TCT GAC GGC AAT GAT AAA TTA TCA TTC TCT GAT TCG      2352
Ile Ile Thr Asp Ser Asp Gly Asn Asp Lys Leu Ser Phe Ser Asp Ser
1695                1700                1705                1710

AAC TTA AAA GAT TTA ACA TTT GAA AAA GTT AAA CAT AAT CTT GTC ATC      2400
Asn Leu Lys Asp Leu Thr Phe Glu Lys Val Lys His Asn Leu Val Ile
                1715                1720                1725

ACG AAT AGC AAA AAA GAG AAA GTG ACC ATT CAA AAC TGG TTC CGA GAG      2448
Thr Asn Ser Lys Lys Glu Lys Val Thr Ile Gln Asn Trp Phe Arg Glu
            1730                1735                1740

GCT GAT TTT GCT AAA GAA GTG CCT AAT TAT AAA GCA ACT AAA GAT GAG      2496
Ala Asp Phe Ala Lys Glu Val Pro Asn Tyr Lys Ala Thr Lys Asp Glu
        1745                1750                1755

AAA ATC GAA GAA ATC ATC GGT CAA AAT GGC GAG CGG ATC ACC TCA AAG      2544
Lys Ile Glu Glu Ile Ile Gly Gln Asn Gly Glu Arg Ile Thr Ser Lys
    1760                1765                1770
```

```
CAA GTT GAT GAT CTT ATC GCA AAA GGT AAC GGC AAA ATT ACC CAA GAT        2592
Gln Val Asp Asp Leu Ile Ala Lys Gly Asn Gly Lys Ile Thr Gln Asp
1775                1780                1785                1790

GAG CTA TCA AAA GTT GTT GAT AAC TAT GAA TTG CTC AAA CAT AGC AAA        2640
Glu Leu Ser Lys Val Val Asp Asn Tyr Glu Leu Leu Lys His Ser Lys
                1795                1800                1805

AAT GTG ACA AAC AGC TTA GAT AAG TTA ATC TCA TCT GTA AGT GCA TTT        2688
Asn Val Thr Asn Ser Leu Asp Lys Leu Ile Ser Ser Val Ser Ala Phe
            1810                1815                1820

ACC TCG TCT AAT GAT TCG AGA AAT GTA TTA GTG GCT CCA ACT TCA ATG        2736
Thr Ser Ser Asn Asp Ser Arg Asn Val Leu Val Ala Pro Thr Ser Met
        1825                1830                1835

TTG GAT CAA AGT TTA TCT TCT CTT CAA TTT GCT AGG GGA TCT CAG CAT        2784
Leu Asp Gln Ser Leu Ser Ser Leu Gln Phe Ala Arg Gly Ser Gln His
    1840                1845                1850

TGG AGC TAC GGC CTG CGC CCT GGC AGC GGT TCT CAA GAT TGG AGC TAC        2832
Trp Ser Tyr Gly Leu Arg Pro Gly Ser Gly Ser Gln Asp Trp Ser Tyr
1855                1860                1865                1870

GGC CTG CGT CCG GGT GGC TCT AGC CAG CAT TGG AGC TAC GGC CTG CGC        2880
Gly Leu Arg Pro Gly Gly Ser Ser Gln His Trp Ser Tyr Gly Leu Arg
                1875                1880                1885

CCT GGC AGC GGT AGC CAA GAT TGG AGC TAC GGC CTG CGT CCG GGT GGA        2928
Pro Gly Ser Gly Ser Gln Asp Trp Ser Tyr Gly Leu Arg Pro Gly Gly
            1890                1895                1900

TCC TAG                                                                2934
Ser (2) INFORMATION FOR SEQ ID NO:8:

(i) SEQUENCE CHARACTERISTICS:
        (A) LENGTH: 977 amino acids
        (B) TYPE: amino acid
        (D) TOPOLOGY: linear (ii) MOLECULE TYPE: protein (xi) SEQUENCE DESCRIPTION: SEQ ID NO:8:

Met Ala Thr Val Ile Asp Leu Ser Phe Pro Lys Thr Gly Ala Lys Lys
 1               5                  10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
```

-continued

```
                165                 170                 175
Gly Ser Lys Leu Gln Asn Ile Lys Gly Leu Gly Thr Leu Gly Asp Lys
            180                 185                 190
Leu Lys Asn Ile Gly Gly Leu Asp Lys Ala Gly Leu Gly Leu Asp Val
        195                 200                 205
Ile Ser Gly Leu Leu Ser Gly Ala Thr Ala Ala Leu Val Leu Ala Asp
    210                 215                 220
Lys Asn Ala Ser Thr Ala Lys Lys Val Gly Ala Gly Phe Glu Leu Ala
225                 230                 235                 240
Asn Gln Val Val Gly Asn Ile Thr Lys Ala Val Ser Ser Tyr Ile Leu
                245                 250                 255
Ala Gln Arg Val Ala Ala Gly Leu Ser Ser Thr Gly Pro Val Ala Ala
            260                 265                 270
Leu Ile Ala Ser Thr Val Ser Leu Ala Ile Ser Pro Leu Ala Phe Ala
        275                 280                 285
Gly Ile Ala Asp Lys Phe Asn His Ala Lys Ser Leu Glu Ser Tyr Ala
    290                 295                 300
Glu Arg Phe Lys Lys Leu Gly Tyr Asp Gly Asp Asn Leu Leu Ala Glu
305                 310                 315                 320
Tyr Gln Arg Gly Thr Gly Thr Ile Asp Ala Ser Val Thr Ala Ile Asn
                325                 330                 335
Thr Ala Leu Ala Ala Ile Ala Gly Gly Val Ser Ala Ala Ala Ala Gly
            340                 345                 350
Ser Val Ile Ala Ser Pro Ile Ala Leu Leu Val Ser Gly Ile Thr Gly
        355                 360                 365
Val Ile Ser Thr Ile Leu Gln Tyr Ser Lys Gln Ala Met Phe Glu His
    370                 375                 380
Val Ala Asn Lys Ile His Asn Lys Ile Val Glu Trp Glu Lys Asn Asn
385                 390                 395                 400
His Gly Lys Asn Tyr Phe Glu Asn Gly Tyr Asp Ala Arg Tyr Leu Ala
                405                 410                 415
Asn Leu Gln Asp Asn Met Lys Phe Leu Leu Asn Leu Asn Lys Glu Leu
            420                 425                 430
Gln Ala Glu Arg Val Ile Ala Ile Thr Gln Gln Trp Asp Asn Asn
        435                 440                 445
Ile Gly Asp Leu Ala Gly Ile Ser Arg Leu Gly Glu Lys Val Leu Ser
    450                 455                 460
Gly Lys Ala Tyr Val Asp Ala Phe Glu Glu Gly Lys His Ile Lys Ala
465                 470                 475                 480
Asp Lys Leu Val Gln Leu Asp Ser Ala Asn Gly Ile Ile Asp Val Ser
                485                 490                 495
Asn Ser Gly Lys Ala Lys Thr Gln His Ile Leu Phe Arg Thr Pro Leu
            500                 505                 510
Leu Thr Pro Gly Thr Glu His Arg Glu Arg Val Gln Thr Gly Lys Tyr
        515                 520                 525
Glu Tyr Ile Thr Lys Leu Asn Ile Asn Arg Val Asp Ser Trp Lys Ile
    530                 535                 540
Thr Asp Gly Ala Ala Ser Ser Thr Phe Asp Leu Thr Asn Val Val Gln
545                 550                 555                 560
Arg Ile Gly Ile Glu Leu Asp Asn Ala Gly Asn Val Thr Lys Thr Lys
                565                 570                 575
Glu Thr Lys Ile Ile Ala Lys Leu Gly Glu Gly Asp Asp Asn Val Phe
            580                 585                 590
```

```
Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
        610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                    645                 650                 655

Asn Arg Glu Glu Lys Ile Glu Tyr Arg His Ser Asn Asn Gln His His
                660                 665                 670

Ala Gly Tyr Tyr Thr Lys Asp Thr Leu Lys Ala Val Glu Glu Ile Ile
                675                 680                 685

Gly Thr Ser His Asn Asp Ile Phe Lys Gly Ser Lys Phe Asn Asp Ala
        690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                    725                 730                 735

Gly Asp Asp Phe Ile Asp Gly Gly Lys Gly Asn Asp Leu Leu His Gly
                740                 745                 750

Gly Lys Gly Asp Asp Ile Phe Val His Arg Lys Gly Asp Gly Asn Asp
                755                 760                 765

Ile Ile Thr Asp Ser Asp Gly Asn Asp Lys Leu Ser Phe Ser Asp Ser
        770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                    805                 810                 815

Ala Asp Phe Ala Lys Glu Val Pro Asn Tyr Lys Ala Thr Lys Asp Glu
                820                 825                 830

Lys Ile Glu Glu Ile Ile Gly Gln Asn Gly Glu Arg Ile Thr Ser Lys
                835                 840                 845

Gln Val Asp Asp Leu Ile Ala Lys Gly Asn Gly Lys Ile Thr Gln Asp
        850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                    885                 890                 895

Thr Ser Ser Asn Asp Ser Arg Asn Val Leu Val Ala Pro Thr Ser Met
                900                 905                 910

Leu Asp Gln Ser Leu Ser Ser Leu Gln Phe Ala Arg Gly Ser Gln His
                915                 920                 925

Trp Ser Tyr Gly Leu Arg Pro Gly Ser Gly Ser Gln Asp Trp Ser Tyr
        930                 935                 940

Gly Leu Arg Pro Gly Gly Ser Ser Gln His Trp Ser Tyr Gly Leu Arg
945                 950                 955                 960

Pro Gly Ser Gly Ser Gln Asp Trp Ser Tyr Gly Leu Arg Pro Gly Gly
                    965                 970                 975

Ser
```

(2) INFORMATION FOR SEQ ID NO:9:

(i) SEQUENCE CHARACTERISTICS:

(A) LENGTH: 1635 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..1632

(xi) SEQUENCE DESCRIPTION: SEQ ID NO:9:

```
ATG GCT ACT GTT ATA GAT CTA AGC TTC CCA AAA ACT GGG GCA AAA AAA        48
Met Ala Thr Val Ile Asp Leu Ser Phe Pro Lys Thr Gly Ala Lys Lys
            980                 985                 990

ATT ATC CTC TAT ATT CCC CAA AAT TAC CAA TAT GAT ACT GAA CAA GGT        96
Ile Ile Leu Tyr Ile Pro Gln Asn Tyr Gln Tyr Asp Thr Glu Gln Gly
995                 1000                1005

AAT GGT TTA CAG GAT TTA GTC AAA GCG GCC GAA GAG TTG GGG ATT GAG       144
Asn Gly Leu Gln Asp Leu Val Lys Ala Ala Glu Glu Leu Gly Ile Glu
1010                1015                1020                1025

GTA CAA AGA GAA GAA CGC AAT AAT ATT GCA ACA GCT CAA ACC AGT TTA       192
Val Gln Arg Glu Glu Arg Asn Asn Ile Ala Thr Ala Gln Thr Ser Leu
            1030                1035                1040

GGC ACG ATT CAA ACC GCT ATT GGC TTA ACT GAG CGT GGC ATT GTG TTA       240
Gly Thr Ile Gln Thr Ala Ile Gly Leu Thr Glu Arg Gly Ile Val Leu
            1045                1050                1055

TCC GCT CCA CAA ATT GAT AAA TTG CTA CAG AAA ACT AAA GCA GGC CAA       288
Ser Ala Pro Gln Ile Asp Lys Leu Leu Gln Lys Thr Lys Ala Gly Gln
            1060                1065                1070

GCA TTA GGT TCT GCC GAA AGC ATT GTA CAA AAT GCA AAT AAA GCC AAA       336
Ala Leu Gly Ser Ala Glu Ser Ile Val Gln Asn Ala Asn Lys Ala Lys
            1075                1080                1085

ACT GTA TTA TCT GGC ATT CAA TCT ATT TTA GGC TCA GTA TTG GCT GGA       384
Thr Val Leu Ser Gly Ile Gln Ser Ile Leu Gly Ser Val Leu Ala Gly
1090                1095                1100                1105

ATG GAT TTA GAT GAG GCC TTA CAG AAT AAC AGC AAC CAA CAT GCT CTT       432
Met Asp Leu Asp Glu Ala Leu Gln Asn Asn Ser Asn Gln His Ala Leu
            1110                1115                1120

GCT AAA GCT GGC TTG GAG CTA ACA AAT TCA TTA ATT GAA AAT ATT GCT       480
Ala Lys Ala Gly Leu Glu Leu Thr Asn Ser Leu Ile Glu Asn Ile Ala
            1125                1130                1135

AAT TCA GTA AAA ACA CTT GAC GAA TTT GGT GAG CAA ATT AGT CAA TTT       528
Asn Ser Val Lys Thr Leu Asp Glu Phe Gly Glu Gln Ile Ser Gln Phe
            1140                1145                1150

GGT TCA AAA CTA CAA AAT ATC AAA GGC TTA GGG ACT TTA GGA GAC AAA       576
Gly Ser Lys Leu Gln Asn Ile Lys Gly Leu Gly Thr Leu Gly Asp Lys
            1155                1160                1165

CTC AAA AAT ATC GGT GGA CTT GAT AAA GCT GGC CTT GGT TTA GAT GTT       624
Leu Lys Asn Ile Gly Gly Leu Asp Lys Ala Gly Leu Gly Leu Asp Val
1170                1175                1180                1185

ATC TCA GGG CTA TTA TCG GGC GCA ACA GCT GCA CTT GTA CTT GCA GAT       672
Ile Ser Gly Leu Leu Ser Gly Ala Thr Ala Ala Leu Val Leu Ala Asp
            1190                1195                1200

AAA AAT GCT TCA ACA GCT AAA AAA GTG GGT GCG GGT TTT GAA TTG GCA       720
Lys Asn Ala Ser Thr Ala Lys Lys Val Gly Ala Gly Phe Glu Leu Ala
            1205                1210                1215

AAC CAA GTT GTT GGT AAT ATT ACC AAA GCC GTT TCT TCT TAC ATT TTA       768
Asn Gln Val Val Gly Asn Ile Thr Lys Ala Val Ser Ser Tyr Ile Leu
            1220                1225                1230

GCC CAA CGT GTT GCA GCA GGT TTA TCT TCA ACT GGG CCT GTG GCT GCT       816
Ala Gln Arg Val Ala Ala Gly Leu Ser Ser Thr Gly Pro Val Ala Ala
```

```
                    1235                1240                1245
TTA ATT GCT TCT ACT GTT TCT CTT GCG ATT AGC CCA TTA GCA TTT GCC        864
Leu Ile Ala Ser Thr Val Ser Leu Ala Ile Ser Pro Leu Ala Phe Ala
1250                1255                1260                1265

GGT ATT GCC GAT AAA TTT AAT CAT GCA AAA AGT TTA GAG AGT TAT GCC        912
Gly Ile Ala Asp Lys Phe Asn His Ala Lys Ser Leu Glu Ser Tyr Ala
                1270                1275                1280

GAA CGC TTT AAA AAA TTA GGC TAT GAC GGA GAT AAT TTA TTA GCA GAA        960
Glu Arg Phe Lys Lys Leu Gly Tyr Asp Gly Asp Asn Leu Leu Ala Glu
            1285                1290                1295

TAT CAG CGG GGA ACA GGG ACT ATT GAT GCA TCG GTT ACT GCA ATT AAT       1008
Tyr Gln Arg Gly Thr Gly Thr Ile Asp Ala Ser Val Thr Ala Ile Asn
        1300                1305                1310

ACC GCA TTG GCC GCT ATT GCT GGT GGT GTG TCT GCT GCT GCA GCC AAC       1056
Thr Ala Leu Ala Ala Ile Ala Gly Gly Val Ser Ala Ala Ala Ala Asn
    1315                1320                1325

TTA AAA GAT TTA ACA TTT GAA AAA GTT AAA CAT AAT CTT GTC ATC ACG       1104
Leu Lys Asp Leu Thr Phe Glu Lys Val Lys His Asn Leu Val Ile Thr
1330                1335                1340                1345

AAT AGC AAA AAA GAG AAA GTG ACC ATT CAA AAC TGG TTC CGA GAG GCT       1152
Asn Ser Lys Lys Glu Lys Val Thr Ile Gln Asn Trp Phe Arg Glu Ala
                1350                1355                1360

GAT TTT GCT AAA GAA GTG CCT AAT TAT AAA GCA ACT AAA GAT GAG AAA       1200
Asp Phe Ala Lys Glu Val Pro Asn Tyr Lys Ala Thr Lys Asp Glu Lys
            1365                1370                1375

ATC GAA GAA ATC ATC GGT CAA AAT GGC GAG CGG ATC ACC TCA AAG CAA       1248
Ile Glu Glu Ile Ile Gly Gln Asn Gly Glu Arg Ile Thr Ser Lys Gln
        1380                1385                1390

GTT GAT GAT CTT ATC GCA AAA GGT AAC GGC AAA ATT ACC CAA GAT GAG       1296
Val Asp Asp Leu Ile Ala Lys Gly Asn Gly Lys Ile Thr Gln Asp Glu
    1395                1400                1405

CTA TCA AAA GTT GTT GAT AAC TAT GAA TTG CTC AAA CAT AGC AAA AAT       1344
Leu Ser Lys Val Val Asp Asn Tyr Glu Leu Leu Lys His Ser Lys Asn
1410                1415                1420                1425

GTG ACA AAC AGC TTA GAT AAG TTA ATC TCA TCT GTA AGT GCA TTT ACC       1392
Val Thr Asn Ser Leu Asp Lys Leu Ile Ser Ser Val Ser Ala Phe Thr
                1430                1435                1440

TCG TCT AAT GAT TCG AGA AAT GTA TTA GTG GCT CCA ACT TCA ATG TTG       1440
Ser Ser Asn Asp Ser Arg Asn Val Leu Val Ala Pro Thr Ser Met Leu
            1445                1450                1455

GAT CAA AGT TTA TCT TCT CTT CAA TTT GCT AGG GGA TCT CAG CAT TGG       1488
Asp Gln Ser Leu Ser Ser Leu Gln Phe Ala Arg Gly Ser Gln His Trp
        1460                1465                1470

AGC TAC GGC CTG CGC CCT GGC AGC GGT TCT CAA GAT TGG AGC TAC GGC       1536
Ser Tyr Gly Leu Arg Pro Gly Ser Gly Ser Gln Asp Trp Ser Tyr Gly
    1475                1480                1485

CTG CGT CCG GGT GGC TCT AGC CAG CAT TGG AGC TAC GGC CTG CGC CCT       1584
Leu Arg Pro Gly Gly Ser Ser Gln His Trp Ser Tyr Gly Leu Arg Pro
1490                1495                1500                1505

GGC AGC GGT AGC CAA GAT TGG AGC TAC GGC CTG CGT CCG GGT GGA TCC       1632
Gly Ser Gly Ser Gln Asp Trp Ser Tyr Gly Leu Arg Pro Gly Gly Ser
                1510                1515                1520

TAG                                                                    1635
```

(2) INFORMATION FOR SEQ ID NO:10:

(i) SEQUENCE CHARACTERISTICS:
        (A) LENGTH: 544 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Thr Val Ile Asp Leu Ser Phe Pro Lys Thr Gly Ala Lys Lys
  1               5                  10                  15

Ile Ile Leu Tyr Ile Pro Gln Asn Tyr Gln Tyr Asp Thr Glu Gln Gly
                 20                  25                  30

Asn Gly Leu Gln Asp Leu Val Lys Ala Ala Glu Glu Leu Gly Ile Glu
             35                  40                  45

Val Gln Arg Glu Glu Arg Asn Asn Ile Ala Thr Ala Gln Thr Ser Leu
         50                  55                  60

Gly Thr Ile Gln Thr Ala Ile Gly Leu Thr Glu Arg Gly Ile Val Leu
 65                  70                  75                  80

Ser Ala Pro Gln Ile Asp Lys Leu Leu Gln Lys Thr Lys Ala Gly Gln
                 85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Asn
            340                 345                 350

Leu Lys Asp Leu Thr Phe Glu Lys Val Lys His Asn Leu Val Ile Thr
        355                 360                 365

Asn Ser Lys Lys Glu Lys Val Thr Ile Gln Asn Trp Phe Arg Glu Ala
    370                 375                 380

Asp Phe Ala Lys Glu Val Pro Asn Tyr Lys Ala Thr Lys Asp Glu Lys
385                 390                 395                 400
```

Ile Glu Glu Ile Ile Gly Gln Asn Gly Glu Arg Ile Thr Ser Lys Gln
                405                 410                 415

Val Asp Asp Leu Ile Ala Lys Gly Asn Gly Lys Ile Thr Gln Asp Glu
            420                 425                 430

Leu Ser Lys Val Val Asp Asn Tyr Glu Leu Leu Lys His Ser Lys Asn
        435                 440                 445

Val Thr Asn Ser Leu Asp Lys Leu Ile Ser Ser Val Ser Ala Phe Thr
    450                 455                 460

Ser Ser Asn Asp Ser Arg Asn Val Leu Val Ala Pro Thr Ser Met Leu
465                 470                 475                 480

Asp Gln Ser Leu Ser Leu Gln Phe Ala Arg Gly Ser Gln His Trp
                485                 490                 495

Ser Tyr Gly Leu Arg Pro Gly Ser Gly Ser Gln Asp Trp Ser Tyr Gly
            500                 505                 510

Leu Arg Pro Gly Gly Ser Ser Gln His Trp Ser Tyr Gly Leu Arg Pro
        515                 520                 525

Gly Ser Gly Ser Gln Asp Trp Ser Tyr Gly Leu Arg Pro Gly Gly Ser
    530                 535                 540

(2) INFORMATION FOR SEQ ID NO:11:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..42

(xi) SEQUENCE DESCRIPTION: SEQ ID NO:11:

GCT GCA GCC GGC TCG GTT ATT TTC TCT GAT TCG AAC TTA AAA          42
Ala Ala Ala Gly Ser Val Ile Phe Ser Asp Ser Asn Leu Lys
545                 550                 555

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:12:

Ala Ala Ala Gly Ser Val Ile Phe Ser Asp Ser Asn Leu Lys
 1               5                  10

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..18

(xi) SEQUENCE DESCRIPTION: SEQ ID NO:13:

```
GCT GCA GCC AAC TTA AAA                                               18
Ala Ala Ala Asn Leu Lys
 15              20
```

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:14:

```
Ala Ala Ala Asn Leu Lys
 1           5
```

(2) INFORMATION FOR SEQ ID NO:15:

(i) SEQUENCE CHARACTERISTICS:
        (A) LENGTH: 2102 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..2085, 2089..2100)

(xi) SEQUENCE DESCRIPTION: SEQ ID NO:15:

```
ATG GCT ACT GTT ATA GAT CGA TCT CAG CAT TGG AGC TAC GGC CTG CGC       48
Met Ala Thr Val Ile Asp Arg Ser Gln His Trp Ser Tyr Gly Leu Arg
 1               5                  10                  15

CCT GGC AGC GGT TCT CAA GAT TGG AGC TAC GGC CTG CGT CCG GGT GGC       96
Pro Gly Ser Gly Ser Gln Asp Trp Ser Tyr Gly Leu Arg Pro Gly Gly
             20                  25                  30

TCT AGC CAG CAT TGG AGC TAC GGC CTG CGC CCT GGC AGC GGT AGC CAA      144
Ser Ser Gln His Trp Ser Tyr Gly Leu Arg Pro Gly Ser Gly Ser Gln
         35                  40                  45

GAT TGG AGC TAC GGC CTG CGT CCG GGT GGA TCT CAG CAT TGG AGC TAC      192
Asp Trp Ser Tyr Gly Leu Arg Pro Gly Gly Ser Gln His Trp Ser Tyr
     50                  55                  60

GGC CTG CGC CCT GGC AGC GGT TCT CAA GAT TGG AGC TAC GGC CTG CGT      240
Gly Leu Arg Pro Gly Ser Gly Ser Gln Asp Trp Ser Tyr Gly Leu Arg
 65                  70                  75                  80

CCG GGT GGC TCT AGC CAG CAT TGG AGC TAC GGC CTG CGC CCT GGC AGC      288
Pro Gly Gly Ser Ser Gln His Trp Ser Tyr Gly Leu Arg Pro Gly Ser
                 85                  90                  95

GGT AGC CAA GAT TGG AGC TAC GGC CTG CGT CCG GGT GGA TCT AGC TTC      336
Gly Ser Gln Asp Trp Ser Tyr Gly Leu Arg Pro Gly Gly Ser Ser Phe
            100                 105                 110

CCA AAA ACT GGG GCA AAA AAA ATT ATC CTC TAT ATT CCC CAA AAT TAC      384
Pro Lys Thr Gly Ala Lys Lys Ile Ile Leu Tyr Ile Pro Gln Asn Tyr
        115                 120                 125

CAA TAT GAT ACT GAA CAA GGT AAT GGT TTA CAG GAT TTA GTC AAA GCG      432
Gln Tyr Asp Thr Glu Gln Gly Asn Gly Leu Gln Asp Leu Val Lys Ala
    130                 135                 140

GCC GAA GAG TTG GGG ATT GAG GTA CAA AGA GAA GAA CGC AAT AAT ATT      480
Ala Glu Glu Leu Gly Ile Glu Val Gln Arg Glu Glu Arg Asn Asn Ile
145                 150                 155                 160

GCA ACA GCT CAA ACC AGT TTA GGC ACG ATT CAA ACC GCT ATT GGC TTA      528
```

```
Ala Thr Ala Gln Thr Ser Leu Gly Thr Ile Gln Thr Ala Ile Gly Leu
            165                 170                 175

ACT GAG CGT GGC ATT GTG TTA TCC GCT CCA CAA ATT GAT AAA TTG CTA       576
Thr Glu Arg Gly Ile Val Leu Ser Ala Pro Gln Ile Asp Lys Leu Leu
            180                 185                 190

CAG AAA ACT AAA GCA GGC CAA GCA TTA GGT TCT GCC GAA AGC ATT GTA       624
Gln Lys Thr Lys Ala Gly Gln Ala Leu Gly Ser Ala Glu Ser Ile Val
            195                 200                 205

CAA AAT GCA AAT AAA GCC AAA ACT GTA TTA TCT GGC ATT CAA TCT ATT       672
Gln Asn Ala Asn Lys Ala Lys Thr Val Leu Ser Gly Ile Gln Ser Ile
210                 215                 220

TTA GGC TCA GTA TTG GCT GGA ATG GAT TTA GAT GAG GCC TTA CAG AAT       720
Leu Gly Ser Val Leu Ala Gly Met Asp Leu Asp Glu Ala Leu Gln Asn
225                 230                 235                 240

AAC AGC AAC CAA CAT GCT CTT GCT AAA GCT GGC TTG GAG CTA ACA AAT       768
Asn Ser Asn Gln His Ala Leu Ala Lys Ala Gly Leu Glu Leu Thr Asn
            245                 250                 255

TCA TTA ATT GAA AAT ATT GCT AAT TCA GTA AAA ACA CTT GAC GAA TTT       816
Ser Leu Ile Glu Asn Ile Ala Asn Ser Val Lys Thr Leu Asp Glu Phe
            260                 265                 270

GGT GAG CAA ATT AGT CAA TTT GGT TCA AAA CTA CAA AAT ATC AAA GGC       864
Gly Glu Gln Ile Ser Gln Phe Gly Ser Lys Leu Gln Asn Ile Lys Gly
            275                 280                 285

TTA GGG ACT TTA GGA GAC AAA CTC AAA AAT ATC GGT GGA CTT GAT AAA       912
Leu Gly Thr Leu Gly Asp Lys Leu Lys Asn Ile Gly Gly Leu Asp Lys
            290                 295                 300

GCT GGC CTT GGT TTA GAT GTT ATC TCA GGG CTA TTA TCG GGC GCA ACA       960
Ala Gly Leu Gly Leu Asp Val Ile Ser Gly Leu Leu Ser Gly Ala Thr
305                 310                 315                 320

GCT GCA CTT GTA CTT GCA GAT AAA AAT GCT TCA ACA GCT AAA AAA GTG      1008
Ala Ala Leu Val Leu Ala Asp Lys Asn Ala Ser Thr Ala Lys Lys Val
            325                 330                 335

GGT GCG GGT TTT GAA TTG GCA AAC CAA GTT GTT GGT AAT ATT ACC AAA      1056
Gly Ala Gly Phe Glu Leu Ala Asn Gln Val Val Gly Asn Ile Thr Lys
            340                 345                 350

GCC GTT TCT TCT TAC ATT TTA GCC CAA CGT GTT GCA GCA GGT TTA TCT      1104
Ala Val Ser Ser Tyr Ile Leu Ala Gln Arg Val Ala Ala Gly Leu Ser
            355                 360                 365

TCA ACT GGG CCT GTG GCT GCT TTA ATT GCT TCT ACT GTT TCT CTT GCG      1152
Ser Thr Gly Pro Val Ala Ala Leu Ile Ala Ser Thr Val Ser Leu Ala
            370                 375                 380

ATT AGC CCA TTA GCA TTT GCC GGT ATT GCC GAT AAA TTT AAT CAT GCA      1200
Ile Ser Pro Leu Ala Phe Ala Gly Ile Ala Asp Lys Phe Asn His Ala
385                 390                 395                 400

AAA AGT TTA GAG AGT TAT GCC GAA CGC TTT AAA AAA TTA GGC TAT GAC      1248
Lys Ser Leu Glu Ser Tyr Ala Glu Arg Phe Lys Lys Leu Gly Tyr Asp
            405                 410                 415

GGA GAT AAT TTA TTA GCA GAA TAT CAG CGG GGA ACA GGG ACT ATT GAT      1296
Gly Asp Asn Leu Leu Ala Glu Tyr Gln Arg Gly Thr Gly Thr Ile Asp
            420                 425                 430

GCA TCG GTT ACT GCA ATT AAT ACC GCA TTG GCC GCT ATT GCT GGT GGT      1344
Ala Ser Val Thr Ala Ile Asn Thr Ala Leu Ala Ala Ile Ala Gly Gly
            435                 440                 445

GTG TCT GCT GCT GCA GCC GAT TTA ACA TTT GAA AAA GTT AAA CAT AAT      1392
Val Ser Ala Ala Ala Ala Asp Leu Thr Phe Glu Lys Val Lys His Asn
450                 455                 460

CTT GTC ATC ACG AAT AGC AAA AAA GAG AAA GTG ACC ATT CAA AAC TGG      1440
Leu Val Ile Thr Asn Ser Lys Lys Glu Lys Val Thr Ile Gln Asn Trp
465                 470                 475                 480
```

```
TTC CGA GAG GCT GAT TTT GCT AAA GAA GTG CCT AAT TAT AAA GCA ACT      1488
Phe Arg Glu Ala Asp Phe Ala Lys Glu Val Pro Asn Tyr Lys Ala Thr
                485                 490                 495

AAA GAT GAG AAA ATC GAA GAA ATC ATC GGT CAA AAT GGC GAG CGG ATC      1536
Lys Asp Glu Lys Ile Glu Glu Ile Ile Gly Gln Asn Gly Glu Arg Ile
                500                 505                 510

ACC TCA AAG CAA GTT GAT GAT CTT ATC GCA AAA GGT AAC GGC AAA ATT      1584
Thr Ser Lys Gln Val Asp Asp Leu Ile Ala Lys Gly Asn Gly Lys Ile
                515                 520                 525

ACC CAA GAT GAG CTA TCA AAA GTT GTT GAT AAC TAT GAA TTG CTC AAA      1632
Thr Gln Asp Glu Leu Ser Lys Val Val Asp Asn Tyr Glu Leu Leu Lys
            530                 535                 540

CAT AGC AAA AAT GTG ACA AAC AGC TTA GAT AAG TTA ATC TCA TCT GTA      1680
His Ser Lys Asn Val Thr Asn Ser Leu Asp Lys Leu Ile Ser Ser Val
545                 550                 555                 560

AGT GCA TTT ACC TCG TCT AAT GAT TCG AGA AAT GTA TTA GTG GCT CCA      1728
Ser Ala Phe Thr Ser Ser Asn Asp Ser Arg Asn Val Leu Val Ala Pro
                565                 570                 575

ACT TCA ATG TTG GAT CAA AGT TTA TCT TCT CTT CAA TTT GCT AGG GGA      1776
Thr Ser Met Leu Asp Gln Ser Leu Ser Ser Leu Gln Phe Ala Arg Gly
            580                 585                 590

TCT CAG CAT TGG AGC TAC GGC CTG CGC CCT GGC AGC GGT TCT CAA GAT      1824
Ser Gln His Trp Ser Tyr Gly Leu Arg Pro Gly Ser Gly Ser Gln Asp
            595                 600                 605

TGG AGC TAC GGC CTG CGT CCG GGT GGC TCT AGC CAG CAT TGG AGC TAC      1872
Trp Ser Tyr Gly Leu Arg Pro Gly Gly Ser Ser Gln His Trp Ser Tyr
            610                 615                 620

GGC CTG CGC CCT GGC AGC GGT AGC CAA GAT TGG AGC TAC GGC CTG CGT      1920
Gly Leu Arg Pro Gly Ser Gly Ser Gln Asp Trp Ser Tyr Gly Leu Arg
625                 630                 635                 640

CCG GGT GGA TCT CAG CAT TGG AGC TAC GGC CTG CGC CCT GGC AGC GGT      1968
Pro Gly Gly Ser Gln His Trp Ser Tyr Gly Leu Arg Pro Gly Ser Gly
                645                 650                 655

TCT CAA GAT TGG AGC TAC GGC CTG CGT CCG GGT GGC TCT AGC CAG CAT      2016
Ser Gln Asp Trp Ser Tyr Gly Leu Arg Pro Gly Gly Ser Ser Gln His
            660                 665                 670

TGG AGC TAC GGC CTG CGC CCT GGC AGC GGT AGC CAA GAT TGG AGC TAC      2064
Trp Ser Tyr Gly Leu Arg Pro Gly Ser Gly Ser Gln Asp Trp Ser Tyr
            675                 680                 685

GGC CTG CGT CCG GGT GGA TCC TAG CTA GCT AGC CAT GG                   2102
Gly Leu Arg Pro Gly Gly Ser     Leu Ala Ser His
            690             695
```

(2) INFORMATION FOR SEQ ID NO:16:

(i) SEQUENCE CHARACTERISTICS:
        (A) LENGTH: 699 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ala Thr Val Ile Asp Arg Ser Gln His Trp Ser Tyr Gly Leu Arg
 1               5                  10                  15

Pro Gly Ser Gly Ser Gln Asp Trp Ser Tyr Gly Leu Arg Pro Gly Gly
            20                  25                  30

Ser Ser Gln His Trp Ser Tyr Gly Leu Arg Pro Gly Ser Gly Ser Gln
        35                  40                  45

Asp Trp Ser Tyr Gly Leu Arg Pro Gly Gly Ser Gln His Trp Ser Tyr
    50                  55                  60
```

-continued

```
Gly Leu Arg Pro Gly Ser Gly Ser Gln Asp Trp Ser Tyr Gly Leu Arg
 65                  70                  75                  80

Pro Gly Gly Ser Ser Gln His Trp Ser Tyr Gly Leu Arg Pro Gly Ser
             85                  90                  95

Gly Ser Gln Asp Trp Ser Tyr Gly Leu Arg Pro Gly Gly Ser Ser Phe
            100                 105                 110

Pro Lys Thr Gly Ala Lys Lys Ile Ile Leu Tyr Ile Pro Gln Asn Tyr
        115                 120                 125

Gln Tyr Asp Thr Glu Gln Gly Asn Gly Leu Gln Asp Leu Val Lys Ala
    130                 135                 140

Ala Glu Glu Leu Gly Ile Glu Val Gln Arg Glu Arg Asn Asn Ile
145                 150                 155                 160

Ala Thr Ala Gln Thr Ser Leu Gly Thr Ile Gln Thr Ala Ile Gly Leu
                165                 170                 175

Thr Glu Arg Gly Ile Val Leu Ser Ala Pro Gln Ile Asp Lys Leu Leu
            180                 185                 190

Gln Lys Thr Lys Ala Gly Gln Ala Leu Gly Ser Ala Glu Ser Ile Val
        195                 200                 205

Gln Asn Ala Asn Lys Ala Lys Thr Val Leu Ser Gly Ile Gln Ser Ile
    210                 215                 220

Leu Gly Ser Val Leu Ala Gly Met Asp Leu Asp Glu Ala Leu Gln Asn
225                 230                 235                 240

Asn Ser Asn Gln His Ala Leu Ala Lys Ala Gly Leu Glu Leu Thr Asn
                245                 250                 255

Ser Leu Ile Glu Asn Ile Ala Asn Ser Val Lys Thr Leu Asp Glu Phe
            260                 265                 270

Gly Glu Gln Ile Ser Gln Phe Gly Ser Lys Leu Gln Asn Ile Lys Gly
        275                 280                 285

Leu Gly Thr Leu Gly Asp Lys Leu Lys Asn Ile Gly Gly Leu Asp Lys
    290                 295                 300

Ala Gly Leu Gly Leu Asp Val Ile Ser Gly Leu Leu Ser Gly Ala Thr
305                 310                 315                 320

Ala Ala Leu Val Leu Ala Asp Lys Asn Ala Ser Thr Ala Lys Lys Val
                325                 330                 335

Gly Ala Gly Phe Glu Leu Ala Asn Gln Val Val Gly Asn Ile Thr Lys
            340                 345                 350

Ala Val Ser Ser Tyr Ile Leu Ala Gln Arg Val Ala Ala Gly Leu Ser
        355                 360                 365

Ser Thr Gly Pro Val Ala Ala Leu Ile Ala Ser Thr Val Ser Leu Ala
    370                 375                 380

Ile Ser Pro Leu Ala Phe Ala Gly Ile Ala Asp Lys Phe Asn His Ala
385                 390                 395                 400

Lys Ser Leu Glu Ser Tyr Ala Glu Arg Phe Lys Lys Leu Gly Tyr Asp
                405                 410                 415

Gly Asp Asn Leu Leu Ala Glu Tyr Gln Arg Gly Thr Gly Thr Ile Asp
            420                 425                 430

Ala Ser Val Thr Ala Ile Asn Thr Ala Leu Ala Ala Ile Ala Gly Gly
        435                 440                 445

Val Ser Ala Ala Ala Ala Asp Leu Thr Phe Glu Lys Val Lys His Asn
    450                 455                 460

Leu Val Ile Thr Asn Ser Lys Lys Glu Val Thr Ile Gln Asn Trp
465                 470                 475                 480
```

```
Phe Arg Glu Ala Asp Phe Ala Lys Glu Val Pro Asn Tyr Lys Ala Thr
                485                 490                 495

Lys Asp Glu Lys Ile Glu Glu Ile Ile Gly Gln Asn Gly Glu Arg Ile
            500                 505                 510

Thr Ser Lys Gln Val Asp Asp Leu Ile Ala Lys Gly Asn Gly Lys Ile
        515                 520                 525

Thr Gln Asp Glu Leu Ser Lys Val Val Asp Asn Tyr Glu Leu Leu Lys
    530                 535                 540

His Ser Lys Asn Val Thr Asn Ser Leu Asp Lys Leu Ile Ser Ser Val
545                 550                 555                 560

Ser Ala Phe Thr Ser Ser Asn Asp Ser Arg Asn Val Leu Val Ala Pro
                565                 570                 575

Thr Ser Met Leu Asp Gln Ser Leu Ser Ser Leu Gln Phe Ala Arg Gly
            580                 585                 590

Ser Gln His Trp Ser Tyr Gly Leu Arg Pro Gly Ser Gly Ser Gln Asp
        595                 600                 605

Trp Ser Tyr Gly Leu Arg Pro Gly Gly Ser Ser Gln His Trp Ser Tyr
    610                 615                 620

Gly Leu Arg Pro Gly Ser Gly Ser Gln Asp Trp Ser Tyr Gly Leu Arg
625                 630                 635                 640

Pro Gly Gly Ser Gln His Trp Ser Tyr Gly Leu Arg Pro Gly Ser Gly
                645                 650                 655

Ser Gln Asp Trp Ser Tyr Gly Leu Arg Pro Gly Gly Ser Ser Gln His
            660                 665                 670

Trp Ser Tyr Gly Leu Arg Pro Gly Ser Gly Ser Gln Asp Trp Ser Tyr
        675                 680                 685

Gly Leu Arg Pro Gly Gly Ser Leu Ala Ser His
    690                 695

(2) INFORMATION FOR SEQ ID NO:17:

(i) SEQUENCE CHARACTERISTICS:
        (A) LENGTH: 1403 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Met Gly Thr Arg Leu Thr Thr Leu Ser Asn Gly Leu Lys Asn Thr Leu
1               5                   10                  15

Thr Ala Thr Lys Ser Gly Leu His Lys Ala Gly Gln Ser Leu Thr Gln
            20                  25                  30

Ala Gly Ser Ser Leu Lys Thr Gly Ala Lys Lys Ile Ile Leu Tyr Ile
        35                  40                  45

Pro Gln Asn Tyr Gln Tyr Asp Thr Glu Gln Gly Asn Gly Leu Gln Asp
    50                  55                  60

Leu Val Lys Ala Ala Glu Glu Leu Gly Ile Glu Val Gln Arg Glu Glu
65                  70                  75                  80

Arg Asn Asn Ile Ala Thr Ala Gln Thr Ser Leu Gly Thr Ile Gln Thr
                85                  90                  95

Ala Ile Gly Leu Thr Glu Arg Gly Ile Val Leu Ser Ala Pro Gln Ile
            100                 105                 110

Asp Lys Leu Leu Gln Lys Thr Lys Ala Gly Gln Ala Leu Gly Ser Ala
        115                 120                 125
```

-continued

```
Glu Ser Ile Val Gln Asn Ala Asn Lys Ala Lys Thr Val Leu Ser Gly
    130                 135                 140

Ile Gln Ser Ile Leu Gly Ser Val Leu Ala Gly Met Asp Leu Asp Glu
145                 150                 155                 160

Ala Leu Gln Asn Asn Ser Asn Gln His Ala Leu Ala Lys Ala Gly Leu
                165                 170                 175

Glu Leu Thr Asn Ser Leu Ile Glu Asn Ile Ala Asn Ser Val Lys Thr
            180                 185                 190

Leu Asp Glu Phe Gly Glu Gln Ile Ser Gln Phe Gly Ser Lys Leu Gln
        195                 200                 205

Asn Ile Lys Gly Leu Gly Thr Leu Gly Asp Lys Leu Lys Asn Ile Gly
    210                 215                 220

Gly Leu Asp Lys Ala Gly Leu Gly Leu Asp Val Ile Ser Gly Leu Leu
225                 230                 235                 240

Ser Gly Ala Thr Ala Ala Leu Val Leu Ala Asp Lys Asn Ala Ser Thr
                245                 250                 255

Ala Lys Lys Val Gly Ala Gly Phe Glu Leu Ala Asn Gln Val Val Gly
            260                 265                 270

Asn Ile Thr Lys Ala Val Ser Ser Tyr Ile Leu Ala Gln Arg Val Ala
        275                 280                 285

Ala Gly Leu Ser Ser Thr Gly Pro Val Ala Ala Leu Ile Ala Ser Thr
    290                 295                 300

Val Ser Leu Ala Ile Ser Pro Leu Ala Phe Ala Gly Ile Ala Asp Lys
305                 310                 315                 320

Phe Asn His Ala Lys Ser Leu Glu Ser Tyr Ala Glu Arg Phe Lys Lys
                325                 330                 335

Leu Gly Tyr Asp Gly Asp Asn Leu Leu Ala Glu Tyr Gln Arg Gly Thr
            340                 345                 350

Gly Thr Ile Asp Ala Ser Val Thr Ala Ile Asn Thr Ala Leu Ala Ala
        355                 360                 365

Ile Ala Gly Gly Val Ser Ala Ala Gly Arg Arg Ile Arg Gly Ile
    370                 375                 380

Pro Gly Asp Pro Val Val Leu Gln Arg Arg Asp Trp Glu Asn Pro Gly
385                 390                 395                 400

Val Thr Gln Leu Asn Arg Leu Ala Ala His Pro Pro Phe Ala Ser Trp
                405                 410                 415

Arg Asn Ser Glu Glu Ala Arg Thr Asp Arg Pro Ser Gln Gln Leu Arg
            420                 425                 430

Ser Leu Asn Gly Glu Trp Arg Phe Ala Trp Phe Pro Ala Pro Glu Ala
        435                 440                 445

Val Pro Glu Ser Trp Leu Glu Cys Asp Leu Pro Glu Ala Asp Thr Val
    450                 455                 460

Val Val Pro Ser Asn Trp Gln Met His Gly Tyr Asp Ala Pro Ile Tyr
465                 470                 475                 480

Thr Asn Val Thr Tyr Pro Ile Thr Val Asn Pro Pro Phe Val Pro Thr
                485                 490                 495

Glu Asn Pro Thr Gly Cys Tyr Ser Leu Thr Phe Asn Val Asp Glu Ser
            500                 505                 510

Trp Leu Gln Glu Gly Gln Thr Arg Ile Ile Phe Asp Gly Val Asn Ser
        515                 520                 525

Ala Phe His Leu Trp Cys Asn Gly Arg Trp Val Gly Tyr Gly Gln Asp
    530                 535                 540

Ser Arg Leu Pro Ser Glu Phe Asp Leu Ser Ala Phe Leu Arg Ala Gly
```

```
545                 550                 555                 560
Glu Asn Arg Leu Ala Val Met Val Leu Arg Trp Ser Asp Gly Ser Tyr
                565                 570                 575

Leu Glu Asp Gln Asp Met Trp Arg Met Ser Gly Ile Phe Arg Asp Val
                580                 585                 590

Ser Leu Leu His Lys Pro Thr Thr Gln Ile Ser Asp Phe His Val Ala
                595                 600                 605

Thr Arg Phe Asn Asp Asp Phe Ser Arg Ala Val Leu Glu Ala Glu Val
            610                 615                 620

Gln Met Cys Gly Glu Leu Arg Asp Tyr Leu Arg Val Thr Val Ser Leu
625                 630                 635                 640

Trp Gln Gly Glu Thr Gln Val Ala Ser Gly Thr Ala Pro Phe Gly Gly
                645                 650                 655

Glu Ile Ile Asp Glu Arg Gly Gly Tyr Ala Asp Arg Val Thr Leu Arg
                660                 665                 670

Leu Asn Val Glu Asn Pro Lys Leu Trp Ser Ala Glu Ile Pro Asn Leu
            675                 680                 685

Tyr Arg Ala Val Val Glu Leu His Thr Ala Asp Gly Thr Leu Ile Glu
        690                 695                 700

Ala Glu Ala Cys Asp Val Gly Phe Arg Glu Val Arg Ile Glu Asn Gly
705                 710                 715                 720

Leu Leu Leu Leu Asn Gly Lys Pro Leu Leu Ile Arg Gly Val Asn Arg
                725                 730                 735

His Glu His His Pro Leu His Gly Gln Val Met Asp Glu Gln Thr Met
                740                 745                 750

Val Gln Asp Ile Leu Leu Met Lys Gln Asn Asn Phe Asn Ala Val Arg
        755                 760                 765

Cys Ser His Tyr Pro Asn His Pro Leu Trp Tyr Thr Leu Cys Asp Arg
770                 775                 780

Tyr Gly Leu Tyr Val Val Asp Glu Ala Asn Ile Glu Thr His Gly Met
785                 790                 795                 800

Val Pro Met Asn Arg Leu Thr Asp Asp Pro Arg Trp Leu Pro Ala Met
                805                 810                 815

Ser Glu Arg Val Thr Arg Met Val Gln Arg Asp Arg Asn His Pro Ser
                820                 825                 830

Val Ile Ile Trp Ser Leu Gly Asn Glu Ser Gly His Gly Ala Asn His
            835                 840                 845

Asp Ala Leu Tyr Arg Trp Ile Lys Ser Val Asp Pro Ser Arg Pro Val
        850                 855                 860

Gln Tyr Glu Gly Gly Gly Ala Asp Thr Thr Ala Thr Asp Ile Ile Cys
865                 870                 875                 880

Pro Met Tyr Ala Arg Val Asp Arg Asp Gln Pro Phe Pro Ala Val Pro
                885                 890                 895

Lys Trp Ser Ile Lys Lys Trp Leu Ser Leu Pro Gly Glu Thr Arg Pro
            900                 905                 910

Leu Ile Leu Cys Glu Tyr Ala His Ala Met Gly Asn Ser Leu Gly Gly
        915                 920                 925

Phe Ala Lys Tyr Trp Gln Ala Phe Arg Gln Tyr Pro Arg Leu Gln Gly
        930                 935                 940

Gly Phe Val Trp Asp Trp Val Asp Gln Ser Leu Ile Lys Tyr Asp Glu
945                 950                 955                 960

Asn Gly Asn Pro Trp Ser Ala Tyr Gly Gly Asp Phe Gly Asp Thr Pro
                965                 970                 975
```

```
Asn Asp Arg Gln Phe Cys Met Asn Gly Leu Val Phe Ala Asp Arg Thr
            980                 985                 990

Pro His Pro Ala Leu Thr Glu Ala Lys His Gln Gln Gln Phe Phe Gln
            995                1000                1005

Phe Arg Leu Ser Gly Gln Thr Ile Glu Val Thr Ser Glu Tyr Leu Phe
           1010                1015                1020

Arg His Ser Asp Asn Glu Leu Leu His Trp Met Val Ala Leu Asp Gly
1025                1030                1035                1040

Lys Pro Leu Ala Ser Gly Glu Val Pro Leu Asp Val Ala Pro Gln Gly
                1045                1050                1055

Lys Gln Leu Ile Glu Leu Pro Glu Leu Pro Gln Pro Glu Ser Ala Gly
            1060                1065                1070

Gln Leu Trp Leu Thr Val Arg Val Val Gln Pro Asn Ala Thr Ala Trp
            1075                1080                1085

Ser Glu Ala Gly His Ile Ser Ala Trp Gln Gln Trp Arg Leu Ala Glu
            1090                1095                1100

Asn Leu Ser Val Thr Leu Pro Ala Ala Ser His Ala Ile Pro His Leu
1105                1110                1115                1120

Thr Thr Ser Glu Met Asp Phe Cys Ile Glu Leu Gly Asn Lys Arg Trp
            1125                1130                1135

Gln Phe Asn Arg Gln Ser Gly Phe Leu Ser Gln Met Trp Ile Gly Asp
            1140                1145                1150

Lys Lys Gln Leu Leu Thr Pro Leu Arg Asp Gln Phe Thr Arg Ala Pro
            1155                1160                1165

Leu Asp Asn Asp Ile Gly Val Ser Glu Ala Thr Arg Ile Asp Pro Asn
            1170                1175                1180

Ala Trp Val Glu Arg Trp Lys Ala Ala Gly His Tyr Gln Ala Glu Ala
1185                1190                1195                1200

Ala Leu Leu Gln Cys Thr Ala Asp Thr Leu Ala Asp Ala Val Leu Ile
                1205                1210                1215

Thr Thr Ala His Ala Trp Gln His Gln Gly Lys Thr Leu Phe Ile Ser
            1220                1225                1230

Arg Lys Thr Tyr Arg Ile Asp Gly Ser Gly Gln Met Ala Ile Thr Val
            1235                1240                1245

Asp Val Glu Val Ala Ser Asp Thr Pro His Pro Ala Arg Ile Gly Leu
            1250                1255                1260

Asn Cys Gln Leu Ala Gln Val Ala Glu Arg Val Asn Trp Leu Gly Leu
1265                1270                1275                1280

Gly Pro Gln Glu Asn Tyr Pro Asp Arg Leu Thr Ala Ala Cys Phe Asp
                1285                1290                1295

Arg Trp Asp Leu Pro Leu Ser Asp Met Tyr Thr Pro Tyr Val Phe Pro
            1300                1305                1310

Ser Glu Asn Gly Leu Arg Cys Gly Thr Arg Glu Leu Asn Tyr Gly Pro
            1315                1320                1325

His Gln Trp Arg Gly Asp Phe Gln Phe Asn Ile Ser Arg Tyr Ser Gln
            1330                1335                1340

Gln Gln Leu Met Glu Thr Ser His Arg His Leu Leu His Ala Glu Glu
1345                1350                1355                1360

Gly Thr Trp Leu Asn Ile Asp Gly Phe His Met Gly Ile Gly Gly Asp
                1365                1370                1375

Asp Ser Trp Ser Pro Ser Val Ser Ala Glu Phe Gln Leu Ser Ala Gly
            1380                1385                1390
```

Arg Tyr His Tyr Gln Leu Val Trp Cys Gln Lys
     1395                1400

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 1
        (D) OTHER INFORMATION: /note= "This position is pyroGlu."

(xi) SEQUENCE DESCRIPTION: SEQ ID NO:18:

Glu His Trp Ser Tyr Gly Leu Arg Pro Gly
1              5                   10

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 3
        (D) OTHER INFORMATION: /note= "The amino acid at this
            location can be either Lys, Asp, Val or Asn."

(ix) FEATURE:
        (A) NAME/KEY: Modified-site
        (B) LOCATION: 5
        (D) OTHER INFORMATION: /note= "The amino acid at this
            location can be either Lys, Asp, Val or Asn."

(xi) SEQUENCE DESCRIPTION: SEQ ID NO:19:

Gly Gly Xaa Gly Xaa Asp
1            5

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

ATGGCTACTG TTATAGATCG ATCT                                            24

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Met Ala Thr Val Ile Asp Arg Ser
1               5
```

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Gly Thr Ile Asp
1
```

(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Gly Ile Thr Gly
1
```

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Gly Val Ile Ser
1
```

(2) INFORMATION FOR SEQ ID NO:25:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

```
His Val Ala Asn
1
```

(2) INFORMATION FOR SEQ ID NO:26:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

Lys Ile Val Glu
1

(2) INFORMATION FOR SEQ ID NO:27:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:27:

Asp Leu Ala Gly
1

(2) INFORMATION FOR SEQ ID NO:28:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:28:

Lys Val Leu Ser
1

(2) INFORMATION FOR SEQ ID NO:29:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:29:

Asp Ala Phe Glu
1

(2) INFORMATION FOR SEQ ID NO:30:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:30:

Lys Leu Val Gln
1

(2) INFORMATION FOR SEQ ID NO:31:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein -continued

```
    (xi) SEQUENCE DESCRIPTION: SEQ ID NO:31:

Gly Ile Ile Asp
1

(2) INFORMATION FOR SEQ ID NO:32:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

Arg Tyr Leu Ala Asn
1               5

(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Lys Phe Leu Leu Asn
1               5

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Lys Ala Tyr Val Asp
1               5
```

POLYNUCLEOTIDES ENCODING LKT 111

CROSS-REFERENCE TO RELATED APPLICATION

This application is a continuation of Ser. No. 09/124,491 filed Jul. 29, 1998, now U.S. Pat. No. 6,022,960 which is a divisional of Ser. No. 08/694,865 filed Aug. 9, 1996, now U.S. Pat. No. 5,837,268 which is a continuation-in-part of Ser. No. 08/387,156 filed Feb. 10, 1995, now U.S. Pat. No. 5,723,129, which is a continuation-in-part of Ser. No. 07/960,932 filed Oct. 14, 1992, now U.S. Pat. No. 5,422,110, which is a continuation-in-part of Ser. No. 07/779,171 filed Oct. 16, 1991, now abandoned.

TECHNICAL FIELD

The present invention relates generally to immunological carrier systems. More particularly, the invention pertains to leukotoxin-GnRH chimeras including more than one copy of a GnRH polypeptide. The chimeras demonstrate enhanced immunogenicity as compared to the immunogenicity of GnRH polypeptides alone.

BACKGROUND OF THE INVENTION

In vertebrates, synthesis and release of the two gonadotrophic hormones, luteinizing hormone (LH) and follicle stimulating hormone (FSH), are regulated by a polypeptide referred to as Gonadotropin releasing hormone (GnRH) (formerly designated LHRH). Accordingly, one approach to fertility control in an animal population is to reduce the levels of GnRH, such as by immunization against GnRH, which effects a reduction in the levels of LH and FSH and the concomitant disruption of estrous cycles and spermatogenesis. See e.g., Adams et al., *J. Anim. Sci.* (1990) 68:2793–2802.

Early studies of the GnRH molecule have shown that it is possible to raise antisera in response to repeated injections of synthetic GnRH peptides (Arimura et al., *Endocrinology* (1973) 93(5):1092–1103). Further, antibodies to GnRH have been raised in a number of species by chemical conjugation of GnRH to a suitable carrier and administration of the conjugate in an appropriate adjuvant (Carelli et al., *Proc. Natl. Acad. Sci.* (1982) 79:5392–5395). Recombinant fusion proteins comprising GnRH or GnRH-analogues have also been described for use in peptide vaccines for the immunological castration or inhibition of reproductive function of various domesticated and farm animals (Meloen et al., *Vaccine* (1994) 12(8):741–746; Hoskinson et al., *Aust. J. Biotechnol.* (1990) 4:166–170; and International Publication Nos. WO 92/19746, published Nov. 12, 1992; WO 91/02799, published Mar. 7, 1991; WO 90/11298, published Oct. 4, 1990 and WO 86/07383, published Dec. 18, 1986).

However, attempts have fallen short of providing adequate immunological sterilization products due to the poor immunogenicity of GnRH peptides and due to the fact that chemical conjugation protocols are difficult to control, rendering substantially heterogenous and poorly-defined GnRH conjugates. Further, peptide vaccines based on GnRH have met with limited success in providing uniform effects on individual animal subjects even after repeated vaccination. In this regard, prior GnRH constructs have failed to provide a uniformly successful immunological sterilization vaccine product due to the fact that GnRH is a small, "self" molecule that is not normally recognized by a subject's immune system, rendering the molecule poorly immunogenic and inherently unable to induce a significant immune response against endogenous GnRH.

It is generally recognized that the immunogenicity of viral antigens, small proteins or endogenous substances may be significantly increased by producing immunogenic forms of those molecules comprising multiple copies of selected epitopes. In this regard, constructs based on two or four repeats of peptides 9–21 of herpes simplex virus type 1 glycoprotein D (Ploeg et al., *J. Immuno. Methods* (1989) 124:211–217), two to six repeats of the antigenic circumsporozoite tetrapeptide NPNA of *Plasmodium falciparum* (Lowell et al., *Science* (1988) 240:800–802), two or four copies of the major immunogenic site of VP1 of foot-and-mouth disease virus (Broekhuijsen et al., *J. gen. Virol.* (1987) 68:3137–3143) and tandem repeats of a GnRH-like polypeptide (Meloen et al., *Vaccine* (1994) 12(8):741–746), have been shown to be effective in increasing the immunogenicity of those molecules.

Small proteins or endogenous substances may also be conjugated to a suitable carrier in order to elicit a significant immune response in a challenged host. Suitable carriers are generally polypeptides which include antigenic regions of a protein derived from an infectious material such as a viral surface protein, or a carrier peptide sequence. These carriers serve to non-specifically stimulate T helper cell activity and to help direct antigen to antigen presenting cells for processing and presentation of the peptide at the cell surface in association with molecules of the major histocompatibility complex (MHC).

Several carrier systems have been developed for this purpose. For example, small peptide antigens are often coupled to protein carriers such as keyhole limpet haemocyanin (Bittle et al., *Nature* (1982) 298:30–33), tetanus toxoid (Muller et al., *Proc. Natl. Acad. Sci. U.S.A.* (1982) 79:569–573), ovalbumin, and sperm whale myoglobin, to produce an immune response. These coupling reactions typically result in the incorporation of several moles of peptide antigen per mole of carrier protein. Although presentation of the peptide antigen in multiple copies generally enhances immunogenicity, carriers may elicit strong immunity not relevant to the peptide antigen and this may inhibit the immune response to the peptide vaccine on secondary immunization (Schutze et al, *J. Immun.* (1985) 135:2319–2322).

Antigen delivery systems have also been based on particulate carriers. For example, preformed particles have been used as platforms onto which antigens can be coupled and incorporated. Systems based on proteosomes (Lowell et al., *Science* (1988) 240:800–802), immune stimulatory complexes (Morein et al., *Nature* (1984) 308:457–460), and viral particles such as HBsAg (Neurath et al., *Mol. Immunol.* (1989) 26:53–62) and rotavirus inner capsid protein (Redmond et al., *Mol. Immunol.* (1991) 28:269–278) have been developed.

Carrier systems have also been devised using recombinantly produced chimeric proteins that self assemble into particles. For example, the yeast retrotransposon, Ty, encodes a series of proteins that assemble into virus like particles (Ty-VLPs; Kingsman, S. M., and A. J. Kingsman *Vacc.* (1988) 6:304–306). Foreign genes have been inserted into the TyA gene and expressed in yeast as a fusion protein. The fusion protein retains the capacity to self assemble into particles of uniform size.

Other chimeric protein particles have been examined such as HBsAg, (Valenzuela et al., *Bio/Technol.* (1985) 3:323–326; U.S. Pat. No. 4,722,840; Delpeyroux et al., *Science* (1986) 233:472–475), Hepatitis B core antigen (Clarke et al., *Vaccines* 88 (Ed. H. Ginsberg, et al., 1988) pp.

127–131), Poliovirus (Burke et al., *Nature* (1988) 332:81–82), and Tobacco Mosaic Virus (Haynes et al., *Bio/Technol.* (1986) 4:637–641). However, these carriers are restricted in their usefulness by virtue of the limited size of the active agent which may be inserted into the structural protein without interfering with particle assembly.

Finally, chimeric systems have been devised using a *Pasteurella haemolytica* leukotoxin (LKT) polypeptide fused to a selected antigen. See, e.g., International Publication Nos. WO 93/08290, published Apr. 29, 1993 and WO 92/03558, published Mar. 5, 1992, as well as U.S. Pat. Nos. 5,238,823 and 5,273,889. Inclusion of a LKT carrier portion in a peptide antigen chimera supplies enhanced immunogenicity to the chimera by providing T-cell epitopes having broad species reactivity, thereby eliciting a T-cell dependent immune response in immunized subjects. In this regard, inducement of adequate T-cell help is essential in the generation of an immune response to the peptide antigen portion of the chimera, particularly where the antigen is an endogenous molecule. However, the use of a leukotoxin polypeptide carrier in combination with multiple epitopes of the GnRH peptide has not heretofore been described.

DISCLOSURE OF THE INVENTION

The present invention is based on the construction of novel gene fusions between the *P. haemolytica* leukotoxin gene, variants thereof, and one or more nucleotide sequences encoding multiple GnRH polypeptides. These constructs produce chimeric proteins that display surprisingly enhanced immunogenicity when compared to the immunologic reaction elicited by administration of GnRH alone.

Thus in one embodiment, the present invention is directed to a chimeric protein comprising a leukotoxin polypeptide fused to one or more multimers wherein each multimer comprises more than one selected GnRH polypeptide. The leukotoxin portion of the chimera acts to increase the immunogenicity of the GnRH polypeptides. More particularly, the GnRH multimers used herein may correspond to more than one copy of a selected GnRH polypeptide or epitope, or multiple tandem repeats of a selected GnRH polypeptide or epitope. Further, GnRH multimers may be located at the carboxyl and/or amino terminal of the leukotoxin polypeptide, at sites internal to the leukotoxin polypeptide, or any combination of such sites. Each GnRH multimer may also correspond to a molecule of the general formula GnRH-X-GnRH, wherein X is selected from the group consisting of a peptide linkage, an amino acid spacer group and [GnRH]$_n$, where n is greater than or equal to 1, and further wherein "GnRH" may comprise any GnRH polypeptide. In one particular embodiment, a chimeric protein comprising a leukotoxin polypeptide fused to two GnRH multimers is provided. In this molecule, the C-terminus of one of the GnRH multimers is fused to the N-terminus of the leukotoxin polypeptide, and the N-terminus of the leukotoxin polypeptide is fused to the N-terminus of the other GnRH multimer.

Also disclosed are vaccine compositions comprising the chimeric proteins with a pharmaceutically acceptable vehicle, as well as methods for presenting one or more selected GnRH multimers to a host subject by the administration of an effective amount of the subject vaccine compositions.

In another embodiment, the invention is directed to DNA constructs encoding the chimeric proteins. The DNA constructs comprise a first nucleotide sequence encoding a leukotoxin polypeptide operably linked to one or more selected nucleotide sequences, each selected nucleotide sequence encoding more than one copy of a GnRH polypeptide or epitope.

In yet another embodiment, the invention is directed to expression cassettes comprised of the above-described DNA constructs operably linked to control sequences that direct the transcription thereof, whereby the constructs can be transcribed and translated in a host cell.

In another embodiment, the invention is directed to host cells transformed with these expression cassettes.

Another embodiment of the invention provides a method of producing a recombinant polypeptide. The method comprises (a) providing a population of host cells described above and (b) culturing the population of cells under conditions whereby the chimeric polypeptide encoded by the expression cassette is expressed.

These and other embodiments of the present invention will readily occur to those of ordinary skill in the art in view of the disclosure herein.

BRIEF DESCRIPTION OF THE FIGURES

FIGS. 1A and 1B (SEQ ID NO:1 and SEQ ID NO:2) (SEQ ID NO:3 and SEQ ID NO:4) show the nucleotide sequences and amino acid sequences of the GnRH constructs used in the chimeric leukotoxin-GnRH polypeptide gene fusions. FIG. 1A (SEQ ID NO:1 and SEQ ID NO:2) depicts GnRH-1 which includes a single copy of a GnRH decapeptide; FIG. 1B (SEQ ID NO:3 and SEQ ID NO:4) depicts GnRH-2 which includes four copies of a GnRH decapeptide when n=1, and eight copies of GnRH when n=2, etc.

Figure 3A:
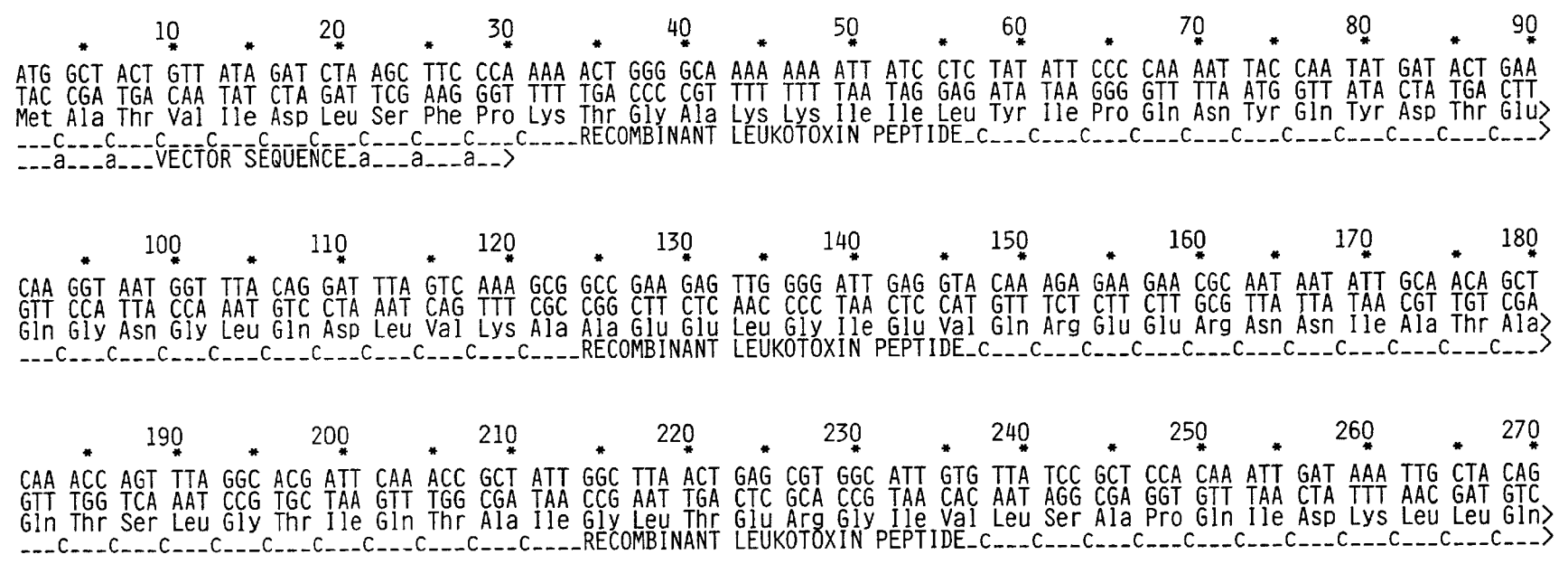
Figure 3B:
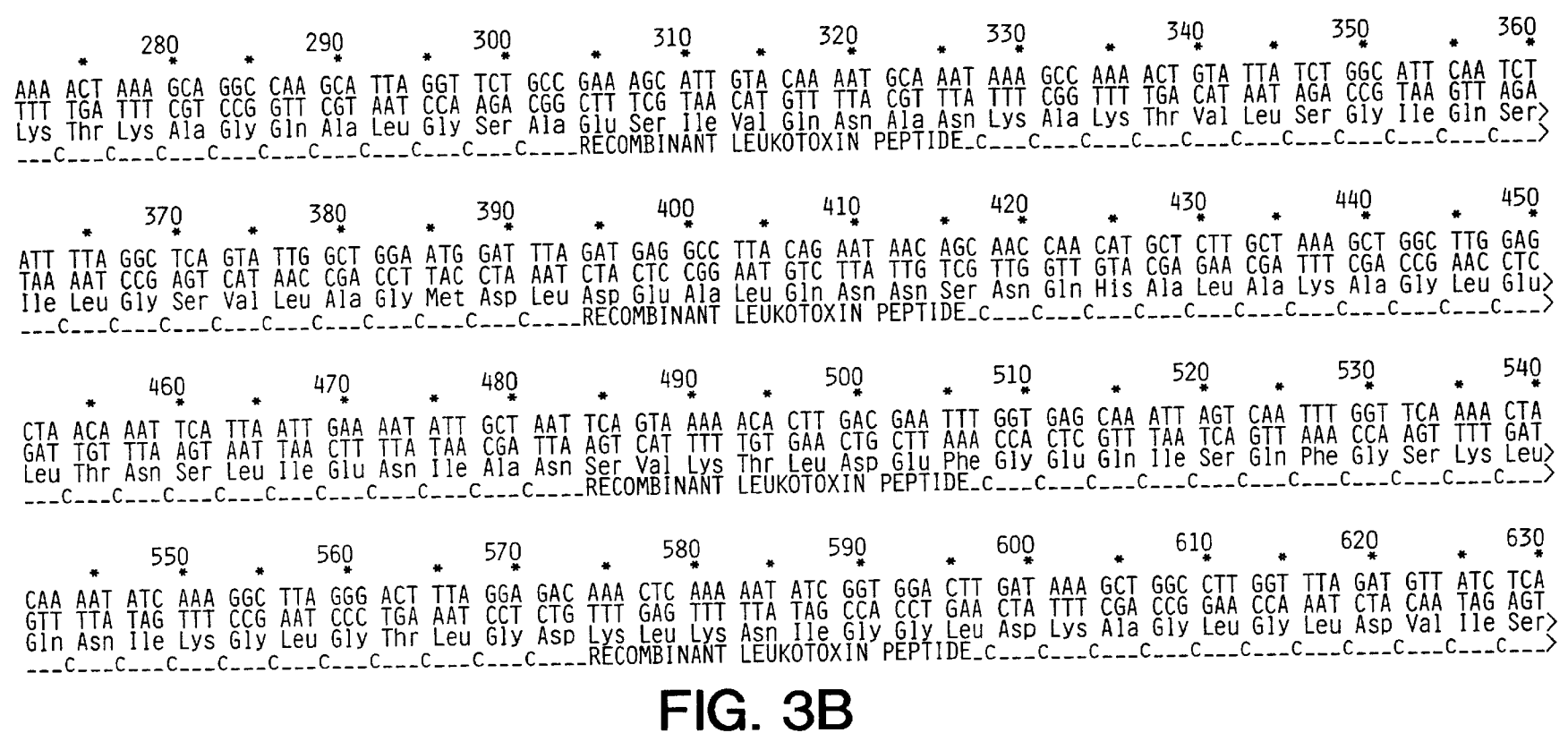
Figure 3C:
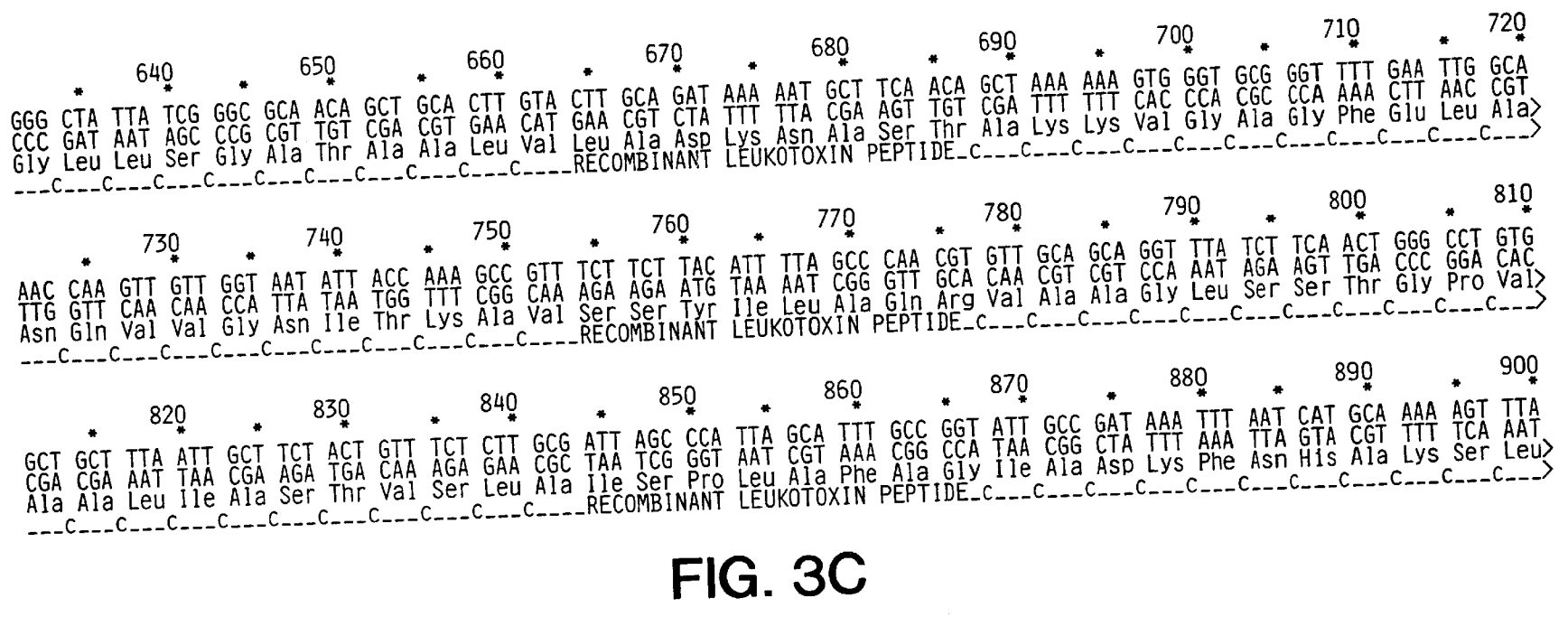
Figure 3D:
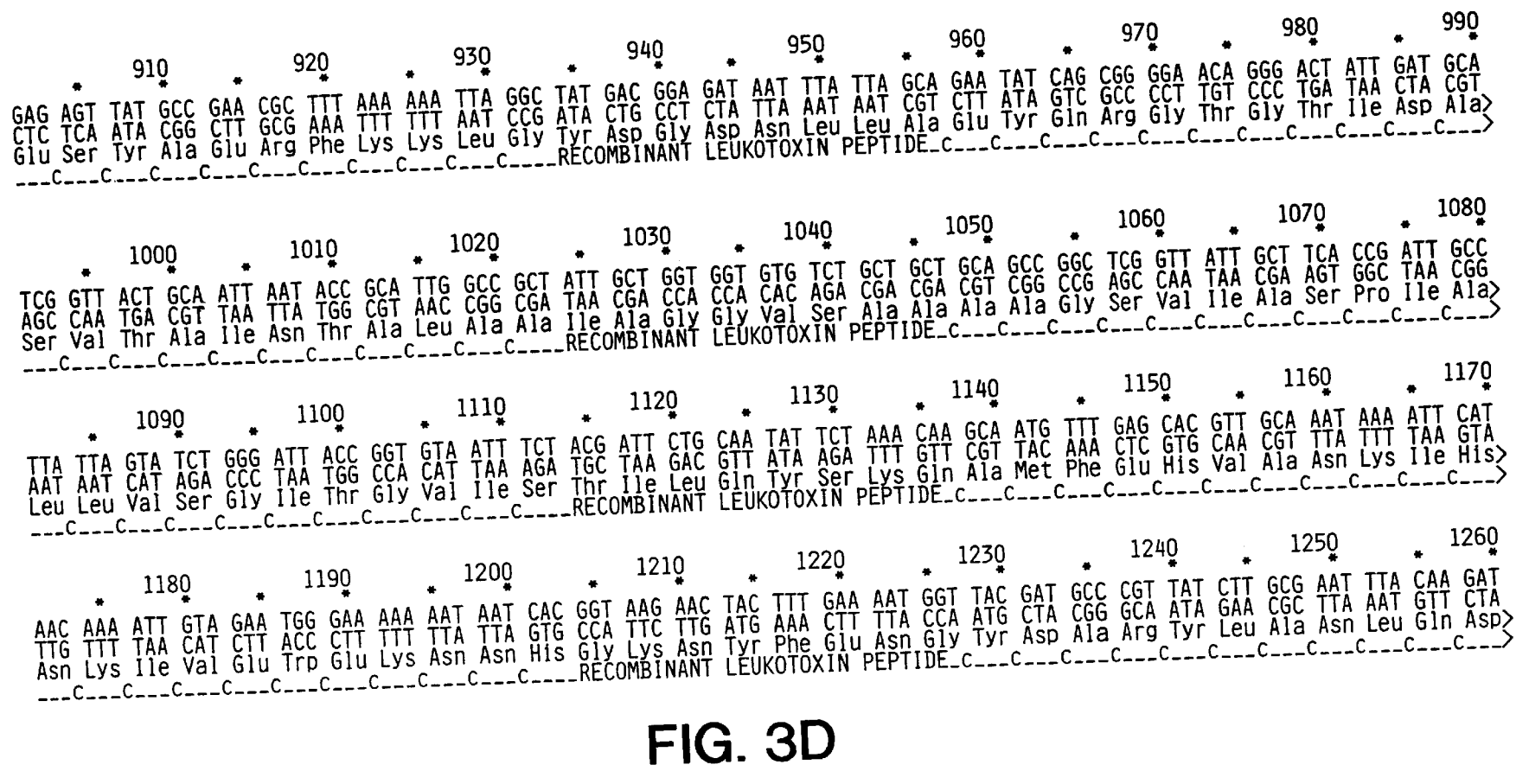
Figure 3E:
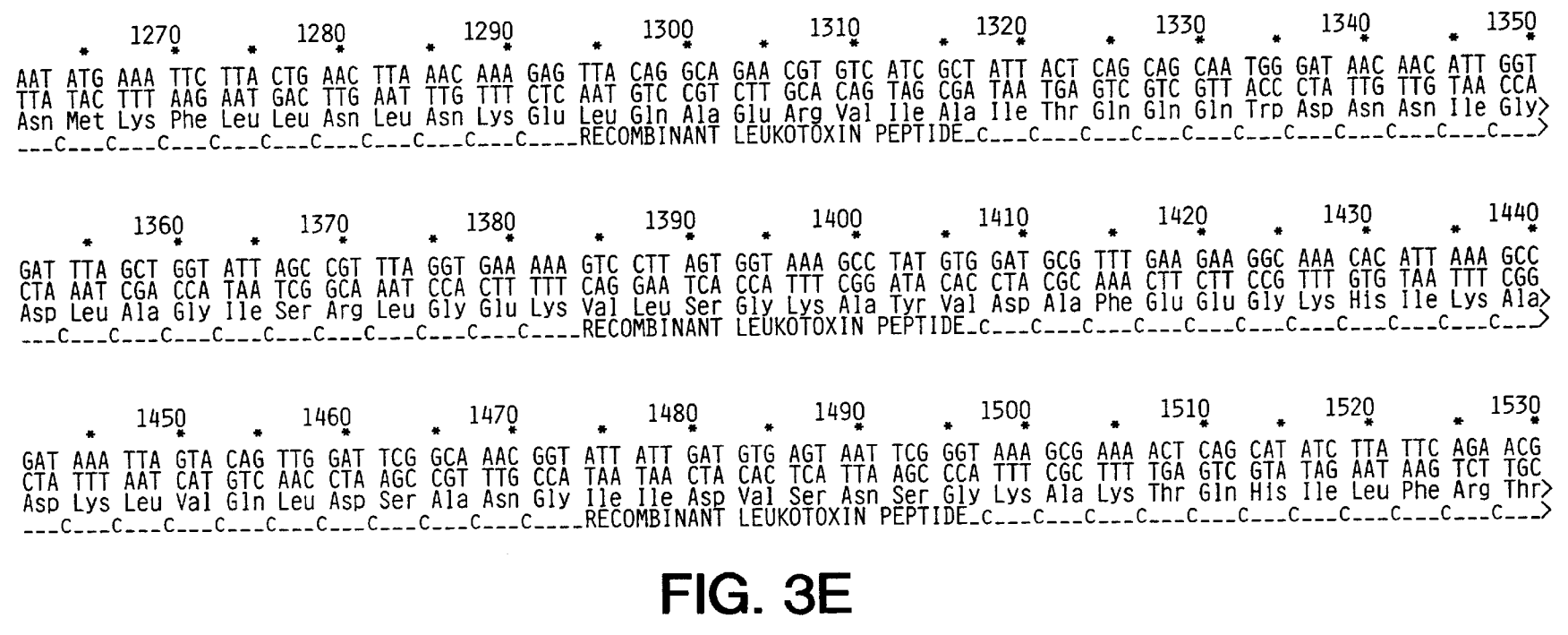
Figure 3F:
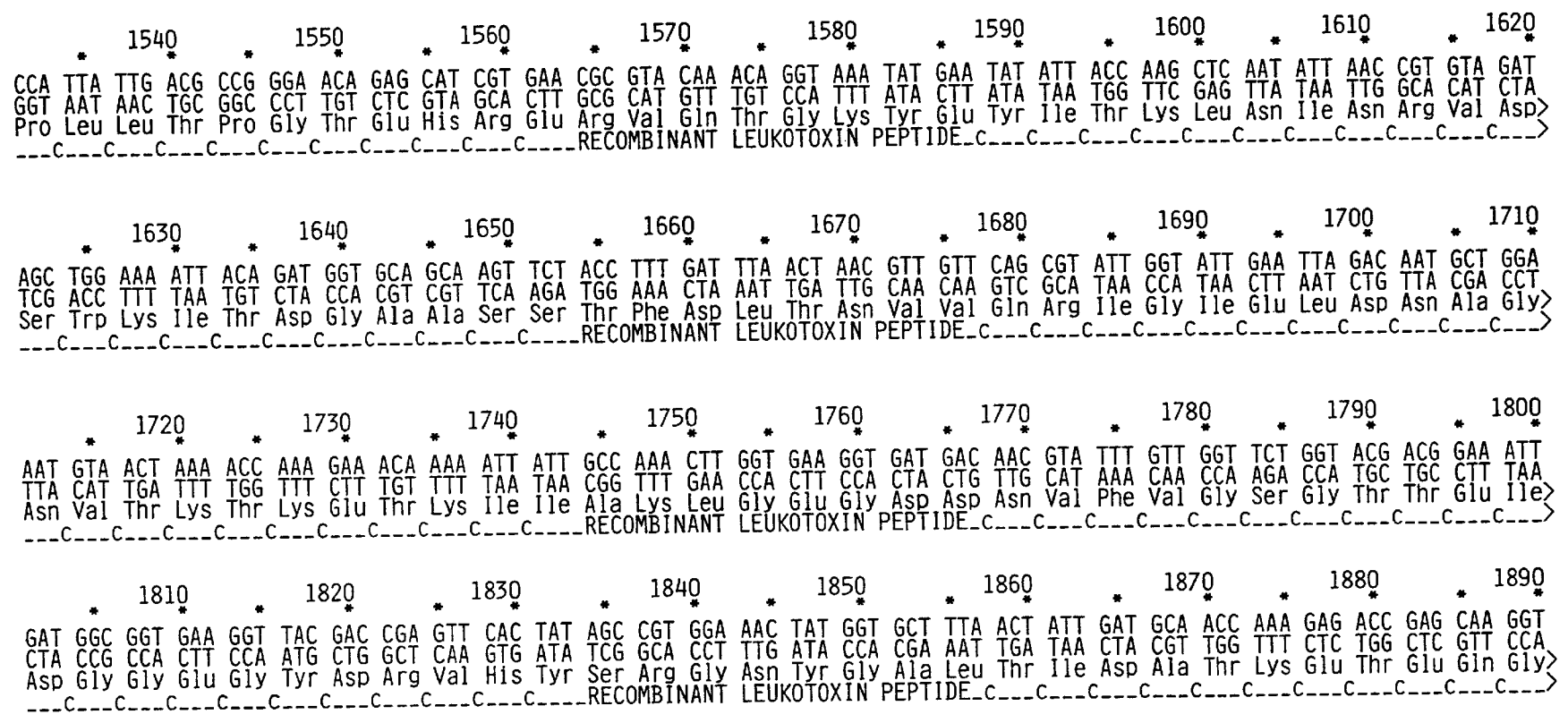
Figure 3G:
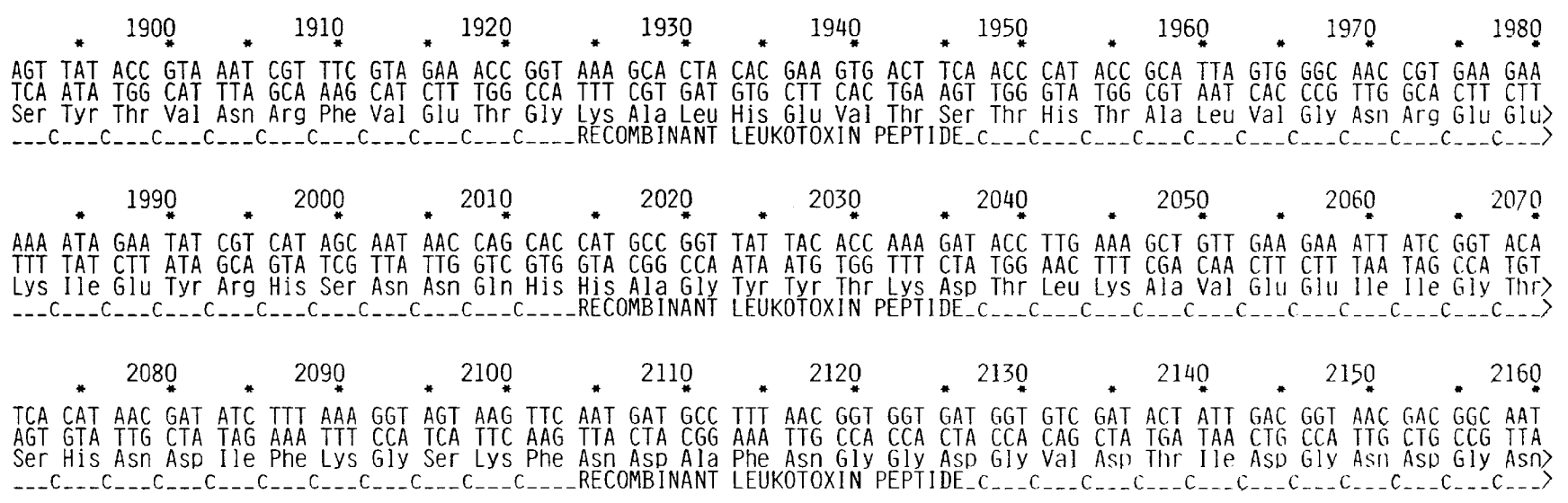
Figure 3H:
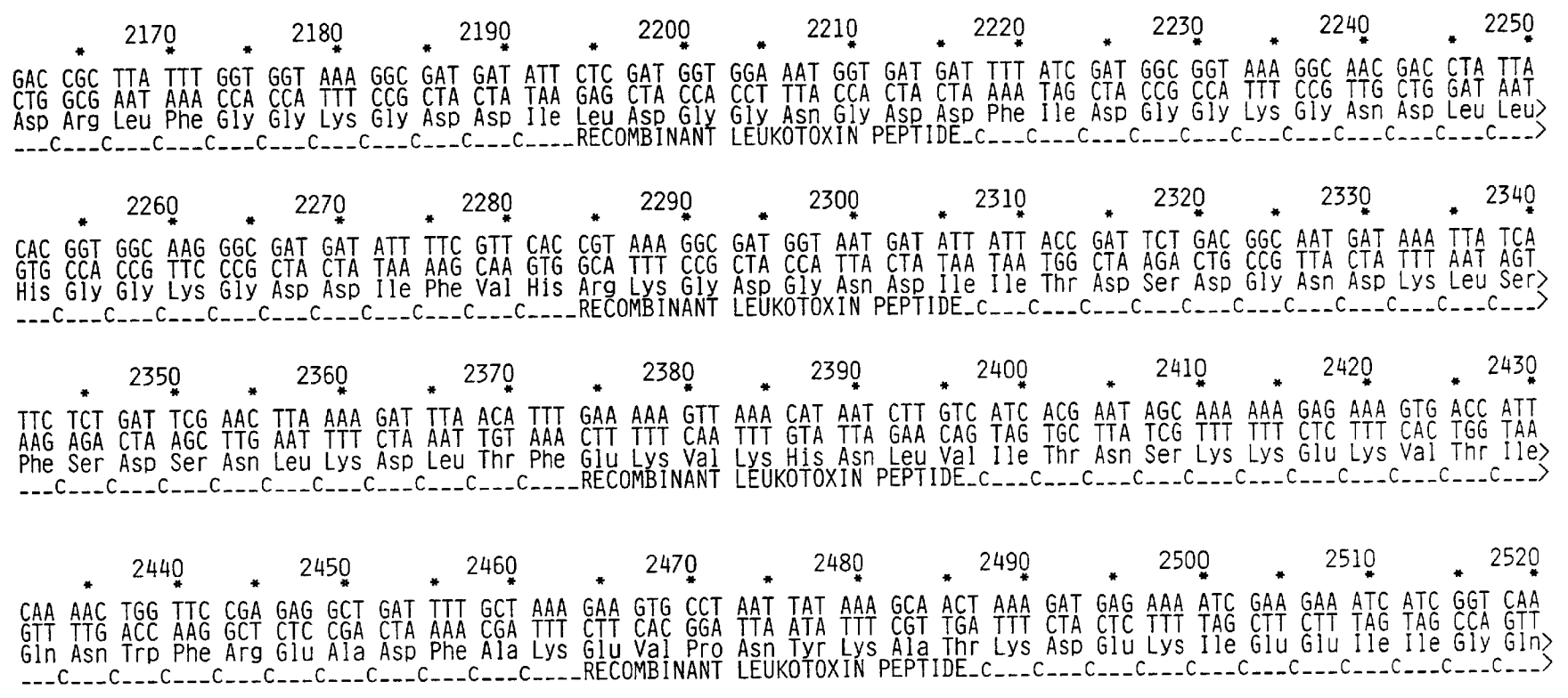
Figure 3I:
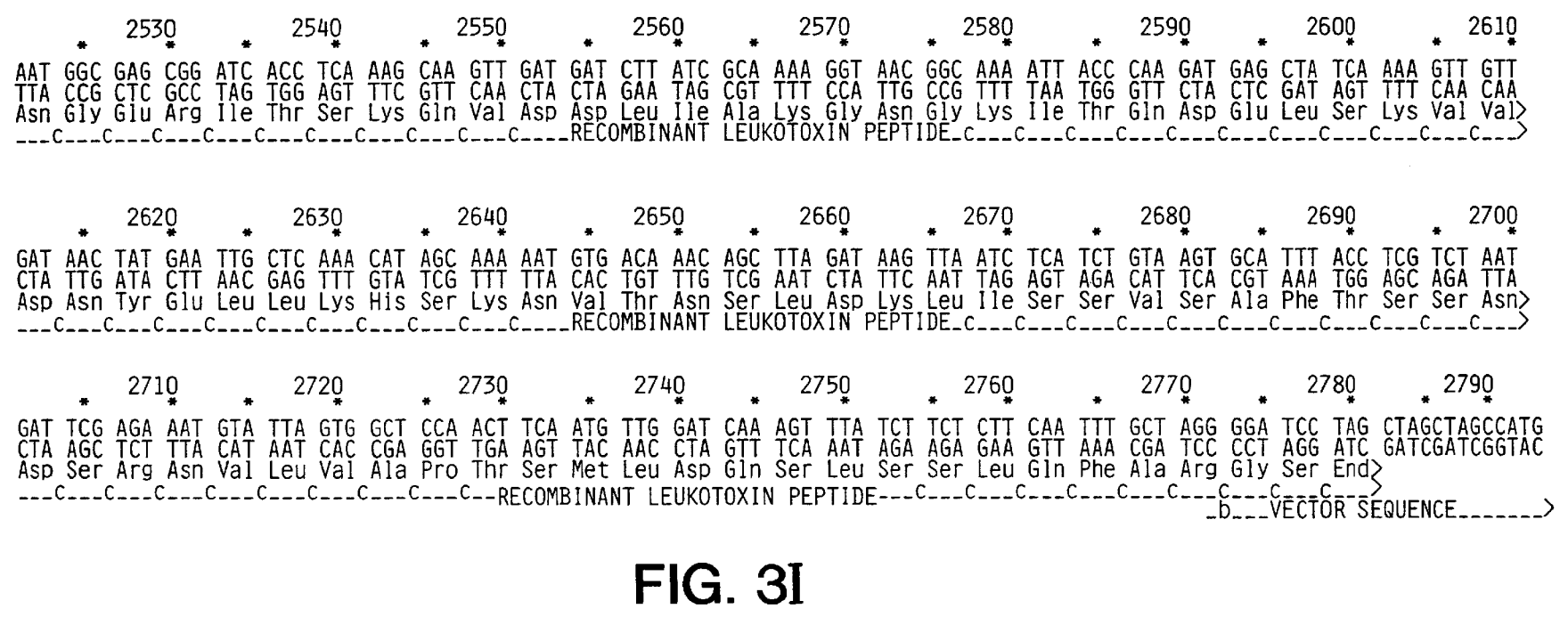

FIGS. 3A through 3I (SEQ ID NO:5 and SEQ ID NO:6) show the nucleotide sequence and predicted amino acid sequence of leukotoxin 352 (LKT 352). Both the structural gene for LKT 352 and the sequences of the flanking vector regions are shown.

FIGS. 5A through 5G (SEQ ID NO:7 and SEQ ID NO:8) show the nucleotide sequence and predicted amino acid sequence of the LKT-GnRH chimeric protein from pCB113. The nucleotide sequence and predicted amino acid sequence of the LKT-GnRH chimeric protein from pCB112 are identical to the sequences of the chimeric protein derived from pCB113 except that the sequence for multiple copy GnRH was inserted twice as described above in regard to FIG. 4.

FIGS. 7A through 7D (SEQ ID NO:9 and SEQ ID NO:10) show the nucleotide sequence and predicted amino acid sequence of the LKT-GnRH chimeric protein from pCB111. The nucleotide sequence and predicted amino acid sequence of the LKT-GnRH chimeric protein from pCB114 are identical to the sequences of the chimeric protein derived from pCB111 except that the sequence for multiple copy GnRH was inserted twice as described above in regard to FIG. 6.

FIG. 8A (SEQ ID NO:11 and SEQ ID NO:12) and FIG. 8B (SEQ ID NO:13 and SEQ ID NO:14) show the nucleotide sequence and predicted amino acid sequence of the blunt end fusion point of the truncated leukotoxin gene of plasmid pCB111 (FIG. 8B), where an internal DNA fragment (of approximately 1300 bp in length) was removed from LKT 352 by digestion with the restriction enzymes BstB1 and Nae1 (FIG. 8A).

FIGS. 9A through 9F (SEQ ID NO:15 and SEQ ID NO:16) show the nucleotide sequence and predicted amino acid sequence of the LKT-GnRH chimeric protein from pCB122.

FIG. 11 (SEQ ID NO:17) depicts the predicted amino acid sequence of the LKT 101 leukotoxin polypeptide.

DETAILED DESCRIPTION

Figure 2:
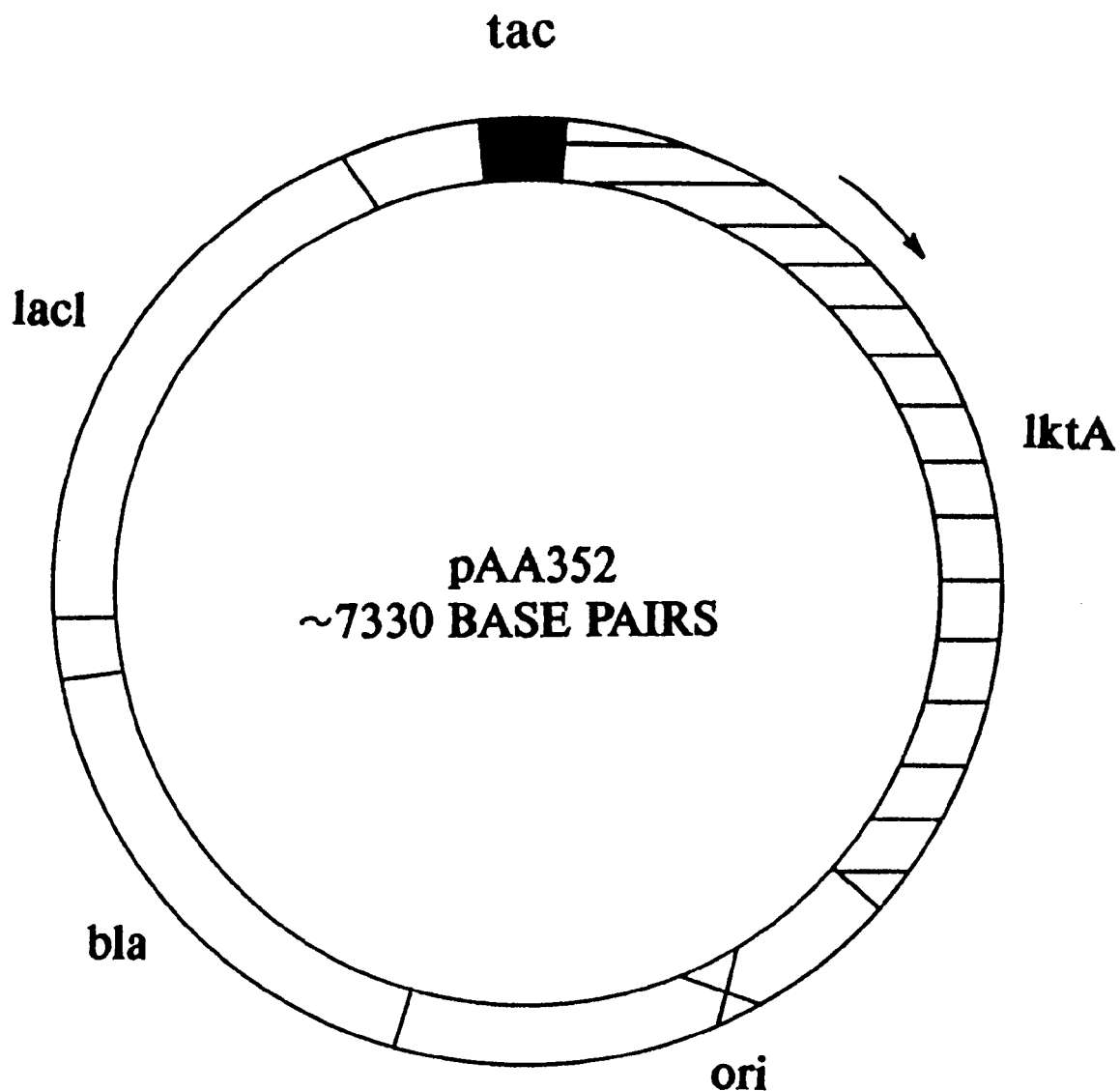
FIG. 2 depicts the structure of Plasmid pAA352 wherein tac is the hybrid trp::lac promoter from *E. coli*; bla represents the β-lactamase gene (ampicillin resistance); ori is the ColE1-based plasmid origin of replication; lktA is the *P. haemolytica* leukotoxin structural gene; and lacI is the *E. coli* lac operon repressor. The direction of transcription/translation of the leukotoxin gene is indicated by the arrow. The size of each component is not drawn to scale.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual; DNA Cloning,* Vols. I and II (D. N. Glover ed.) *Oligonucleotide Synthesis* (M. J. Gait ed.); *Nucleic Acid Hybridization* (B. D. Hames & S. J. Higgins eds.); *Animal Cell Culture* (R. K. Freshney ed.); *Immobilized Cells and Enzymes* (IRL press); B. Perbal, *A Practical Guide to Molecular Cloning;* the series, *Methods In Enzymology* (S. Colowick and N. Kaplan eds., Academic Press, Inc.); and *Handbook of Experimental Immunology,* Vols. I–IV (D. M. Weir and C. C. Blackwell eds., Blackwell Scientific Publications).

All patents, patent applications, and publications mentioned herein, whether supra or infra, are hereby incorporated by reference in their entirety.

A. Definitions

In describing the present invention, the following terms will be employed, and are intended to be defined as indicated below.

The term "Gonadotropin releasing hormone" or "GnRH" refers to a decapeptide secreted by the hypothalamus which controls release of both luteinizing hormone (LH) and follicle stimulating hormone (FSH) in vertebrates (Fink, G., *British Medical Bulletin* (1979) 35:155–160). The amino acid sequence of GnRH is highly conserved among vertebrates, and especially in mammals. In this regard, GnRH derived from most mammals including human, bovine, porcine and ovine GnRH (formerly designated LHRH) has the amino acid sequence pyroGlu-His-Trp-Ser-Tyr-Gly-Leu-Arg-Pro-Gly-NH$_2$ (SEQ ID NO:18) (Murad et al., *Hormones and Hormone Antagonists,* in *The Pharmacological Basis of Therapeutics,* Sixth Edition (1980) and Seeburg et al., *Nature* (1984) 311:666–668).

As used herein a "GnRH polypeptide" includes a molecule derived from a native GnRH sequence, as well as recombinantly produced or chemically synthesized GnRH polypeptides having amino acid sequences which are substantially homologous to native GnRH and which remain immunogenic, as described below. Thus, the term encompasses derivatives and analogues of GnRH including any single or multiple amino acid additions, substitutions and/or deletions occurring internally or at the amino or carboxy terminuses of the peptide. Accordingly, under the invention, a "GnRH polypeptide" includes molecules having the native sequence, molecules such as that depicted in FIG. 1A (having an N-terminal Gln residue rather than a pyroGlu residue), and molecules with other amino acid additions, substitutions and/or deletions which retain the ability to elicit formation of antibodies that cross react with naturally occurring GnRH. Particularly contemplated herein are repeated sequences of GnRH polypeptides such as in the oligomer depicted in FIG. 1B (wherein each of the selected GnRH polypeptides comprises a N-terminal Gln substitution, and further wherein every other GnRH polypeptide comprises an Asp residue substitution at position 2). Epitopes of GnRH are also captured by the definition.

The term "epitope" refers to the site on an antigen or hapten to which a specific antibody molecule binds. Since GnRH is a very small molecule, the identification of epitopes thereof which are able to elicit an antibody response is readily accomplished using techniques well known in the art. See, e.g., Geysen et al. *Proc. Natl. Acad. Sci. USA* (1984) 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709–715 (technique for identifying peptides with high affinity for a given antibody).

As used herein the term "T-cell epitope" refers to a feature of a peptide structure which is capable of inducing T-cell immunity towards the peptide structure or an associated hapten. In this regard, it is accepted in the art that T-cell epitopes comprise linear peptide determinants that assume extended conformations within the peptide-binding cleft of MHC molecules, (Unanue et al., *Science* (1987) 236:551–557). Conversion of polypeptides to MHC class II-associated linear peptide determinants (generally between 5–14 amino acids in length) is termed "antigen processing" which is carried out by antigen presenting cells (APCs). More particularly, a T-cell epitope is defined by local features of a short peptide structure, such as primary amino acid sequence properties involving charge and hydrophobicity, and certain types of secondary structure, such as helicity, that do not depend on the folding of the entire polypeptide. Further, it is believed that short peptides capable of recognition by helper T-cells are generally amphipathic structures comprising a hydrophobic side (for interaction with the MHC molecule) and a hydrophilic side (for interacting with the T-cell receptor), (Margalit et al., *Computer Prediction of T-cell Epitopes, New Generation Vaccines* Marcel-Dekker, Inc, ed. G. C. Woodrow et al., (1990) pp. 109–116) and further that the amphipathic structures have an α-helical configuration (see, e.g., Spouge et al., *J. Immunol.* (1987) 138:204–212; Berkower et al., *J. Immunol.* (1986) 136:2498–2503).

Hence, segments of proteins which include T-cell epitopes can be readily predicted using numerous computer programs. (See e.g., Margalit et al., *Computer Prediction of T-cell Epitopes, New Generation Vaccines* Marcel-Dekker, Inc, ed. G. C. Woodrow et al., (1990) pp. 109–116). Such programs generally compare the amino acid sequence of a peptide to sequences known to induce a T-cell response, and search for patterns of amino acids which are believed to be required for a T-cell epitope.

An "immunogenic protein" or "immunogenic amino acid sequence" is a protein or amino acid sequence, respectively, which elicits an immunological response in a subject to which it is administered. Under the invention, a "GnRH immunogen" refers to a GnRH molecule which, when introduced into a host subject, stimulates an immune response. In this regard, a GnRH immunogen includes a multimer corresponding to more than one selected GnRH polypeptide; and, more particularly, to a multimer having either multiple or tandem repeats of selected GnRH polypeptide sequences, multiple or tandem repeats of selected GnRH epitopes, or any conceivable combination thereof.

An "immunological response" to an antigen or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or γδ T cells, directed specifically to an antigen or antigens included in the composition or vaccine of interest. An immunological response can be detected using any of several immunoassays well known in the art.

The term "leukotoxin polypeptide" or "LKT polypeptide" intends a polypeptide which includes at least one T-cell epitope and is derived from a protein belonging to the family of molecules characterized by the carboxy-terminus consensus amino acid sequence Gly-Gly-X-Gly-X-Asp (SEQ ID NO:19) (Highlander et al., *DNA* (1989) 8:15–28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al., *Infect. Immun.* (1987) 55:3233–3236; Lo, *Can. J. Vet. Res.* (1990) 54:S33–S35; Welch, *Mol. Microbiol.* (1991) 5:521–528). This family of toxins is known as the "RTX" family of toxins (Lo, *Can. J. Vet. Res.* (1990) 54:S33–S35). In addition, the term "leukotoxin polypeptide" refers to a leukotoxin polypeptide which is chemically synthesized, isolated from an organism expressing the same, or recombinantly produced. Furthermore, the term intends an immunogenic protein having an amino acid sequence substantially homologous to a contiguous amino acid sequence found in the particular native leukotoxin molecule. Thus, the term includes both full-length and partial sequences, as well as analogues. Although native full-length leukotoxins display cytotoxic activity, the term "leukotoxin" also intends molecules which remain immunogenic yet lack the cytotoxic character of native leukotoxins. The nucleotide sequences and corresponding amino acid sequences for several leukotoxins are known. See, e.g., U.S. Pat. Nos. 4,957,739 and 5,055,400; Lo et al., *Infect. Immun.* (1985) 50:667–67; Lo et al., *Infect. Immun.* (1987) 55:1987–1996; Strathdee et al., *Infect. Immun.* (1987) 55:3233–3236; Highlander et al., *DNA* (1989) 8:15–28; Welch, *Mol. Microbiol.* (1991) 5:521–528. In the chimeras produced according to the present invention, a selected leukotoxin polypeptide sequence imparts enhanced immunogenicity to one or more fused GnRH multimers by providing, among other things, T-cell epitopes comprising small peptide segments in the range of five to fourteen amino acids in length which are capable of complexing with MHC class II molecules for presentation to, and activation of, T-helper cells. As discussed further below, these T-cell epitopes occur throughout the leukotoxin molecule and are thought to be concentrated in the N-terminus portions of leukotoxin, i.e., between amino acid residues 1 to 199.

As used herein, a leukotoxin polypeptide "which lacks cytotoxic activity" refers to a leukotoxin polypeptide as described above which lacks significant cytotoxicity as compared to a native, full-length leukotoxin (such as the full-length *P. haemolytica* leukotoxin described in U.S. Pat. Nos. 5,055,400 and 4,957,739) yet still retains immunogenicity and at least one T-cell epitope. Leukotoxin polypeptides can be tested for cytotoxic activity using any of several known assays such as the lactate dehydrogenase release assay, described by Korzeniewski et al., *Journal of Immunological Methods* 64:313–320, wherein cytotoxicity is measured by the release of lactate dehydrogenase from bovine neutrophils. A leukotoxin molecule is identified as cytotoxic if it causes a statistically significant release of lactate dehydrogenase when compared to a control non-cytotoxic molecule.

The provision of LKT-GnRH chimeras comprising leukotoxin polypeptides which lack cytotoxic activity provides several important benefits. Initially, a leukotoxin polypeptide which lacks cytotoxic activity is desirable since the injection of an active toxin into a subject can result in localized cell death (PMNs and macrophages) and, in turn, cause a severe inflammatory response and abscess at the injection site. In this regard, cytotoxic activity resulting in the killing of macrophages may lead to reduced antigen presentation and hence a suboptimal immune response. The removal of the cytotoxic portion as found in the non-cytotoxic LKT polypeptides used in producing the fusion proteins of the invention also results in a truncated LKT gene which is capable of being expressed at much higher levels than full-length LKT. Further, the use of non-cytotoxic LKT polypeptides in the fusions constructed herein which retain sufficient T-cell antigenicity reduces the overall amount of leukotoxin-GnRH antigen which needs to be administered to a host subject to yield a sufficient B-cell response to the selected GnRH polypeptides. Particular examples of immunogenic leukotoxin polypeptides which lack cytotoxic activity include LKT 352, LKT 111, and LKT 101 which are described in greater detail below.

By "LKT 352" is meant a protein which is derived from the lkta gene present in plasmid pAA352 (FIG. 2, ATCC Accession No. 68283). The nucleotide sequence and corresponding amino acid sequence of this gene are described in International Publication No. WO91/15237 and are shown in FIG. 3. The gene encodes a truncated leukotoxin, having 914 amino acids and an estimated molecular weight of around 99 kDa, which lacks the cytotoxic portion of the molecule. The truncated gene thus produced is expressed at much higher levels than the full-length molecule (more than 40% of total cell protein versus less than 1 of total cell protein for the full-length form) and is more easily purified. The derived LKT 352 is not necessarily physically derived from the sequence present in plasmid pAA352. Rather, it may be generated in any manner, including for example, by chemical synthesis or recombinant production. In addition, the amino acid sequence of the protein need only be substantially homologous to the depicted sequence. Thus, sequence variations may be present so long as the LKT polypeptide functions to enhance the immunogenicity of antigen with which it is associated yet also lacks cytotoxic activity.

Figures 5H, 6:
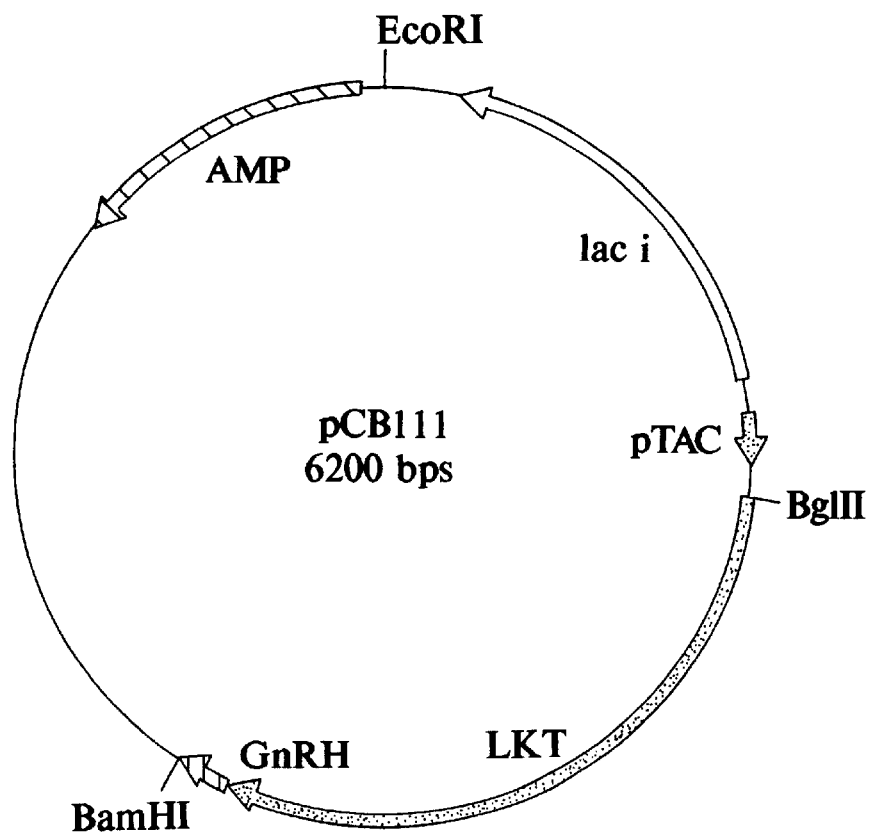
FIG. 6 shows the structure of Plasmid pCB111 carrying a leukotoxin-GnRH (LKT-GnRH) gene fusion.

By "LKT 111" is meant a leukotoxin polypeptide which is derived from the lktA gene present in plasmid pCB111 (FIG. 6, ATCC Accession No. 69748). The nucleotide sequence of this gene and the corresponding amino acid sequence are shown in FIG. 7. The gene encodes a shortened version of leukotoxin which was developed from the recombinant leukotoxin gene present in plasmid pAA352 (FIG. 2, ATCC Accession No. 68283) by removal of an internal DNA fragment of approximately 1300 bp in length. The LKT 111 polypeptide has an estimated molecular weight of 52 kDa (as compared to the 99 kDa LKT 352 polypeptide), but retains portions of the LKT 352 N-terminus containing T-cell epitopes which are necessary for sufficient T-cell immunogenicity, and portions of the LKT 352 C-terminus containing convenient restriction sites for use in-producing the fusion proteins of the present invention. Under the invention, the LKT 111 leukotoxin peptide is not necessarily physically derived from the sequence present in plasmid pCB111. Rather, it may be generated in any manner, including for example, by chemical synthesis or recombinant production. In addition, the amino acid sequence of the protein need only be substantially homologous to the depicted sequence. Thus, sequence variations may be present so long as the protein functions to enhance the immunogenicity of antigen with which it is associated and lacks cytotoxicity.

Figure 10:
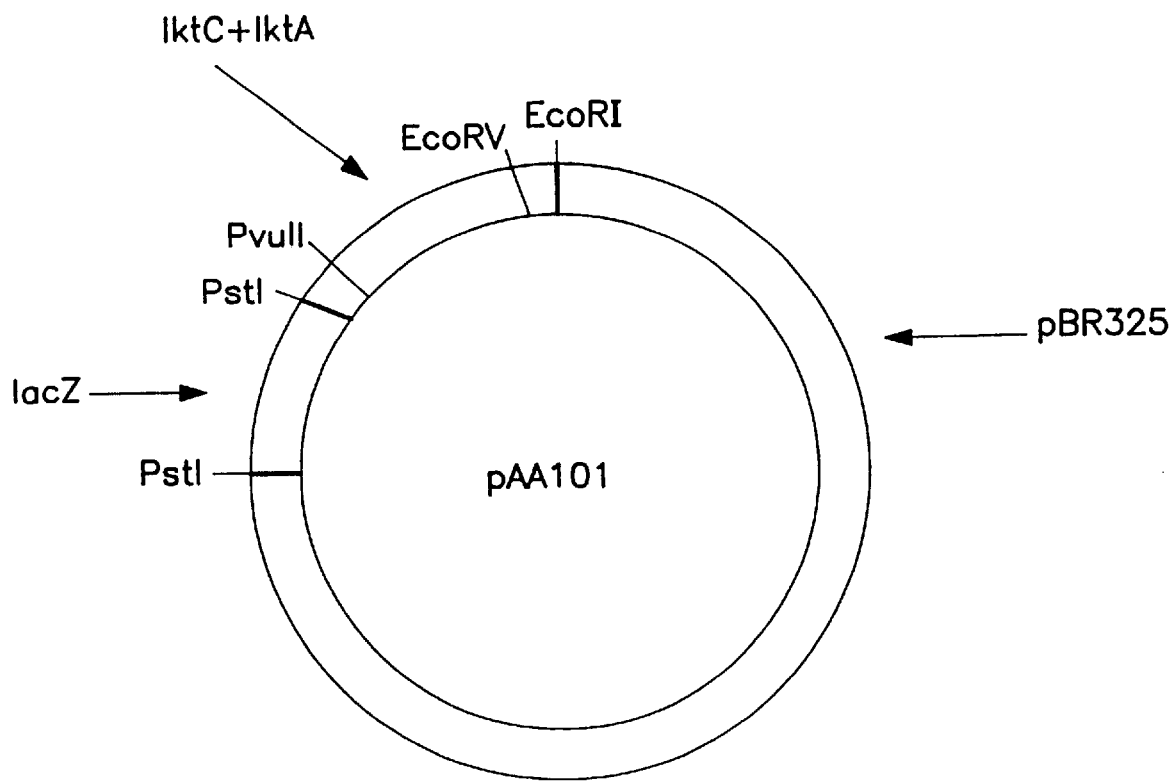
FIG. 10 shows the structure of Plasmid pAA101 carrying the LKT 101 leukotoxin polypeptide which lacks cytotoxic activity.

By "LKT 101" is meant a leukotoxin polypeptide which is derived from the lktA gene present in plasmid pAA101 (FIG. 10, ATCC Accession No. 67883). The predicted amino acid sequence of the *P. haemolytica* leukotoxin produced from the pAA101 construct is depicted in FIG. 11. The LKT 101 polypeptide is expressed from a truncated form of the lkta gene which contains the 5' end of the gene up to the unique Pst1 restriction endonuclease site. The truncated gene was fused to the β-galactosidase gene (lacZ) to facilitate purification of the LKT 101 polypeptide. Under the invention, the LKT 101 leukotoxin peptide is not necessarily physically derived from the sequence present in plasmid pAA101. Rather, it may be generated in any manner, including for example, by chemical synthesis or recombinant production. In addition, the amino acid sequence of the protein need only be substantially homologous to the depicted sequence. Thus, sequence variations may be present so long as the protein functions to enhance the immunogenicity of antigen with which it is associated and lacks cytotoxicity.

A leukotoxin-GnRH polypeptide chimera displays "increased immunogenicity" when it possesses a greater capacity to elicit an immune response than the corresponding one or more GnRH multimers alone. Such increased immunogenicity can be determined by administering the particular leukotoxin-GnRH polypeptide and GnRH multimer controls to animals, and comparing anti-GnRH antibody titres thus obtained using standard assays such as radioimmunoassays and ELISAs, well known in the art.

"Recombinant" proteins or polypeptides refer to polypeptides produced by recombinant DNA techniques; i.e., produced from cells transformed by an exogenous DNA construct encoding the desired polypeptide. "Synthetic" proteins or polypeptides are those prepared by chemical synthesis.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" another coding sequence when RNA polymerase will transcribe the two coding sequences into mRNA, which is then translated into a chimeric polypeptide encoded by the two coding sequences. The coding sequences need not be contiguous to one another so long as the transcribed sequence is ultimately processed to produce the desired chimeric protein. A control sequence is "operably linked to" a coding sequence when it controls the transcription of the coding sequence.

A control sequence "directs the transcription" of a coding sequence in a cell en RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

Two DNA or polypeptide sequences are "substantially homologous" when at least about 80% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning,* vols I & II, supra; *Nucleic Acid Hybridization,* supra.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

By "vertebrate subject" is meant any member of the subphylum chordata, including, without limitation, mammals such as rodents, cattle, pigs, sheep, goats, horses and man; domestic animals such as dogs and cats; birds, including domestic, wild and game birds such as cocks and hens including chickens, turkeys and other gallinaceous birds. The term does not denote a particular age. Thus, both adult and newborn animals are intended to be covered.

B. General Methods

Central to the instant invention is the discovery that leukotoxin polypeptides, when coupled to selected GnRH polypeptide repeats (or multimers), are able to confer superior immunogenicity to the associated GnRH moieties. In this regard, leukotoxin polypeptides act as carrier proteins which present selected GnRH multimers to a subject's immune system in a highly immunogenic form. Thus, chimeric proteins constructed under the invention may be formulated into vaccine compositions which provide enhanced immunogenicity to GnRH polypeptides presented therewith. Fusion of the leukotoxin gene to selected GnRH polypeptides also facilitates purification of the chimeric protein from cells expressing the same.

Accordingly, exemplified herein are leukotoxin chimeras which include leukotoxin fused to more than one GnRH polypeptide. Particular embodiments of the present invention include chimeras comprising a leukotoxin polypeptide fused to one or more GnRH multimers, wherein said multimers have at least one repeating GnRH decapeptide sequence, or at least one repeating unit of a sequence corresponding to at least one epitope of a selected GnRH molecule. Further, the selected GnRH peptide sequences may all be the same, or may correspond to different derivatives, analogues, variants or epitopes of GnRH so long as they retain the ability to elicit an immune response. A representative nucleotide sequence of a GnRH decapeptide is depicted in FIG. 1A. The subject GnRH sequence is modified by the substitution of a glutamine residue at the N-terminal in place of pyroglutamic acid which is found in the native sequence. This particular substitution renders a molecule that retains the native glutamic acid structure but also preserves the uncharged structure of pyroglutamate. Accordingly, the resulting peptide does not require cyclization of the glutamic acid residue and may be produced in the absence of conditions necessary to effect cyclization.

Because the GnRH sequence is relatively short, it can easily be generated using synthetic techniques, as described in detail below. Under the invention, a leukotoxin polypeptide sequence is used to confer immunogenicity upon associated GnRH polypeptides (as a carrier protein) in order to help elicit an adequate immune response toward endogenous GnRH in a vertebrate subject. In this manner, immunization with GnRH can regulate fertility in a vaccinated subject by disruption of estrous cycles or spermatogenesis. A detailed discussion of GnRH can be found in U.S. Pat. No. 4,975, 420, which is incorporated herein by reference in its entirety.

It is a particular object of the invention to provide a reliable and effective alternative to invasive sterilization procedures currently practiced in domestic and farm animal husbandry, such as surgical castration, surgical ovariohysterectomy and the like. Immunosuppression of reproductive activity in vertebrate subjects using leukotoxin-GnRH chimeras constructed according to the present invention provides an effective alternative in that the constructs effect uniform inactivation of reproductive activity in immunized animals. In this regard, a suitable sterilization vaccine product must serve to uniformly inactivate reproductive capabilities in individual animals in response to a minimum of vaccinations in order to provide a successful alternative to surgical procedures. This feature is particularly important for immunosterilization of herd animals, and particularly where it is desired to immunocastrate male piglets to prevent "boar taint" which is produced by the synthesis of sex steroids in normally functioning testicles of male piglets. See e.g. Meloen et al., Vaccine (1994) 12(8):741–746. Prior attempts at developing such a product have not produced uniform results due to the insufficient immunogenicity of GnRH peptides and/or related carrier systems, and the resultant inability of various prior GnRH-based vaccines to induce sufficient immune responses toward endogenous GnRH.

It is also a particular object of the invention to provide a method for reducing the incidence of mammary tumors in mammalian subjects by using the leukotoxin-GnRH fusion molecules produced herein in a vaccine to block GnRH-regulated ovarian functions such as the production of the ovarian hormones estrogen and progesterone in vaccinated subjects. The role of estrogen and progesterone in the etiology of mammary tumors is well established. These ovarian steroids are important in the early stages of the cancer, but once the mammary tumors become established, some tumors become steroid independent. See e.g., the Textbook of Endocrinology, 7th Edition, Wilson et al. (eds), (1985) pp 68–69. Estrogen and progesterone are also known to be carcinogenic and primarily responsible for mammary tumors in dogs.

Accordingly, leukotoxin-GnRH polypeptide chimeras contemplated herein comprise one or more GnRH portions having a plurality of selected GnRH polypeptide sequences in order to render a more immunogenic GnRH peptide antigen. This feature is based on the recognition that endogenous proteins in general may be rendered effective autoantigens by multimerization of their epitopes as described in detail above. More particularly, the GnRH portions of the present leukotoxin-GnRH chimeras may comprise either multiple or tandem repeats of selected GnRH sequences, multiple or tandem repeats of selected GnRH epitopes, or any conceivable combination thereof. GnRH epitopes may be identified using techniques as described in detail above, or fragments of GnRH proteins may be tested for immunogenicity and active fragments used in compositions in lieu of the entire polypeptide. When more than one GnRH multimers are included in the chimeric molecules, each GnRH portion can be the same or different from other included GnRH portions in the molecule.

The sequence of one particular GnRH portion used herein is depicted in FIG. 1B wherein four GnRH sequences, indicated at (1), (2), (3) and (4) respectively, are separated by triplet amino acid spacer sequences comprising various combinations of serine and glycine residues. In the subject oligomer, every other GnRH sequence (those indicated at (2) and (4), respectively) contains a non-conservative amino acid substitution at the second position of the GNRH decapeptide comprising an Asp residue in place of the His residue found in the native GnRH sequence. The alternating GnRH multimeric sequence thus produced renders a highly immunogenic GnRH antigen peptide for use in the fusion proteins of the invention. Other GnRH analogues corresponding to any single or multiple amino acid additions, substitutions and/or deletions are also particularly contemplated herein for use in either repetitive or alternating multimeric sequences. In one particular leukotoxin-GnRH fusion, four copies of the GnRH portion depicted in FIG. 1B are fused to a leukotoxin molecule such that the leukotoxin molecule is flanked on its N- and C-terminus with two copies of the subject GnRH multimer.

Furthermore, the particular GnRH portion depicted in FIG. 1B contains spacer sequences between the GnRH moieties. The strategic use of various spacer sequences between selected GnRH polypeptides is used herein to confer increased immunogenicity on the subject constructs. Accordingly, under the invention, a selected spacer sequence may encode a wide variety of moieties of one or more amino acids in length. Selected spacer groups may preferably provide enzyme cleavage sites so that the expressed chimera can be processed by proteolytic enzymes in vivo (by APC's or the like) to yield a number of peptides, each of which contain at least one T-cell epitope derived from the carrier portion (leukotoxin portion), and which are preferably fused to a substantially complete GNRH polypeptide sequence. The spacer groups may be constructed so that the junction region between selected GnRH moieties comprises a clearly foreign sequence to the immunized subject, thereby conferring enhanced immunogenicity upon the associated GnRH peptides. Additionally, spacer sequences may be constructed so as to provide T-cell antigenicity, such as those sequences which encode amphipathic and/or α-helical peptide sequences which are generally recognized in the art as providing immunogenic helper T-cell epitopes. The choice of particular T-cell epitopes to be provided by such spacer sequences may vary depending on the particular vertebrate species to be vaccinated. Although particular GnRH portions are exemplified which include spacer sequences, it is also an object of the invention to provide one or more GnRH multimers comprising directly adjacent GnRH sequences (without intervening spacer sequences).

The leukotoxin-GnRH polypeptide complex can be conveniently produced recombinantly as a chimeric protein. The GnRH portions of the chimera can be fused 5' and/or 3' to the leukotoxin portion of the molecule, one or more GnRH portions may be located at sites internal to the leukotoxin molecule, or the chimera can comprise any combination of GnRH portions at such sites. The nucleotide sequence coding for full-length *P. haemolytica* A1 leukotoxin has been determined. See, e.g., Lo, *Infect. Immun.* (1987) 55:1987–1996; U.S. Pat. No. 5,055,400, incorporated herein by reference in its entirety. Additionally, several variant leukotoxin gene sequences are disclosed herein.

Similarly, the coding sequences for porcine, bovine and ovine GnRH have been determined, (Murad et al., *Hormones and Hormone Antagonists,* in *The Pharmacoloqical Basis of Therapeutics,* Sixth Edition (1980)), and the cDNA for human GnRH has been cloned so that its sequence has been well established (Seeburg et al., *Nature* (1984) 311:666–668). Additional GnRH polypeptides of known sequences have been disclosed, such as the GnRH molecule occurring in salmon and chickens (International Publication No. WO 86/07383, published Dec. 18, 1986). The GnRH coding sequence is highly conserved in vertebrates, particularly in mammals; and porcine, bovine, ovine and human GnRH sequences are identical to one another. The desired leukotoxin and GnRH genes can be cloned, isolated and ligated together using recombinant techniques generally known in the art. See, e.g., Sambrook et al., supra.

Alternatively, DNA sequences encoding the chimeric proteins can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature* (1981) 292:756; Nambair et al. *Science* (1984) 223:1299; Jay et al. *J. Biol. Chem.* (1984) 259:6311.

Once coding sequences for the chimeric proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning:* Vols. I & II, supra; T. Maniatis et al., supra; B. Perbal, supra.

The fusion gene can be placed under the control of a promoter, ribosome binding site (for bacterial expression) and, optionally, an operator (collectively referred to herein as "control" elements), so that the DNA sequence encoding the chimeric protein is transcribed into RNA in the host cell transformed by a vector containing this expression construction. The coding sequence may or may not contain a signal peptide or leader sequence. The chimeric proteins of the present invention can be expressed using, for example, native *P. haemolytica* promoter, the *E. coli* tac promoter or the protein A gene (spa) promoter and signal sequence. Leader sequences can be removed by the bacterial host in post-translational processing. See, e.g., U.S. Pat. Nos. 4,431, 739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular fusion coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular chimeric protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogues of the chimeric proteins of interest. Mutants or analogues may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning,* Vols. I and II, supra; *Nucleic Acid Hybridization,* supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The chimeric protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

The chimeric proteins of the present invention may also be produced by chemical synthesis, such as by solid phase peptide synthesis, based on the determined amino acid sequences. Such methods are known to those skilled in the art. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology,* editors E. Gross and J. Meienhofer, Vol. 2, Academic Press, New York, (1980), pp. 3–254, for solid phase peptide synthesis techniques; and M. Bodansky, *Principles of Peptide Synthesis,* Springer-Verlag, Berlin (1984) and E. Gross and J. Meienhofer, Eds., *The Peptides: Analysis, Synthesis, Biology,* supra, Vol. 1, for classical solution synthesis.

Subjects can be immunized against endogenous GnRH by administration of vaccine compositions which include the present chimeric leukotoxin-GnRH proteins. Prior to immunization, it may be desirable to further increase the immunogenicity of a particular chimeric protein. This can be accomplished in any one of several ways known to those of skill in the art. For example, the leukotoxin-GnRH polypeptide fusion protein may be administered linked to a secondary carrier. For example, a fragment may be conjugated with a macromolecular carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or selected GnRH polypeptides) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the chimeric proteins of the present invention include VP6 polypeptides of rotaviruses, or functional fragments thereof, as disclosed in U.S. Pat. No. 5,071,651, and incorporated herein by reference. Also useful is a fusion product of a viral protein and a leukotoxin-GnRH immunogen, where that fusion product is made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the fusion proteins of the present invention may be coupled to erythrocytes, preferably the subject's own erythrocytes. Methods of coupling peptides to proteins or cells are known to those of skill in the art.

The chimeric proteins of the instant invention can also be administered via a carrier virus which expresses the same. Carrier viruses which will find use herein include, but are not limited to, the vaccinia and other pox viruses, adenovirus, and herpes virus. By way of example, vaccinia virus recombinants expressing the novel chimeric proteins can be constructed as follows. The DNA encoding the particular leukotoxin-GnRH chimeric protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant chimeric protein into the viral genome. The resulting TK-recombinant can be selected by culturing the cells in the presence of 5-bromodeoxyuridine and picking viral plaques resistant thereto.

It is also possible to immunize a subject with the present chimeric proteins, either administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., *Reminqton's Pharmaceutical Sciences,* Mack Publishing Company, Easton, Pa., 18th edition, 1990. The composition or formulation to be administered will, in any event, contain a quantity of the protein adequate to achieve the desired immunized state in the subject being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 1% to about 30% of the active ingredient, preferably about 2% to about 20%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the chimeric proteins into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The chimeric proteins can also be presented using implanted mini-pumps, well known in the art.

Furthermore, the chimeric proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, a selected GnRH-leukotoxin chimera is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired.

With the present vaccine formulations, approximately 1 $\mu$g to 1 mg, more generally 5 $\mu$g to 200 $\mu$g of GnRH polypeptide per mL of injected solution, should be adequate to raise an immunological response when administered. In this regard, the ratio of GnRH to leukotoxin in the Leukotoxin-GnRH antigens of the subject vaccine formulations will vary based on the particular leukotoxin and GnRH polypeptide moieties selected to construct those molecules. More particularly, in the leukotoxin-GnRH polypeptides used in producing the vaccine formulations under the invention, there will be about 1 to 40% GnRH, preferably about 3 to 30% and most preferably about 7 to 27% GnRH polypeptide per fusion molecule. Increases in the percentage of GnRH present in the LKT-GnRH antigens reduces the amount of total antigen which must be administered to a subject in order to elicit an effective B-cell response to GnRH. Effective dosages can be readily established by one of ordinary skill in the art through routine trials establishing dose response curves. The subject is immunized by administration of the particular leukotoxin-GnRH polypeptide in at least one dose, and preferably two doses. Moreover, the animal may be administered as many doses as is required to maintain a state of immunity.

Below are examples of specific embodiments for carrying out the present invention. The examples are offered for illustrative purposes only, and are not intended to limit the scope of the present invention in any way.

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T_4$ DNA ligase, *E. coli*, DNA polymerase I, Klenow fragment, and other biological reagents were purchased from commercial suppliers and used according to the manufacturers' directions. Double-stranded DNA fragments were separated on agarose gels.

cDNA and genomic libraries were prepared by standard techniques in pUC13 and the bacteriophage lambda gt11, respectively. See DNA CLONING: Vols I and II, supra.

*P. haemolytica* biotype A, serotype 1 ("A1") strain B122 was isolated from the lung of a calf which died of pneumonic pasteurellosis and was stored at −70° C. in defibrinated blood. Routine propagation was carried out on blood agar plates or in brain heart infusion broth (Difco Laboratories, Detroit, Mich.) supplemented with 5% (v/v) horse serum (Gibco Canada Ltd., Burlington, Canada). All cultures were incubated at 37° C.

EXAMPLE 1

Isolation of *P. haemolytica* Leukotoxin Gene

To isolate the leukotoxin gene, gene libraries of *P. haemolytica* A1 (strain B122) were constructed using standard techniques. See, Lo et al., *Infect. Immun.*, supra; *DNA CLONING: Vols. I and II*, supra; and Sambrook et al., supra. A genomic library was constructed in the plasmid vector pUC13 and a DNA library constructed in the bacteriophage lambda gt11. The resulting clones were used to transform *E. coli* and individual colonies were pooled and screened for reaction with serum from a calf which had survived a *P. haemolytica* infection and that had been boosted with a concentrated culture supernatant of *P. haemolytica* to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See, Lo et al., *Infect. Immun.*, supra. To confirm this, smaller fragments were re-cloned and the restriction maps compared. It was determined that approximately 4 kilobase pairs of DNA had been cloned. Progressively larger clones were isolated by carrying out a chromosome walk (5' to 3' direction) in order to isolate full-length recombinants which were approximately 8 kb in length. The final construct was termed pAA114. This construct contained the entire leukotoxin gene sequence.

lktA, a MaeI restriction endonuclease fragment from pAA114 which contained the entire leukotoxin gene, was treated with the Klenow fragment of DNA polymerase I plus nucleotide triphosphates and ligated into the SmaI site of the cloning vector pUC13. This plasmid was named pAA179. From this, two expression constructs were made in the ptac-based vector pGH432:lacI digested with SmaI. One, pAA342, consisted of the 5'-AhaIII fragment of the lktA gene while the other, pAA345, contained the entire MaeI fragment described above. The clone pAA342 expressed a truncated leukotoxin peptide at high levels while pAA345 expressed full length leukotoxin at very low levels. Therefore, the 3' end of the lktA gene (StyI BamHI fragment from pAA345) was ligated to StyI BamHI-digested pAA342, yielding the plasmid pAA352. The structure of pAA352 is shown in FIG. 2 and the nucleotide sequence and predicted amino acid sequence of *P. haemolytica* leukotoxin produced from the pAA352 construct (hereinafter LKT 352) is shown in FIG. 3.

Several truncated versions of the leukotoxin gene were expressed from pAA114. These truncated forms were fusions with the B-galactosidase (lacZ) gene. Two fragments, LTX1.1 and LTX3.2, from an EcoRV Pst1 double digest, were isolated from pAA114 as purified restriction fragments (1.0 kb and 2.1 kb, respectively). These fragments were cloned into the cloning vector pTZ18R that had been digested with HincII and Pst1. The resulting vector, termed pLTX3P.1, was used to transform *E. coli* strain JM105. Transformed cells were identified by plating on media containing ampicillin plus Xgal and IPTG. Blue colonies indicated the presence of a functional lacZ gene. DNA from the transformed cells was analyzed by restriction endonuclease digestion and found to contain the 5' end of the leukotoxin gene (lktC and lktA).

A leukotoxin EcoRV/Pst1 5'-fragment (from pLTX3P.1) was subcloned into the cloning vector pBR325 that had been digested with EcoR1 and Pst1. The pBR325 plasmid also contained the native leukotoxin promoter (obtained from pLTX3P.1) and a promoterless, full length lacZ gene. The resulting construct was used to transform *E. coli* JM105 and blue colonies were isolated from Xgal agar. The new construct was termed pAA101 (ATCC No. 67883) and is depicted in FIG. 10. The predicted amino acid sequence of the *P. haemolytica* leukotoxin produced from the pAA101 construct (hereinafter LKT 101) is depicted in FIG. 11.

EXAMPLE 2

Construction of LKT-GnRH Fusions

Representative LKT-GnRH fusions were constructed as follows. Oligonucleotides containing sequences corresponding to single copy GnRH and GnRH as four multiple repeats were constructed on a Pharmacia Gene Assembler using standard phosphoramidite chemistry. The sequences of these oligonucleotides are shown in FIGS. 1A and 1B. The subject oligonucleotides were annealed and ligated into the vector pAA352 (ATCC No. 68283, and described above), which had been digested with the restriction endonuclease BamH1. This vector contains the *P. haemolytica* leukotoxin gene. The ligated DNA was used to transform *E. coli* strain MH3000. Transformants containing the oligonucleotide inserts were identified by restriction endonuclease mapping.

Figure 4:
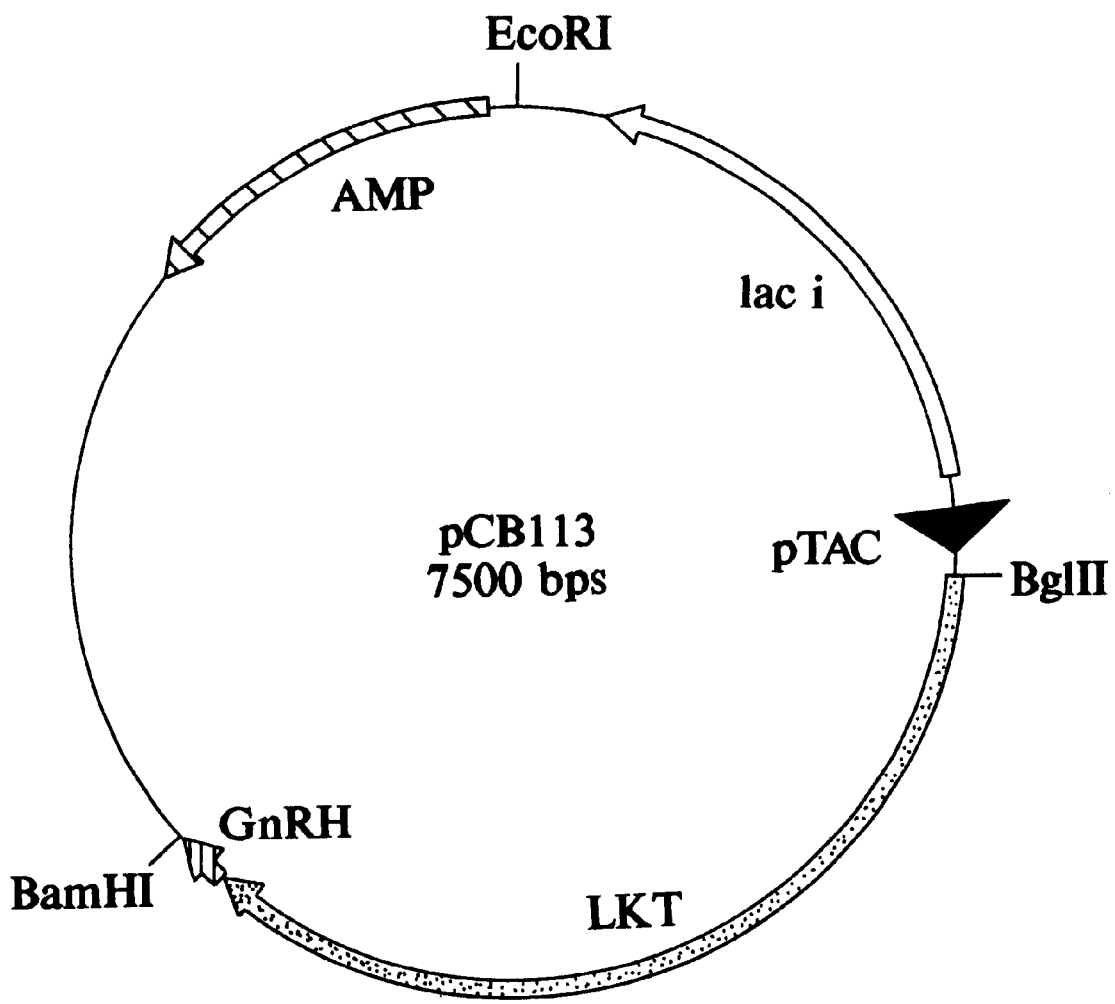
FIG. 4 shows the structure of Plasmid pCB113 carrying a leukotoxin-GnRH (LKT-GnRH) gene fusion.

An eight copy GnRH tandem repeat sequence was prepared by annealing the four copy GnRH oligonucleotides and ligating them into a vector which had been digested with the restriction endonuclease BamH1. The oligomers were designed to disable the upstream BamH1 site when inserted and to ensure that the insertion of additional copies of the oligomer would be oriented in the proper reading frame. The sequence of the subject oligonucleotide is shown in FIG. 1B. Plasmid DNA from the *E. coli* MH3000 strain was then isolated and used to transform the strain JM105. The recombinant plasmids were designated pCB113 (LKT 352:4 copy GnRH, ATCC Accession No. 69749) and pCB112 (LKT 352:8 copy GnRH). Recombinant plasmid pCB113 is shown in FIG. 4, plasmid pCB112 is identical to pCB113 except that the multiple copy GnRH sequence (corresponding to the oligomer of FIG. 1B) was inserted twice as described above. The nucleotide sequence of the recombinant LKT-GnRH fusion of pCB113 is shown in FIG. 5. The nucleotide sequence of the recombinant LKT-GnRH fusion pCB112 is identical except that the multiple copy GnRH sequence was inserted twice.

EXAMPLE 3

Construction of Shortened LKT Carrier Peptide

A shortened version of the recombinant leukotoxin peptide was constructed from the recombinant gene present on the plasmid pAA352 (as described above). The shortened LKT gene was produced by deleting an internal DNA fragment of approximately 1300 bp in length from the recombinant LKT gene as follows.

The plasmid pCB113, (ATCC Accession No. 69749) which includes the LKT 352 polypeptide fused to four copies of the GnRH polypeptide, was digested with the restriction enzyme BstB1 (New England Biolabs). The resultant linearized plasmid was then digested with mung-bean nuclease (Pharmacia) to remove the single stranded protruding termini produced by the BstB1 digestion. The blunted DNA was then digested with the restriction enzyme Nae1 (New England Biolabs), and the digested DNA was loaded onto a 1% agarose gel where the DNA fragments were separated by electrophoresis. A large DNA fragment of approximately 6190 bp was isolated and purified from the agarose gel using a Gene Clean kit (Bio 101), and the purified fragment was allowed to ligate to itself using bacteriophage T4 DNA ligase (Pharmacia). The resulting ligation mix was used to transform competent *E. coli* JM105 cells, and positive clones were identified by their ability to produce an aggregate protein having a molecular weight of approximately 57 KDa. The recombinant plasmid thus formed was designated pCB111, (ATCC Accession No. 69748), and produces a shortened leukotoxin polypeptide (hereinafter referred to as LKT 111) fused to four copies of GnRH polypeptide. The structure of pCB111 is shown in FIG. 6. Plasmid pCB114 is identical to pCB111 except that the multiple copy GnRH sequence (corresponding to the oligomer of FIG. 1B) was inserted twice. The nucleotide sequence of the recombinant LKT-GnRH fusion of pCB111 is shown in FIG. 7, the nucleotide sequence of the recombinant LKT-GnRH fusion of pCB114 is identical except that the multiple copy GNRH sequence was inserted twice.

The nucleotide sequence of the ligation fusion point of the subject clones has been confirmed by sequencing with a bacteriophage T7 polymerase sequencing kit (Pharmacia). The nucleotide sequences of these fusion points are shown in FIG. 8.

EXAMPLE 4

Construction of an LKT-GnRH Fusion Having 8 Copy Amino Terminal and Carboxyl Terminal GnRH Multimers A recombinant LKT-GnRH fusion molecule having two 8 copy GN RH multimers, one arranged at the N'-terminus of LKT 111 and the other arranged at the C'-terminus of LKT 111, was constructed from the LKT-GnRH fusion sequence obtained from the pCB114 plasmid by ligating the multiple copy GnRH sequence (corresponding to the oligomer of FIG. 1B) twice at the 5' end of the LKT 111 coding sequence. A synthetic nucleic acid molecule having the following nucleotide sequence: 5'-ATGGCTACTGTTATAGATCGATCT-3' (SEQ ID NO:20) was ligated at the 5' end of the multiple copy GnRH sequences. The synthetic nucleic acid molecule encodes an eight amino acid sequence (Met-Ala-Thr-Val-Ile-Asp-Arg-Ser) (SEQ ID NO:21). The resulting recombinant molecule thus contains in the order given in the 5' to 3' direction: the synthetic nucleic acid molecule; a nucleotide sequence encoding a first 8 copy GnRH multimer; a nucleotide sequence encoding the shortened LKT peptide (LKT 111); and a nucleotide sequence encoding a second 8 copy GnRH multimer.

The recombinant molecule was circularized, and the resulting molecule was used to transform competent *E. coli* JM105 cells. Positive clones were identified by their ability to produce an aggregate protein having a molecular weight of approximately 74 KDa. The recombinant plasmid thus formed was designated pCB122 which produces the LKT 111 polypeptide fused to 16 copies of GnRH polypeptide. The nucleotide sequence of the recombinant LKT-GnRH fusion of pCB122 is shown in FIGS. 9-1 through 9-6.

EXAMPLE 5

Purification of LKT-antigen Fusions

The recombinant LKT-GnRH fusions from Examples 2, 3 and 4 were purified using the following procedure. For each fusion, five to ten colonies of the transformed *E. coli* strains were inoculated into 10 mL of TB broth supplemented with 100 micrograms/mL of ampicillin and incubated at 37° C. for 6 hours on a G10 shaker, 220 rpm. Four mL of this culture was diluted into each of two baffled Fernbach flasks containing 400 mL of TB broth+ampicillin and incubated overnight as described above. Cells were harvested by centrifugation for 10 minutes at 4,000 rpm in polypropylene bottles, 500 mL volume, using a Sorvall GS3 rotor. The pellet was resuspended in an equal volume of TB broth containing ampicillin which had been prewarmed to 37° C. (i.e., 2×400 ml), and the cells were incubated for 2 hours as described above.

3.2 mL of isopropyl-B,D-thiogalactopyranoside (IPTG, Gibco/BRL), 500 mM in water (final concentration=4 mM), was added to each culture in order to induce synthesis of the recombinant fusion proteins. Cultures were incubated for two hours. Cells were harvested by centrifugation as described above, resuspended in 30 mL of 50 mM Tris-hydrochloride, 25% (w/v) sucrose, pH 8.0, and frozen at −70° C. The frozen cells were thawed at room temperature after 60 minutes at −70° C., and 5 mL of lysozyme (Sigma, 20 mg/mL in 250 mM Tris-HCl, pH 8.0) was added. The mixture was vortexed at high speed for 10 seconds and then placed on ice for 15 minutes. The cells were then added to 500 mL of lysis buffer in a 1000 mL beaker and mixed by stirring with a 2 mL pipette. The beaker containing the lysed cell suspension was placed on ice and sonicated for a total of 2.5 minutes (5–30 second bursts with 1 minute cooling between each) with a Braun sonicator, large probe, set at 100 watts power. Equal volumes of the solution were placed in Teflon SS34 centrifuge tubes and centrifuged for 20 minutes at 10,000 rpm in a Sorvall SS34 rotor. The pellets were resuspended in a total of 100 mL of sterile double distilled water by vortexing at high speed, and the centrifugation step repeated. Supernatants were discarded and the pellets combined in 20 mL of 10 mM Tris-HCl, 150 mM NaCl, pH 8.0 (Tris-buffered saline) and the suspension frozen overnight at −20° C.

The recombinant suspension was thawed at room temperature and added to 100 mL of 8 M Guanidine HCl (Sigma) in Tris-buffered saline and mixed vigorously. A magnetic stir bar was placed in the bottle and the solubilized sample was mixed at room temperature for 30 minutes. The solution was transferred to a 2000 mL Erlenmeyer flask and 1200 mL of Tris-buffered saline was added quickly. This mixture was stirred at room temperature for an additional 2 hours. 500 mL aliquots were placed in dialysis bags (Spectrum, 63.7 mm diameter, 6,000–8,000 MW cutoff, #132670, from Fisher scientific) and these were placed in 4,000 mL beakers containing 3,500 mL of Tris-buffered saline+0.5 M Guanidine HCl. The beakers were placed in a 4° C. room on a magnetic stirrer overnight after which dialysis buffer was replaced with Tris-buffered saline+0.1 M Guanidine HCl and dialysis continued for 12 hours. The buffer was then replaced with Tris-buffered saline+0.05 M Guanidine HCl and dialysis continued overnight. The buffer was replaced with Tris-buffered saline (no guanidine), and dialysis continued for 12 hours. This was repeated three more times. The final solution was poured into a 2000 mL plastic roller bottle (Corning) and 13 mL of 100 mM PMSF (in ethanol) was added to inhibit protease activity. The solution was stored at −20° C. in 100 mL aliquots.

To confirm that the fusion proteins had been isolated, aliquots of each preparation were diluted 20-fold in double distilled water, mixed with an equal volume of SDS-PAGE sample buffer, placed in a boiling water bath for five minutes and run through 12% polyacrylamide gels. Recombinant leukotoxin controls were also run.

All fusion proteins were expressed at high levels as inclusion bodies. The predicted molecular weights based on the DNA sequences of the fusion proteins were 104,869 (LKT 352::4 copy GnRH, from pCB113); 110,392 (LKT 352::8 copy GnRH, from pCB112); 57,542 (LKT 111::4 copy GnRH, from pCB111); 63,241 (LKT 111::8 copy GnRH from pCB114); and 73,886 (8 copy GnRH::LKT 111::8 copy GnRH from pCB122). The predicted molecular weight of the recombinant LKT 352 molecule was 99,338, and the predicted molecular weight of the recombinant LKT 111 molecule was 51,843.

EXAMPLE 6

In Vivo Immunologic Activity of LKT-GnRH Fusions

To test for the ability of LKT-GnRH fusions to induce an anti-GnRH immunological response in vivo, and to compare this response to other GnRH carrier conjugates, the following vaccination trial was performed. Three groups of 8 male pigs, approximately 8 weeks of age (35–50 kg) were used which were Specific Pathogen Free. The animals were maintained in a minimal disease facility and were vaccinated on days 0 and 21 of the trial with the following formulations:

Group 1—placebo which consisted of saline formulated in Emulsigen Plus adjuvant containing 15 mg of dimethyldioctadecylammonium bromide (DDA) (2 ml);

Group 2—LKT 352-GnRH (250 µg LKT, prepared as described in the previous examples) formulated in the same adjuvant (2 ml);

Group 3—VP6-GnRH, 0.5 µg VP6 and 5 µg GnRH, formulated in the same adjuvant (2 ml). The VP6 preparation was made as described in U.S. Pat. No. 5,071,651, using the binding peptide described therein.

Blood samples were taken on days 0, 21 and 35, allowed to clot, centrifuged at 1500 g, and the serum removed. The serum antibody titres against GnRH were measured using the RIA procedure of Silversides et al., *J. Reprod. Immunol.* (1985) 7:171–184.

The results of this trial indicated that only those animals immunized with the LKT 352-GnRH formulation produced significant titres against GnRH (titres >1:70). Neither the placebo nor the VP6-GnRH groups produced anti-GnRH titres. Previously, multiple vaccinations with doses of GnRH of more than 100 µg, conjugated to other carrier proteins, were required to induce anti-hormone titres. These results indicate that the LKT-GnRH carrier system provides a greatly improved immunogen over prior carrier systems.

1:1000 using a standard radioimmunoassay procedure. If less than 5% of the iodinated GnRH was bound, antibody was deemed to be undetectable. The antibody titres thus obtained are summarized in the Table 1.

The results of this study indicate that equal doses of GnRH presented as multiple tandem repeats (four or eight copy GnRH) gave a dramatic improvement in antibody production over single copy GnRH (as measured by binding to iodinated native GnRH). Further, the above results indicate that a fusion protein comprising a four copy GnRH tandem repeat ligated to LKT 352 represents an effective immunogenic GnRH antigen form, although immunogenicity may be influenced by dose or subject species.

TABLE 1

| | Group 1 LKT 352::1 Copy GnRH | | | | Group 2 LKT 352::4 Copy GnRH | | | | Group 3 LKT 352::8 Copy GnRH | | | |
| --- | --- | --- | --- | --- | --- | --- | --- | --- | --- | --- | --- | --- |
| | No. responding | | mean response (%)* | | No. responding | | mean response (%)* | | No. responding | | mean response (%)* | |
| Sample Day | 1:100 | 1:1000 | 1:100 | 1:1000 | 1:100 | 1:1000 | 1:100 | 1:1000 | 1:100 | 1:1000 | 1:100 | 1:1000 |
| 23 | 0 | 0 | — | — | 3 | 1 | 16 | 9 | 2 | 0 | 33 | — |
| 35 | 2 | 2 | 45 | 20 | 9 | 9 | 75 | 30 | 7 | 5 | 48 | 41 |
| 44 | 2 | 2 | 60 | 39 | 10 | 10 | 55 | 43 | 8 | 7 | 57 | 46 |

*mean response is the average binding of $I^{125}$-GnRH of only those animals with binding in excess of 5%.

EXAMPLE 8

In Vivo Immunologic Activity and Biologic Effect of LKT 352::GnRH and LKT 111::GnRH Fusions To test the ability of fusion proteins comprising multiple tandem repeats of GnRH (ligated to either LKT 352 or LKT 111) to elicit an anti-GnRH immunological response in vivo and to manifest a biologic effect in vivo, the following vaccination trial was preformed. Cultures of *E. coli* containing plasmids pCB113 and pCB111 (4 copy GnRH ligated to LKT 352 or LKT 111, respectively) were prepared as described above. Vaccines from each of the above cultures were formulated to contain the equivalent of 5 µg of GnRH in 0.2 mL of VSA-3 adjuvant, (a modified Emulsigen Plus adjuvant), with a control vaccine comprising 0.2 mL of the adjuvant also being prepared. Three groups of 5 male Swiss mice were given two subcutaneous injections 21 days apart, with the initial injections (day 0) given at 5–6 weeks of age. On day 49 the subjects were sacrificed.

Immunological activity of the subject GnRH-LKT fusions was assayed by measuring anti-GnRH antibody titres using a standard radioimmunoassay procedure at a 1:1000 serum dilution. Biological effect of the GnRH-LKT fusions was quantified by standard radioimmunoassay of serum testosterone levels with a sensitivity of 25 pg/ml, and testicular tissue was weighed and histologically examined. The results of this trial are summarized in Table 2.

EXAMPLE 7

In Vivo Immunologic Effect of Multiple Tandem GnRH Repeats Ligated to LKT

To test for the ability of recombinant LKT-GnRH fusion proteins containing multiple GnRH polypeptide repeats to induce an anti-GnRH immunological response in vivo, the following vaccination trial was performed. Cultures of *E. coli* containing plasmids pCB113 and pCB175 (having 4 and 8 copies of GnRH ligated to LKT 352, respectively) and a plasmid having 1 copy of GnRH ligated to LKT 352 were prepared as described above. Vaccines from each of the above cultures were formulated to contain the equivalent of 5 µg of GnRH in 0.2 mL of Emulsigen Plus. Three groups of 10 female mice were given two subcutaneous injections 23 days apart and blood samples were collected at days 23, 35 and 44 after the primary injection. Serum antibody titres against GnRH were measured at final dilutions of 1:100 and In the trial, all animal subjects injected with GnRH:LKT antigens had readily detectable antibody levels; however, the LKT 111::GnRH fusion (from plasmid pCB111) showed superior immunogenicity as indicated by uniformity of response and titre. Serum testosterone (produced by the testicular Leydig cells) is secreted in a pulsatile manner, and accordingly, low values and extreme variability of serum levels are expected in normal animal subjects. Under the trial, the control group (receiving the 0.2 mL adjuvant vaccine injections) had normal serum testosterone levels, while both groups of treated subjects had essentially undetectable serum testosterone.

Further under the trial, histological evaluation of testicular tissue revealed varying degrees of Leydig cell atrophy, reduced seminiferous tubule diameter and interruption of spermatogenesis in treated subjects; however, testicular weight remained close to normal in treated animals—even in the presence of high anti-GnRH antibody titres—although there was clear evidence of testicular regression in 2 of 5 subjects receiving the LKT 111::4 copy GnRH fusions.

Accordingly, these results show that multiple copies of GnRH ligated to either LKT 352 or LKT 111 comprise potent immunogens; and further, it is indicated that vaccination with the subject fusion proteins triggers production of antibodies which are able to neutralize endogenous GnRH in vivo, and that a concomitant in vivo biological effect is discernable in animal subjects receiving such vaccinations.

were administered in VSA-3 adjuvant in a 2.0 mL volume. Four groups of 5 male and 5 female weanling pigs, 35 days old (at day 0), were injected at day 0 and reinjected at day 21 of the trial. Blood samples were collected at days 0, 21 and 35, with anti-GnRH antibody titres being measured at a final dilution of 1:1000 using a standard radioimmunoassay procedure. The assay results are summarized in Table 3.

Under the trial, anti-GnRH antibodies could not be detected in any subjects prior to immunization, but were readily detected in most subjects by day 35 (one subject in treatment group 4 died due to an infection unrelated to treatment). The results in this trial indicate that fusion proteins comprising multiple GnRH repeats ligated to either a LKT 352 or LKT 111 carrier polypeptide form useful immunogens in porcine subjects. Based on the predicted

TABLE 2

|  | Group 1 Control | | | Group 2 5 μg LKT 352::4 Copy GnRH | | | Group 3 5 μg LKT 111::4 Copy GnRH | | |
| --- | --- | --- | --- | --- | --- | --- | --- | --- | --- |
| Animal | Antibody Titre* | Testicular Wt. (mg) | Serum Testosterone† | Antibody Titre* | Testicular Wt. (mg) | Serum Testosterone† | Antibody Titre* | Testicular Wt. (mg) | Serum Testosterone† |
| 1 | 7.0 | 252 | .04 | 73.0 | 282 | .13 | 75.0 | 163 | .00 |
| 2 | 4.0 | 327 | .18 | 14.0 | 334 | .10 | 59.0 | 296 | .07 |
| 3 | 0.0 | 276 | 2.73 | 18.0 | 2S4 | .03 | 54.0 | 260 | .24 |
| 4 | 0.0 | 220 | .36 | 55.0 | 222 | .05 | 66.0 | 26S | .03 |
| 5 | 1.0 | 232 | 1.44 | 61.0 | 226 | .19 | 64.0 | 50 | .00 |
| Mean | 2.4 | 261 | .95 | 44 | 263 | .10 | 64 | 206 | .07 |
| Std Error | 1.4 | 19 | .51 | 12 | 21 | .03 | 4 | 45 | .04 |

*% Binding of $I^{125}$-GnRH at a 1:1000 serum dilution
†ng/ml

EXAMPLE 9

In Vivo Immunologic Activity of LKT::GnRH Fusions in Porcine Sublects

To test the ability of fusion proteins comprising multiple tandem repeats of GnRH (ligated to either LKT 352 or LKT 111) to elicit anti-GnRH immunological response in vivo in porcine subjects, the following vaccination trial was preformed. Cultures of *E. coli* containing plasmids pCB113, pCB111, pCB175 and pCB114 (LKT 352::4 copy GnRH, LKT 111::4 copy GnRH, LKT 352::8 copy GnRH, and LKT 111::8 copy GnRH, respectively) were prepared as described above. Vaccines from each of the above cultures were formulated to contain the equivalent of 50 μg GnRH and molecular weights of the decapeptide GnRH (1,200), the LKT 111 polypeptide (52,000) and the LKT 352 polypeptide (100,000), the percentages of GnRH in the LKT-GnRH antigen fusions are as follows: 4.9% (LKT 352::4 copy GnRH); 8.5% (LKT 111::4 copy GnRH); 9.3% (LKT 352::8 copy GnRH) and 15.7% (LKT 111::8 copy GnRH). Accordingly, the practical result thus obtained indicates that by using LKT-GnRH fusions comprising the LKT 111 polypeptide carrier, the overall amount of antigen (LKT-GnRH) administered to the subject may be halved (as compared to vaccination compositions using the LKT 352 carrier polypeptide system) to obtain an equivalent anti-GnRH response.

TABLE 3

| Animal Number | Group 1 LKT 352::4 copy GnRH 50 μg day 35 1:1000 dilution | Group 2 LKT 111::4 copy GnRH 50 μg day 35 1:1000 dilution | Group 3 LKT 352::8 copy GnRH 50 μg day 35 1:1000 dilution | Group 4 LKT 111::8 copy GnRH 50 μg day 35 1:1000 dilution |
| --- | --- | --- | --- | --- |
| 1 | ♂ 47.7 | ♀ 46.0 | ♂ 68.3 | ♂ 51.0 |
| 2 | ♀ 50.3 | ♂ 71.6 | ♂ 65.1 | ♂ 31.7 |
| 3 | ♀ 66.0 | ♀ 21.4 | ♀ 50.7 | ♀ 35.7 |
| 4 | ♀ 70.2 | ♂ 46.2 | ♂ 4.7 | ♀ 65.9 |
| 5 | ♂ 17.3 | ♀ 48.9 | ♀ 38.3 | ♀ |
| 6 | ♂ 18.3 | ♂ 69.4 | ♀ 17.4 | ♂ 11.3 |
| 7 | ♀ 14.7 | ♂ 47.9 | ♀ 51.4 | ♀ 28.3 |
| 8 | ♂ 37.0 | ♀ 44.4 | ♂ 18.0 | ♂ 43.0 |
| 9 | ♂ 26.0 | ♂ 70.8 | ♂ 83.5 | ♀ 78.7 |
| 10 | ♀ 2.7 | ♀ 37.8 | ♀ 24.2 | ♂ 55.9 |
| Mean | 35.0 | 50.4 | 42.2 | 44.6 |

TABLE 3-continued

|  | Group 1<br>LKT 352::4 copy<br>GnRH 50 μg<br>day 35<br>1:1000<br>dilution | Group 2<br>LKT 111::4 copy<br>GnRH 50 μg<br>day 35<br>1:1000<br>dilution | Group 3<br>LKT 352::8 copy<br>GnRH 50 μg<br>day 35<br>1:1000<br>dilution | Group 4<br>LKT 111::8 copy<br>GnRH 50 μg<br>day 35<br>1:1000<br>dilution |
|---|---|---|---|---|
| Animal Number |  |  |  |  |
| Standard Deviation | 7.3 | 5.1 | 8.1 | 6.9 |
| Responders | 9/10 | 10/10 | 9/10 | 9/9 |

EXAMPLE 10

Evaluation of LKT 111::8 Copy GnRH Immunocastration Vaccine Efficiency

To evaluate the efficacy and commercial usefulness of a vaccine formulation containing the LKT 111::8 copy GnRH fusion protein, the following vaccination trial was carried out. A culture of *E. coli* containing the plasmid pCB114 (LKT 111::8 copy GnRH) was prepared as described above. A vaccine formulation from the above culture was prepared which contained the equivalent of 50 μg GnRH. The vaccine formulation was administered in VSA-3 adjuvant at a 2.0 mL final volume. Three treatment groups, with 30 male pigs (boars) each, were established. The three groups consisted of 30 barrows (boars surgically castrated before sexual maturity), 30 control boars and 30 immunocastrates (boars castrated by vaccination with the GnRH immunogen). At weaning (day 21), the barrow and control boar group animals were injected with placebo (VSA-3 adjuvant alone), while the immunocastrate group was injected with the above-described vaccine formulation. When the animals reached a predetermined weight about 3 weeks before slaughter, the immunocastrate group was given a booster dose of the vaccine, while the barrow and control boar groups were again given placebo injections. Measurements included serum antibody titres to GnRH, blood testosterone levels, carcass traits, animal behavior, feed efficiency, rate of weight gain, and salivary gland and body fat androsterone levels (as a measure of boar taint).

Figure 12:
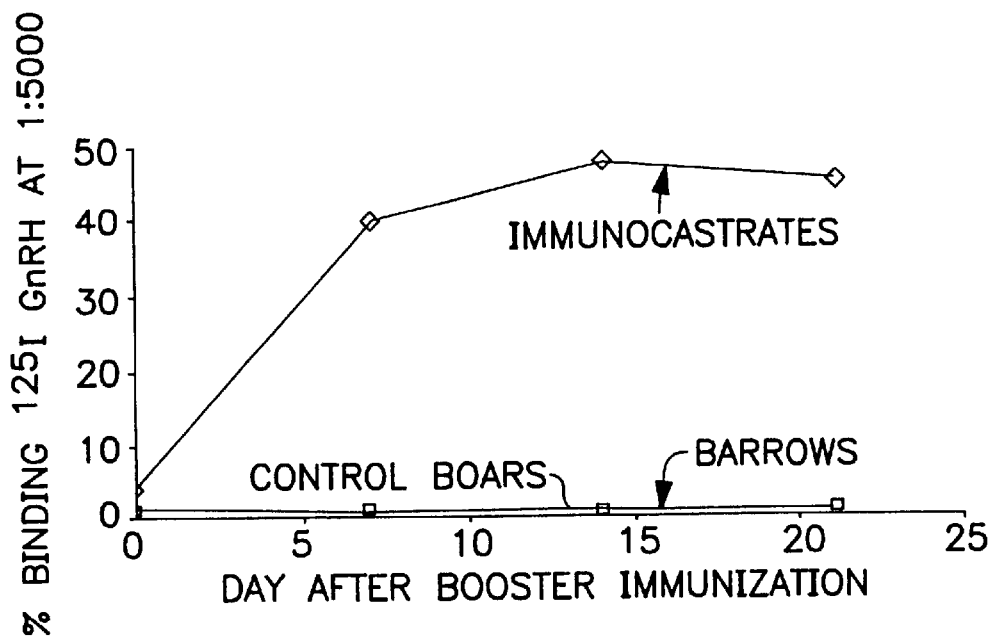
FIG. 12 shows a comparison of average serum anti-GnRH antibody titres in barrows, untreated boars, and immunocastrated boars (vaccinated with leukotoxin-GnRH fusion proteins) as described in Example 10.

(a) Serum Anti-GnRH Antibody Titre:

Immunological activity of the 8 copy GnRH-LKT fusion vaccine formulation was assayed by measuring anti-GnRH antibody titres using a standard radioimmunoassay procedure at a 1:5000 serum dilution. A comparison of serum antibody titres in the three experimental groups is provided in FIG. 12. As can be seen, anti-GnRH antibody titres increased dramatically in the immunocastrate (vaccinated) boars and remained at levels significantly in excess of the minimal amount required to produce a biological effect (approximately 10 to 20% binding in FIG. 12) for over 20 days post vaccination.

(b) Biological Effect of the Immunocastrate Vaccine on Sexual Gland Size:

The biological effect of the 8 copy GnRH-LKT fusion vaccine formulation was determined by comparing the weight and measurements of sexual glands from the control boars and the immunocastrate (vaccinated) boars, as well as by assaying and comparing serum testosterone levels in those two experimental groups. In particular, the bulbourethral glands and testes from the animals were weighed and measured. The results are depicted below in Table 4. As can be seen, the average weight of the bulbourethral glands in the vaccinated animals was reduced approximately 32% relative to the control animals. In addition, the average weight of the testes in the vaccinated animals was reduced approximately 25% relative to the control animals. These results are consistent with reduced testosterone production from the testes in the vaccinated animals.

TABLE 4

|  |  | Bulbourethral Gland | | | | Testes | |
|---|---|---|---|---|---|---|---|
| Treatment | No. of Animals | Average weight (gm) | % of Control | Average Length (cm) | % of Control | Average weight (gm) | % of Control |
| Control Boars | 22 | 60.5 ± 3.5* |  | 11.4 ± .21 |  | 263 ± 10.9 |  |
| Immunocastrate Boars | 27 | 41.3 ± 5.2 | 68.3 | 9.5 ± .47 | 83.3 | 198 ± 11.3 | 75.3 |

*means ± standard errors

Figure 13:
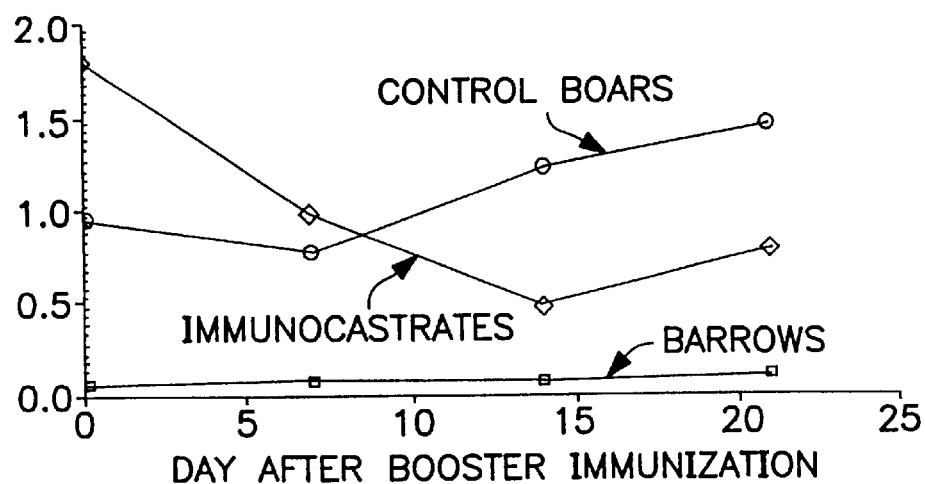
FIG. 13 shows a comparison of average serum testosterone levels in barrows, untreated boars, and immunocastrated boars (vaccinated with leukotoxin-GnRH fusion proteins) as described in Example 10.

The average serum testosterone levels in all three experimental groups was determined using a standard radioimmunoassay of serum testosterone levels with a sensitivity of 25 pg/mL. The assays were conducted on Day 0, Day 7, Day 14, and Day 21 after the booster immunizations (and placebo vaccinations in the control boar and barrow groups). The results of the assays are depicted in FIG. 13. As can be seen, the serum testosterone levels in the vaccinated animals decreased after vaccination, while the levels in the control boars increased.

(c) Carcass Composition:

Commercial aspects of the carcass composition of animals from each experimental group were assessed after slaughter of the animals. In particular, average body weights and fat content were determined, average measurements of the loin eye were taken, and the average weight of trimmed hams and loin was determined. The results of the carcass assessments are reported in Table 5. As can be seen, the carcass data show that the control boars and immunocastrates (vaccinated animals) had very similar carcass compositions, whereas the barrows had appreciably more body fat, less body lean. In addition, the growth performance of the barrows reached a plateau over the last 24 days of life (results not shown). These carcass data are consistent with the objective of having the carcass compositions of the immunocastrated animals mimic that of the control boars for all but the final few days of their growing period.

TABLE 5

Carcass Data

|  | Borrows | Control Boars | Immunocastrates |
|---|---|---|---|
| Kill wt (kg) | 110.5 | 115.2 | 115.4 |
| Fat (mm) | 19.1 | 15.7 | 15.3 |
| Loin eye (cm$^2$) | 41.5 | 44.5 | 44.2 |
| Trim Primal (kg) | 27.3 | 28.4 | 28.2 |
| Trimmed ham (kg) | 7.70 | 8.23 | 8.11 |
| Trimmed loin (kg) | 7.38 | 7.79 | 7.65 |

Figure 14:
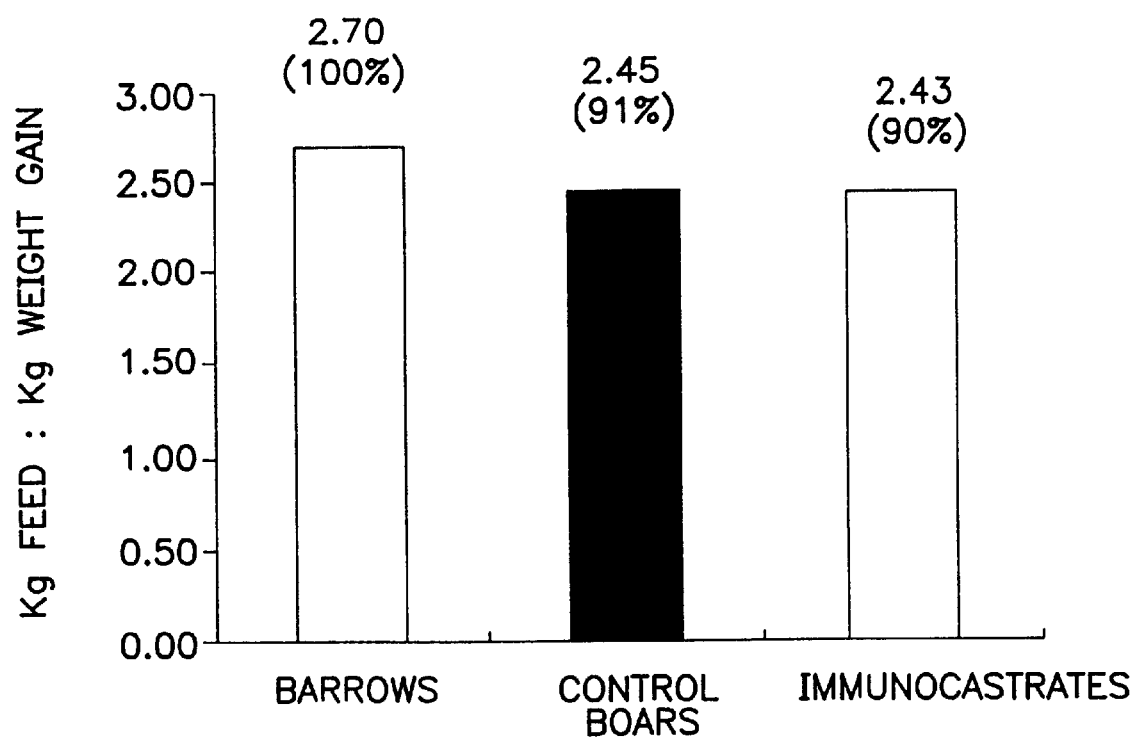
FIG. 14 shows a comparison of feed conversion efficiency (expressed as the ratio of Kg feed:Kg weight gain) in barrows, untreated boars, and immunocastrated boars (vaccinated with leukotoxin-GnRH fusion proteins) as described in Example 10.
Figure 15:
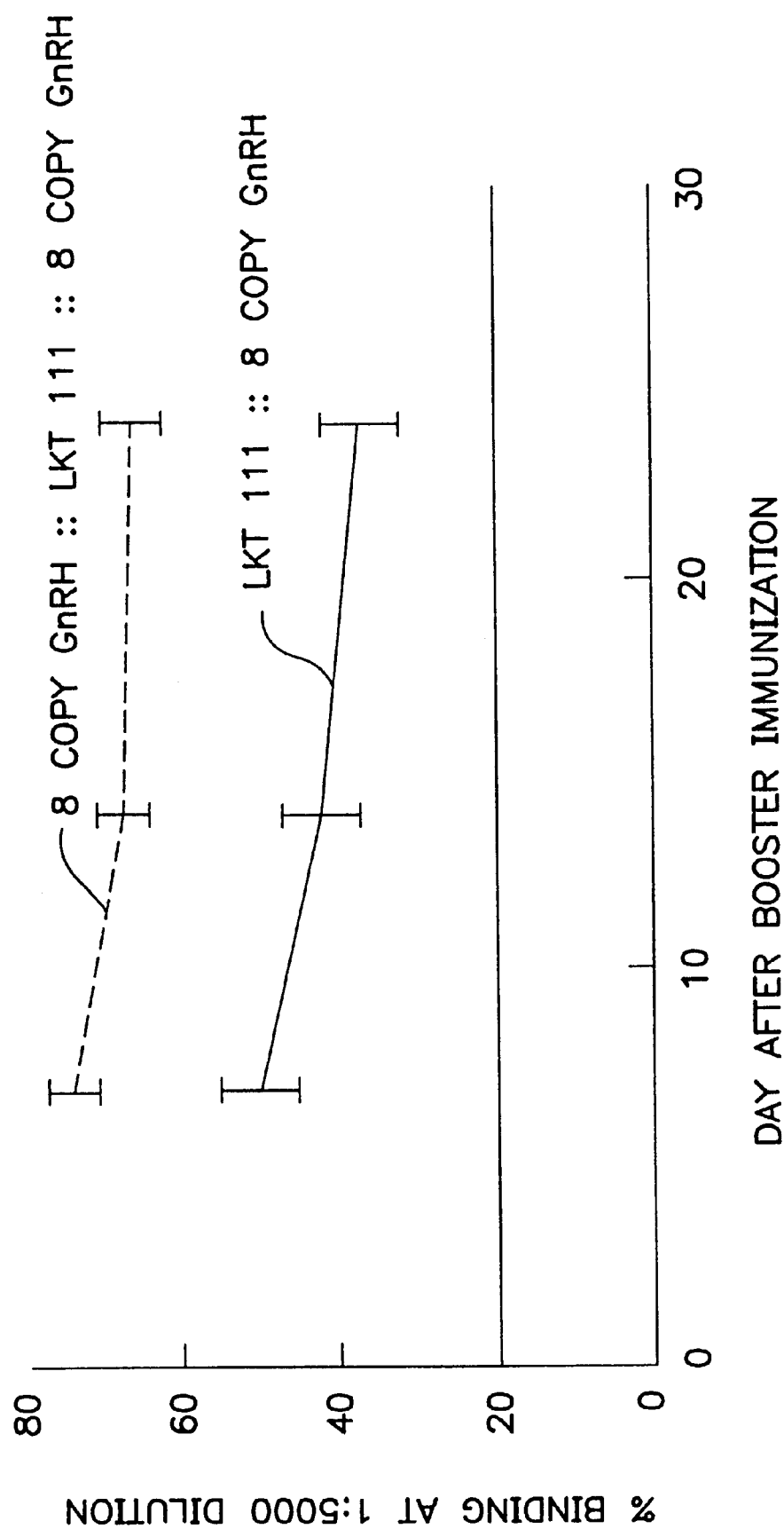
FIG. 15 shows a comparison of average serum anti-GnRH antibody titres in animals injected with a vaccine composition containing a LKT::8 copy GnRH fusion protein, or a vaccine composition containing an 8 copy GnRH::LKT::8 copy GnRH fusion protein as described in Example 11.

(d) Feed Conversion:

The feed conversion efficiency of animals from each of the experimental groups was measured over the period of weaning to slaughter. In particular, average feed conversion efficiency was expressed as the ratio of Kg feed:Kg weight gain in the animals. The results are depicted in FIG. 14. As can be seen, feed conversion in the control boars and the immunocastrates (vaccinated animals) was about 10% more efficient than feed conversion in the barrows.

(e) Boar Taint Component Levels:

The ability of the 8 copy GnRH-LKT fusion vaccine formulation to reduce boar taint in vaccinated animals was assessed by assaying the androsterone levels (a boar taint component) in fat and salivary glands of animals from each of the experimental groups. Andostenone levels were quantified by a standard chemical method on fat and salivary gland specimens obtained from each group. The results are reported in Table 6. As can be seen, the control boars had appreciably higher andostenone concentrations relative to the barrows and the immunocastrates (vaccinated animals).

TABLE 6

|  | Borrows | Control Boars | Immunocastrates |
|---|---|---|---|
| Fat Andostenone | 0.14 µg/g | 0.44 µg/g | 0.26 µg/g* |
| Salivary Andostenone | 33.76 µg/g | 40.46 µg/g | 30.18 µg/g |

*p less than .01

All of the above results indicate that immunocastration vaccine formulations containing the short LKT::8 copy GnRH fusion molecules provide a commercially viable alternative to surgical castration methods.

EXAMPLE 11

Comparison of In Vivo Immunogenic Activity of Fusion Molecules Having One or Two GnRH Multimers In order to compare the ability of LKT-GnRH fusion proteins comprising either a single GnRH multimer (containing 8 tandem repeats of GnRH), or two GnRH multimers (both containing 8 tandem repeats of GnRH), to elicit an anti-GnRH immunological response in vivo, several vaccination trials were carried out.

Cultures of *E. coli* containing plasmids pCB114 (one 8 copy GnRH multimer, ligated to the C'-terminus of LKT 111), and pCB122 (two 8 copy GnRH multimers, one ligated to the N'-terminus of LKT 111 and the other ligated to the C'-terminus of LKT 111) were prepared as described above. Vaccines derived from cultures containing the pCB114 plasmid were formulated to contain 160 µg of the fusion molecules (25 µg total of GnRH) in a 2 mL final volume of VSA-3 adjuvant. Vaccines derived from cultures containing the pCB122 plasmid were formulated to contain 185 µg of the fusion molecules (50 µg total of GnRH) in a 2 mL final volume of VSA-3 adjuvant. In this manner, the amount of the LKT carrier molecule was kept constant (135 µg total of LKT per formulation) in both preparations. The vaccine formulations were used in the following vaccination trials.

(a) Anti-GnRH Antibody Titre and Functional Activity of the Anti-GnRH Antibody Molecules:

A comparison between anti-GnRH antibody titres elicited by the two experimental vaccine formulations was carried out, wherein the ability of the elicited antibodies to block the effect of endogenously produced GnRH was also assessed. In particular, three groups of male pigs were established as follows: 50 animals were injected with the single GnRH multimer vaccine composition (LKT 111::8 copy GnRH fusions obtained from pCB114), 10 animals were injected with the plural GnRH multimer vaccine composition (8 copy GnRH::LKT 111::8 copy GnRH fusions obtained from pCB122), and 10 control animals were injected with 2 mL of the VSA-3 adjuvant alone.

Vaccinations were carried out at weaning (21 days of age), and the animals were boosted 30 days later. Blood was collected 14 and 28 days after the booster immunization. Serum was obtained and assayed for anti-GnRH antibody titer and serum levels of Luteinizing Hormone (LH). Serum anti-GnRH antibody titres were determined at a final serum dilution of 1:5000 using iodinated GnRH in a standard radioimmunoassay. Serum levels of LH were assayed using porcine LH as a reference standard in a standard radioimmunoassay. The results of the assays, given as mean values±standard errors, are reported in Table 7. As can be seen by the data depicted in Table 7, anti-GnRH antibody titres were higher in animals injected with the plural GnRH multimer vaccine composition (8 copy GnRH::LKT 111::8 copy GnRH) than seen with the animals receiving the single GnRH multimer vaccine (LKT 111::8 copy GnRH). Further, the animals receiving the plural GnRH multimer vaccine had lower serum LH levels. This reduction in serum LH reflects the ability of the anti-GnRH antibodies produced in the immunized animals to block the effect of endogenously produced GnRH. Finally, 100% of the animals receiving the plural GnRH multimer vaccine responded to the vaccine by producing anti-GnRH antibodies, whereas 90–92% of the animals receiving the single GnRH multimers responded.

TABLE 7

|  | GnRH Antibodies at Day | | Serum LH at Day |
|---|---|---|---|
|  | 14 | 28 | 14 |
| Day after the Booster Treatments 1 (Control) | 0.5 ± .3 | 0.5 ± .3 | 1.16 ± .22 |

TABLE 7-continued

|  | GnRH Antibodies at Day | | Serum LH at Day |
| --- | --- | --- | --- |
| Treatment 2 LKT III::8 copy GnRH 160 µg (25 µg GnRH) | 44.6 ± 4.1 | 37.2 ± 4.1 | 0.13 ± .04 |
| Treatment 3 8 copy GnRH::LKT III::8 copy GnRH 185 µg (50 µg GnRH) | 60.5 ± 6.9 | 51.8 ± 7.5 | .06 ± .02 |

(b) Comparison of Anti-GnRH Titres and Assessment of the Effect of Increased Vaccine Dosages:

The immunogenicity of the two vaccine formulations (the 8 copy GnRH single multimer antigen and the 16 copy GnRH plural multimer antigen) was again assessed as follows. Two experimental groups of 20 male pigs each were established. Animals in the first group were vaccinated at weaning (Day 21 of age) with 160 μg of the single multimer antigen preparation, and then boosted 33 days later with the same dosage. Animals in the second group were vaccinated at weaning (Day 21 of age) with 185 μg of the plural multimer antigen preparation and also boosted 33 days later. Blood was collected at 8, 14, and 24 days after the booster injections, and serum was assayed for anti-GnRH antibody molecules at a final dilution of 1:5000 using standard radioimmunoassay as previously described. The results are depicted in FIG. 15. As can be seen, the antibody response to the plural multimer vaccine (8 copy GnRH::LKT 111::8 copy GnRH) was higher ($P<0.001$) than for the single multimer vaccine (LKT 111::8 copy GnRH). Referring still to FIG. 15, the horizontal line at 20% on the Y axis represents an antibody titre which, in previous trials not reported herein, have been shown to suppress secretion of LH in vaccinated animals. Once again, 100% of the animals receiving the plural GnRH multimer vaccine responded (produced anti-GnRH antibodies), while approximately 90–92% of the animals receiving the single multimer vaccine responded.

In order to determine if the increased immunogenicity observed with the plural GnRH multimer vaccine is due to the increased dosage of the GnRH antigen (e.g., 50 μg GnRH in the [8 copy GnRH::LKT 111::8 copy GnRH] vaccine, as compared to 25 μg GnRH in the [LKT 111::8 copy GnRH] vaccine), the following study was carried out. Three groups of 20 pigs each were vaccinated at weaning (21 days of age) and boosted approximately 30 days later with the single GnRH multimer vaccine composition (LKT 111::8 copy GnRH fusions obtained from pCB114) at the following dosages: 50 μg, 150 μg and 450 μg of the fusion protein, respectively. Blood was collected at 14, 28 and 64 days after the booster injection. Serum was assayed for anti-GnRH antibodies at a final dilution of 1:5000 as described above. The results are reported in Table 8. As can be seen, no appreciable increase in anti-GnRH antibody titres were obtained in response to vaccination with increased dosages of the single GnRH multimer vaccine composition. This indicates that the increased immunogenicity observed with plural GnRH multimer vaccine (8 copy GnRH::LKT 111::8 copy GnRH fusions obtained from pCB122) is not due to increased GnRH antigen concentration; rather the increased immunogenicity is likely due to the three dimensional structure of the particular LKT-GnRH fusion molecule, or in the physical presentation of the GnRH antigen to antibody producing cells.

TABLE 8

| Dose (μg) LKT III::8 | % Binding at 1:5000 Dilution at Day after Boost | | |
|---|---|---|---|
| copy GnRH | Day 14 | Day 28 | Day 64 |
| 50 μg | 60.9 ± 4.8 | 50.7 ± 5.8 | 22.0 ± 4.7 |
| 150 μg | 59.0 ± 4.9 | 46.0 ± 4.9 | 16.8 ± 3.6 |
| 450 μg | 62.6 ± 4.0 | 56.5 ± 4.7 | 22.8 ± 4.8 |

EXAMPLE 12

Dose Response Study with LKT-GnRH Fusion Molecules Having Two GnRH Multimers In order to determine optimal dosages of vaccine compositions formed from LKT-GnRH fusion proteins comprising two GnRH multimers (both containing 8 tandem repeats of GnRH), the following in vivo dose response study was carried out.

Cultures of *E. coli* containing plasmid pCB122 (two 8 copy GnRH multimers, one ligated to the N'-terminus of LKT 111 and the other ligated to the C'-terminus of LKT 111) were prepared as described above. Seven vaccines derived from cultures containing the pCB122 plasmid were formulated at the following dosages of total fusion protein: 0 μg (control); 1 μg; 5 μg; 10 μg; 20 μg; 40 μg; and 80 μg, each in a 1 mL final volume of VSA-3 adjuvant.

Seven experimental groups of 20 animals each were assembled and vaccinated with the above-described vaccine formulations. A blood sample was taken at day 35 after the vaccination, and anti-GnRH antibody titres were measured at a final dilution of 1:100 in a standard radioimmunoassay as described above. The results of the assay are reported in Table 9. The titres are expressed as % binding as above. As can be seen, statistically 0 μg of the fusion protein was different from all other values. The 1 μg fusion protein dose was lower ($p<0.009$) than all other values obtained from groups receiving the protein antigen. The 5 μg dose was less than the 20 μg dose ($p<0.06$), however, all values for doses above 10 μg total fusion protein were statistically similar. These data show that the optimal dosage of the vaccine derived from the fusion protein of plasmid pCB122 (8 copy GnRH::LKT 111::8 copy GnRH) is approximately 20–40 μg of the fusion protein.

TABLE 9

| | 8 copy GnRH::LKT 111::8 copy GnRH Dose (μg) | | | | | | |
|---|---|---|---|---|---|---|---|
| | 0 | 1 | 5 | 10 | 20 | 40 | 80 |
| Titre $\bar{x}$ | 2.6 | 20.5 | 47.9 | 52.0 | 59.6 | 62.0 | 64.6 |
| $S\bar{x}$ | ±.6 | 5.0 | 5.8 | 4.6 | 4.4 | 3.4 | 3.6 |

EXAMPLE 13

Prediction of T-cell Epitopes in the Recombinant LKT 352 and LKT 111 Molecules In order to predict potential T-cell epitopes in the leukotoxin polypeptide sequences employed in the LKT-GnRH chimeras of the present invention, the method proposed by Margalit and co-workers (Margalit et al., *J. Immunol* (1987)

138:2213) was performed on the amino acid sequence corresponding to numbers 1 through 199 of the LKT molecule as depicted in Table 10. Under the subject method, the amino acid sequence of the leukotoxin polypeptide sequence was compared to other sequences known to induce a T-cell response and to patterns of types of amino acids which are believed to be required for a T-cell epitope. The results of the comparison are depicted in Table 10.

As can be seen by the predictive results thus obtained, there are several short sequences in the leukotoxin peptide which are identified as potential T-cell epitopes using the criteria suggested by Margalit et al (supra). More particularly, 9 sequences were identified as having a (Charged/Gly-Hydrophobic-Hydrophobic-Polar/Gly) sequence (indicated as pattern "1" in Table 10), and 3 sequences were identified as having a (Charged/Gly-Hydrophobic-Hydrophobic-Hydrophobic/Pro-Polar/Gly) sequence (indicated as pattern "2" in Table 10). By coupling these data with the in vivo anti-GnRH activity produced by both the LKT 352 and the LKT 111 carrier systems in Examples 7 and 8 above, it is indicated that critical T-cell epitopes are retained in the shortened LKT 111 molecule, and that those epitopes are likely contained within the N-terminal portion of the LKT 352 and LKT 111 molecules.

TABLE 10

LKT Sequence Patterns Corresponding
To Potential T-cell Epitopes

| LKT Amino Acid Sequences Showing Pattern "1": | |
| --- | --- |
| GTID(SEQ ID NO: 22) | (aa's 27–30) |
| GITG(SEQ ID NO: 23) | (aa's 66–69) |
| GVIS(SEQ ID NO: 24) | (aa's 69–72) |
| HVAN(SEQ ID NO: 25) | (aa's 85–88) |
| KIVE(SEQ ID NO: 26) | (aa's 93–96) |
| DLAG(SEQ ID NO: 27) | (aa's 152–155) |
| KVLS(SEQ ID NO: 28) | (aa's 162–165) |
| DAFE(SEQ ID NO: 29) | (aa's 171–174) |
| KLVQ(SEQ ID NO: 30) | (aa's 183–186) |
| GIID(SEQ ID NO: 31) | (aa's 192–195) |
| LKT Amino Acid Sequence Showing Pattern "2": | |
| RYLAN(SEQ ID NO: 32) | (aa's 114–118) |
| KFLLN(SEQ ID NO: 33) | (aa's 124–128) |
| KAYVD(SEQ ID NO: 34) | (aa's 167–171) |

EXAMPLE 14

Prediction of the Physical Structure of LKT-GnRH Fusion Proteins Obtained From PCB122

In order to predict the physical structure of the B-cell epitopes of the 8 copy GnRH::LKT 111::8 copy GnRH fusion molecules obtained from the pCB122 construct, the pCB122 amino acid sequence (depicted in FIGS. 9-1 through 9-6) was analyzed using previously described methods for determining physical protein structure. Rost et al. (1993) *J. Mol. Biol.* 232:584–599, Rost et al. (1994) *Proteins* 19:55–72, and Rost et al. (1994) *Proteins* 20:216–226. In particular, the prediction was performed by a system of neural networks where the input data consisted of a multiple sequence alignment. The network analysis was performed using the program MaxHom (Sander et al. (1991) *Proteins* 9:56–68, where training for the residue solvent accessibility was taken from Kabsch et al. (1983) *Biopolymers* 22:2577–2637. The neural network analysis assessed each amino acid in the pCB122 sequence, and predicted if the residue would be present as a loop, helix or exposed structure. In the prediction, the 8 copies of GnRH at the amino terminal of the pCB122 molecule were predicted to exist mainly as a loop structure, while the 8 copies of GnRH at the carboxyl terminal have a mixture of predicted structures (loop, helix and exposed residue).

These data suggest that the enhanced immunogenicity observed with the 8 copy GnRH::LKT 111::8 copy GnRH fusion molecules obtained from the pCB122 construct may be related to the different three dimensional structures of the GnRH antigens in the molecule.

D. Industrial Applicability

The leukotoxin-GnRH chimeras of the present invention are of use in providing immunogens that, when administered to a vertebrate host, serve to immunize the host against endogenous GnRH, which in turn acts to inhibit the reproductive function or capability of the host.

Notwithstanding the specific uses exemplified in this specification, the novel chimeric molecules disclosed herein provide a means for obtaining fusion proteins comprising more than one GnRH polypeptide, occurring in either multiple or tandem repeats, which are fused to immunogenic epitopes supplied by the leukotoxin polypeptide portion of the molecule (and in some cases by spacer peptide sequences occurring between selected GnRH sequences). The subject chimeric proteins constructed under the present invention provide enhanced immunogenicity to the fused GnRH peptide sequences, allowing an immunized vertebrate host to mount an effective immune response toward endogenous GnRH; effecting an interruption in the synthesis and release of the two gonadotropic hormones, luteinizing hormone (LH) and follicle stimulating hormone (FSH) and rendering the host temporarily sterile. In this manner, the novel leukotoxin-GnRH constructs may be employed in immunosterilization vaccines to provide an alternative to invasive sterilization procedures currently practiced in domestic and farm animal husbandry.

The leukotoxin-GnRH fusion molecules can also be used to reduce the incidence of mammary tumors in mammalian subjects using vaccines comprising those molecules to block ovarian functions such as the production of the ovarian hormones estrogen and progesterone. In much the same manner, immunologically-sterilized canine and feline subjects will not develop pyometra (infection of the uterus), since the immunized animals will not produce progesterone which predisposes to that condition.

Other contemplated uses of the instant fusion molecules include population control, for example the interruption of reproduction capabilities in wild rodent populations. In this regard, the LKT-GnRH fusion molecules may be used as an alternative to population control measures currently practiced, such as poisoning and the like. The fusion products of the instant invention may also be administered in constructs having both slow and fast release components. In this manner, the need for multiple vaccinations may be avoided. Further, since the amino acid sequence of GnRH is highly conserved among species, a single leukotoxin-GnRH fusion vaccine product may be produced which will exhibit broad cross species effectiveness.

Thus, various chimeric proteins comprising leukotoxin fused to selected GnRH polypeptides have been disclosed. Although preferred embodiments of the subject invention have been described in some detail, it is understood that obvious variations can be made without departing from the spirit and the scope of the invention as defined by the appended claims.

Deposits of Strains Useful in Practicing the Invention

A deposit of biologically pure cultures of the following strains was made with the American Type Culture Collection (ATCC), 10801 University Boulevard, Manassas, Va. 20110-2209. The accession number indicated was assigned after successful viability testing, and the requisite fees were paid. The deposits were made under the provisions of the Budapest Treaty on the International Recognition of the Deposit of Microorganisms for the Purpose of Patent Procedure and the Regulations thereunder (Budapest Treaty). This assures maintenance of viable cultures for a period of thirty (30) years from the date of deposit and at least five (5) years after the most recent request for the furnishing of a sample of the deposit by the depository. The organisms will be made available by the ATCC under the terms of the Budapest Treaty, which assures permanent and unrestricted availability of the cultures to one determined by the U.S. Commissioner of Patents and Trademarks to be entitled thereto according to 35 USC §122 and the Commissioner's rules pursuant thereto (including 37 CFR §1.12). Upon the granting of a patent, all restrictions on the availability to the public of the deposited cultures will be irrevocably removed.

These deposits are provided merely as convenience to those of skill in the art, and are not an admission that a deposit is required under 35 USC §112. The nucleic acid sequences of these plasmids, as well as the amino acid sequences of the polypeptides encoded thereby, are incorporated herein by reference and are controlling in the event of any conflict with the description herein. A license may be required to make, use, or sell the deposited materials, and no such license is hereby granted.

| Strain | Deposit Date | ATCC No. |
|---|---|---|
| *P. haemolytica* serotype 1 B122 | Feb. 1, 1989 | 53863 |
| pAA101 in *E. coli* JM105 | Feb. 1, 1989 | 67883 |
| pAA352 in *E. coli* W1485 | Mar. 30, 1990 | 68283 |
| pCB113 in *E. coli* JM105 | Feb. 1, 1995 | 69749 |
| pCB111 in *E. coli* JM105 | Feb. 1, 1995 | 69748 |

What is claimed is:

1. A polynucleotide comprising a coding sequence for an LKT 111 polypeptide, said polynucleotide comprising the contiguous polynucleotide sequence of nucleotides 31 to 1473 of SEQ ID NO:9, or a polynucleotide with at least 80% sequence identity thereto.

2. The polynucleotide of claim 1, wherein the polynucleotide comprises a polynucleotide sequence with at least 90% sequence identity to the contiguous polynucleotide sequence of nucleotides 31 to 1473 of SEQ ID NO:9.

3. The polynucleotide of claim 1, wherein the polynucleotide comprises a polynucleotide sequence with at least 95% sequence identity to the contiguous polynucleotide sequence of nucleotides 31 to 1473 of SEQ ID NO:9.

4. The polynucleotide of claim 1, wherein the polynucleotide comprises the contiguous polynucleotide sequence of nucleotides 31 to 1473 of SEQ ID NO:9.

5. The polynucleotide of claim 1, wherein said polynucleotide comprises a polynucleotide sequence encoding amino acids 11–491 of SEQ ID NO:10.

6. A recombinant vector comprising the polynucleotide of claim 1 and control elements operably linked to said polynucleotide, whereby said coding sequence of said polynucleotide can be transcribed and translated in a host cell.

7. A recombinant vector comprising the polynucleotide of claim 2 and control elements operably linked to said polynucleotide, whereby said coding sequence of said polynucleotide can be transcribed and translated in a host cell.

8. A recombinant vector comprising the polynucleotide of claim 3 and control elements operably linked to said polynucleotide, whereby said coding sequence of said polynucleotide can be transcribed and translated in a host cell.

9. A recombinant vector comprising the polynucleotide of claim 4 and control elements operably linked to said polynucleotide, whereby said coding sequence of said polynucleotide can be transcribed and translated in a host cell.

10. A recombinant vector comprising the polynucleotide of claim 5 and control elements operably linked to said polynucleotide, whereby said coding sequence of said polynucleotide can be transcribed and translated in a host cell.

11. A host cell transformed with the recombinant vector of claim 6.

12. A host cell transformed with the recombinant vector of claim 7.

13. A host cell transformed with the recombinant vector of claim 8.

14. A host cell transformed with the recombinant vector of claim 9.

15. A host cell transformed with the recombinant vector of claim 10.

16. A method of producing a recombinant polypeptide comprising:
   (a) providing a population of host cells according to claim 11; and
   (b) culturing said population of host cells under conditions whereby the polypeptide encoded by said polynucleotide is expressed.

17. A method of producing a recombinant polypeptide comprising:
   (a) providing a population of host cells according to claim 12; and
   (b) culturing said population of host cells under conditions whereby the polypeptide encoded by said polynucleotide is expressed.

18. A method of producing a recombinant polypeptide comprising:
   (a) providing a population of host cells according to claim 13; and
   (b) culturing said population of host cells under conditions whereby the polypeptide encoded by said polynucleotide is expressed.

19. A method of producing a recombinant polypeptide comprising:
   (a) providing a population of host cells according to claim 14; and
   (b) culturing said population of host cells under conditions whereby the polypeptide encoded by said polynucleotide is expressed.

20. A method of producing a recombinant polypeptide comprising:
   (a) providing a population of host cells according to claim 15; and
   (b) culturing said population of host cells under conditions whereby the polypeptide encoded by said polynucleotide is expressed.

* * * * *